(12) United States Patent
Ashwell et al.

(10) Patent No.: US 7,902,192 B2
(45) Date of Patent: *Mar. 8, 2011

(54) INHIBITORS OF P38 AND METHODS OF USING THE SAME

(75) Inventors: Mark A. Ashwell, Carlisle, MA (US); Syed Ali, North Andover, MA (US); Jifeng Liu, Winchester, MA (US); Yanbin Liu, Acton, MA (US); Peter Lohse, Weston, MA (US); Belew Mekonnen, Gilbertsville, PA (US); Robert Selliah, Midvale, UT (US); Manish Tandon, Framingham, MA (US); Woj Wrona, Waltham, MA (US); Valery Antonenko, Cupertino, CA (US)

(73) Assignee: ArQule, Inc., Woburn, MA (US)

( * ) Notice: Subject to any disclaimer, the term of this patent is extended or adjusted under 35 U.S.C. 154(b) by 942 days.

This patent is subject to a terminal disclaimer.

(21) Appl. No.: 10/556,161

(22) PCT Filed: May 14, 2004

(86) PCT No.: PCT/US2004/015368
§ 371 (c)(1),
(2), (4) Date: Apr. 19, 2007

(87) PCT Pub. No.: WO2004/110990
PCT Pub. Date: Dec. 23, 2004

(65) Prior Publication Data
US 2007/0270418 A1 Nov. 22, 2007

Related U.S. Application Data

(60) Provisional application No. 60/470,735, filed on May 15, 2003, provisional application No. 60/512,298, filed on Oct. 17, 2003.

(51) Int. Cl.
*C07D 498/04* (2006.01)
*A61K 31/41* (2006.01)

(52) U.S. Cl. ............... 514/235.8; 514/274; 514/275; 544/122; 544/310; 544/333

(58) Field of Classification Search .............. 544/122, 544/310, 333; 514/235.8, 274, 275
See application file for complete search history.

(56) References Cited

U.S. PATENT DOCUMENTS

| | | | |
|---|---|---|---|
| 3,455,924 A | 7/1969 | Lednicer | |
| 4,794,114 A | 12/1988 | Bender et al. | |
| 4,892,578 A | 1/1990 | Chang et al. | |
| 5,317,019 A | 5/1994 | Bender et al. | |
| 5,747,498 A | 5/1998 | Schnur et al. | 514/259 |
| 5,777,097 A | 7/1998 | Lee et al. | |
| 5,783,664 A | 7/1998 | Lee et al. | |
| 5,869,043 A | 2/1999 | McDonnell et al. | |
| 5,871,934 A | 2/1999 | Lee et al. | |
| 5,955,366 A | 9/1999 | Lee et al. | |
| 5,994,412 A | 11/1999 | Lee et al. | |
| 6,033,873 A | 3/2000 | McDonnell et al. | |
| 6,090,626 A | 7/2000 | Monia et al. | |
| 6,162,613 A | 12/2000 | Su et al. | |
| 6,187,799 B1 | 2/2001 | Wood et al. | |
| 6,302,838 B1 | 10/2001 | O'Reilly et al. | |
| 6,344,476 B1 | 2/2002 | Ranges et al. | |
| 6,376,214 B1 | 4/2002 | Kumar et al. | |
| 6,387,641 B1 | 5/2002 | Bellon et al. | |
| 6,410,518 B1 | 6/2002 | Monia | |
| 6,437,147 B1 | 8/2002 | Andersen et al. | |
| 6,683,100 B2 | 1/2004 | van Hoogevest | |
| 6,689,883 B1 | 2/2004 | Dumas et al. | |
| 6,806,258 B2 | 10/2004 | Monia | |
| 6,900,221 B1 | 5/2005 | Norris et al. | 514/266.4 |
| 7,449,458 B2 | 11/2008 | Bhamidipati et al. | 514/230.5 |
| 7,501,430 B2 * | 3/2009 | Lapierre et al. | 514/275 |
| 7,528,121 B2 | 5/2009 | Heron et al. | 514/81 |
| 2001/0006975 A1 | 7/2001 | Wood et al. | |
| 2002/0042517 A1 | 4/2002 | Uday et al. | |
| 2002/0058659 A1 | 5/2002 | Andersen et al. | |
| 2002/0137774 A1 | 9/2002 | Riedl et al. | |
| 2002/0165394 A1 | 11/2002 | Dumas et al. | |
| 2003/0078432 A1 | 4/2003 | Letavic et al. | |
| 2003/0125359 A1 | 7/2003 | Lyons et al. | |
| 2003/0144278 A1 | 7/2003 | Riedl et al. | |
| 2003/0181442 A1 | 9/2003 | Riedl et al. | |
| 2003/0207872 A1 | 11/2003 | Riedl et al. | |
| 2003/0207914 A1 | 11/2003 | Dumas et al. | |
| 2003/0216396 A1 | 11/2003 | Dumas et al. | |
| 2003/0216446 A1 | 11/2003 | Dumas et al. | |
| 2004/0023961 A1 | 2/2004 | Dumas et al. | |

(Continued)

FOREIGN PATENT DOCUMENTS
EP 0 951 467 B1 4/2003

(Continued)

OTHER PUBLICATIONS

Simone, Oncology: Introduction, Cecil Textbook of Medicine, 20th Edition, vol. 1, pp. 1004-1010, 1996.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 and 596.*
Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*

(Continued)

*Primary Examiner* — Deepak Rao
(74) *Attorney, Agent, or Firm* — Sunstein Kann Murphy & Timbers LLP

(57) ABSTRACT

In general, the present invention relates to compounds capable of inhibiting p38, methods for inhibiting p38 in vivo or in vitro, and methods for treating conditions associated with p38 activity or cytokine activity.

11 Claims, 9 Drawing Sheets

U.S. PATENT DOCUMENTS

| | | | |
|---|---|---|---|
| 2004/0087626 A1 | 5/2004 | Renhowe et al. | |
| 2004/0122237 A1 | 6/2004 | Amiri et al. | |
| 2006/0116357 A1 | 6/2006 | Heron et al. | 514/80 |
| 2007/0270384 A1 | 11/2007 | Pittam et al. | 514/80 |
| 2007/0270418 A1 | 11/2007 | Ashwell et al. | 514/233.2 |
| 2008/0032967 A1 | 2/2008 | Ashwell et al. | 514/217 |
| 2008/0045481 A1 | 2/2008 | Sependa et al. | 514/80 |
| 2009/0111985 A1 | 4/2009 | Ashwell et al. | 544/331 |

FOREIGN PATENT DOCUMENTS

| | | |
|---|---|---|
| EP | 1 114 051 B1 | 4/2003 |
| EP | 1 449 834 A2 | 8/2004 |
| JP | 61214793 | 2/1987 |
| WO | WO 91/00092 A1 | 1/1991 |
| WO | WO 95/03297 A1 | 2/1995 |
| WO | WO 97/32604 A1 | 9/1997 |
| WO | WO 97/36587 A1 | 10/1997 |
| WO | WO 98/52559 A1 | 11/1998 |
| WO | WO 99/20624 A1 | 4/1999 |
| WO | WO 99/32106 A1 | 7/1999 |
| WO | WO 99/32436 A1 | 7/1999 |
| WO | WO 99/32455 A1 | 7/1999 |
| WO | WO 00/12074 A2 | 3/2000 |
| WO | WO 00/42012 A1 | 7/2000 |
| WO | WO 00/71535 A1 | 11/2000 |
| WO | WO 02/04447 A1 | 1/2002 |
| WO | WO 02/062763 A2 | 8/2002 |
| WO | WO 02/083628 A1 | 10/2002 |
| WO | WO 02/085857 A2 | 10/2002 |
| WO | WO 03/000682 A1 | 1/2003 |
| WO | WO 03/033502 A1 | 4/2003 |
| WO | WO 03/047523 A2 | 6/2003 |
| WO | WO 03/047579 A1 | 6/2003 |
| WO | WO 03/068223 A1 | 8/2003 |
| WO | WO 03/068229 A1 | 8/2003 |
| WO | WO 03/068746 A1 | 8/2003 |
| WO | WO 03/087087 A2 | 10/2003 |
| WO | WO 03/102139 A2 | 12/2003 |
| WO | WO 2004/014870 A1 | 2/2004 |
| WO | WO 2004/019941 A1 | 3/2004 |
| WO | WO 2004/037789 A3 | 5/2004 |
| WO | WO 2004/072025 A2 | 8/2004 |
| WO | WO 2004/080464 A1 | 9/2004 |
| WO | WO 2004/085399 A1 | 10/2004 |
| WO | WO 2004/087905 A2 | 10/2004 |
| WO | WO 2004/089929 A1 | 10/2004 |
| WO | WO 2004/110990 | 12/2004 |
| WO | WO 2005/023761 A2 | 3/2005 |
| WO | WO 2006/044869 | 4/2006 |
| WO | WO 2007/123892 | 11/2007 |

OTHER PUBLICATIONS

Douglas, Jr., Introduction of Viral Diseases, Cecil Textbook of Medicine, 20th Edition, vol. 2, pp. 1739-1747, 1996.*
Ulrich, Chapter 4: Crystal Characteristics, Kirk Othmer Encyclopedia of Chemical Technology (7 pages), Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
European Patent Office; Authorized Officer: Beyss-Kahana, E., *International Preliminary Report on Patentability and the Written Opinion of the International Searching Authority*, International Application No. PCT/US2007/009348, dated Oct. 22, 2008, 9 pages.
Allen, et al., "*CI-1040 (PD184352), A Targeted Signal Transduction Inhibitor of MEK (MAPKK)*," Semin. Oncol. 30 (5 Suppl 16), pp. 105-116, 2003.
Davies, et al., "*Mutations of the BRAF Gene in Human Cancer*," Nature, 417, pp. 949-954, 2002.
Hoeflich, et al., "*Oncogenic BRAF Is Required for Tumor Growth and Maintenance in Melanoma Models*," Cancer Res., 66(2), pp. 999-1006, 2006.
Li, et al., "*Selective Killing of Cancer Cells by Beta-Lapachone: Direct Checkpoint Activation as a Strategy Against Cancer*," Proc. Natl. Acad. Sci. USA., 100(5), pp. 2674-2678, 2003.
Marais, et al., "*Control of the ERK MAP Kinase Cascade by Ras and Raf*," Cancer Surv., 27, pp. 101-125, 1996.
Robinson, et al., "*Mitogen-Activated Protein Kinase Pathways*," Curr. Opin. Cell Biol., 9, pp. 180-186, 1997.
Sharma, et al., "*Mutant v599EB-Raf Regulates Growth and Vascular Development of Malignant Melanoma Tumors*," Cancer Res., 65(6), pp. 2412-2421, 2005.
Tuveson, et al., "*BRAF as a Potential Therapeutic Target in Melanoma and Other Malignancies*," Cancer Cell, 4, pp. 95-98, 2003.
Wellbrock, et al., "*v599E BRAF is an Oncogene in Melanocytes*," Cancer Res., 64, pp. 2338-2342, 2004.
Xing, "*BRAF Mutation in Thyroid Cancer*," Endocrine-Related Cancer, 12, pp. 245-262, 2005.
OSI Pharmaceuticals, Inc. and Genetech, Inc., Full prescription information for Tarceva® erlotinib tablets, 4 pages, 2007.
Adams et al., "Pyrimidinylimidazole Inhibitors of CSBP/p38 Kinase Demonstrating Decreased Inhibition of Hepatic Cytochrome P450 Enzymes" *Bioorg. Med. Chem. Lett.*, 8:3111-3116 (1998).
Adams et al., "Pyrimidinylimidazole Inhibitors of p38: Cyclic N-1 Imidazole Substituents Enhance p38 Kinase Inhibition and Oral Activity," *Bioorg. Med. Chem. Lett.*, 11:2867-2870 (2001).
Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," *J. Pharmacol. Exp. Ther.*, 279:1453-1461 (1996).
Bingham, "The Pathogenesis of Rheumatoid Arthritis: Pivotal Cytokines Involved in Degradation and Inflammation," *J. Rheumatol. Supp.*, 65:3-9 (2002).
Boehm et al., "New Inhibitors of p38 Kinase," *Expert Opinion on Therapeutic Patents*, 10(1):25-37 (2000).
Bondeson et al., "Tumour Necrosis Factor as a Therapeutic Target in Rheumatoid Arthritis and other Chronic Inflammatory Diseases: The Clinical Experience with Infliximab (REMICADE)," *Int. J. Clin. Pract.*, 55:211-216 (2001).
Bradley and Robinson, Kationoid Reactivity of Aromatic Compounds. Part I, (Database Beilstein, Beilstein Institute zur Foerderung der Wissenschaften), Accession No. 316203, *J.Chem. Soc.* 1254-1263 (1932).
Brinkman et al., "Engagement of Tumor Necrosis Factor (TNF) Receptor I Leads to ATF-2- and p38 Mitogen-Activated Protein Kinase-Dependent TNF-alpha Gene Expression," *J. Biol. Chem.*, 274:30882-30886 (1999).
Dong et al., "Map Kinases in the Immune Response," *Annu. Rev. Immunol.*, 20:55-72 (2002).
English et al., "Pharmacological Inhibitors of MAPK Pathways," *Trends in Pharmacological Sciences*, 23:40-45 (200).
Enslen et al., "Selective Activation of p38 Mitogen-Activated Protein (MAP) Kinase Isoforms by the MAP Kinase Kinases MKK3 and MKK6," *J. Biol. Chem.*, 273:1741-1748 (1998).
Feldmann et al., "Role of Cytokines in Rheumatoid Arthritis," *Annu. Rev. Immunol.*, 14:397-440 (1996).
Fresneda et al., "Synthetic Studies Towards the 2-Aminopyrimidine Alkaloids Variolins and Meridianins from Marine Origin," *Tetrahedron Letters*, 41:4777-4780 (2000).
Fuchs et al., "Stability of the ATF2 Transcription Factor is Regulated by Phosphorylation and Dephosphorylation," *J. Biol. Chem.*, 275:12560-12564 (2000).
Griswold et al., "Differentiation in vivo of Classical Non-Steroidal Antiinflammatory Drugs from Cytokine Suppressive Antiinflammatory Drugs and Other Pharmacological Classes Using Mouse Tumour Necrosis Factor Alpha Production," *Drugs Exp. Clin. Res.*, 19:243-248 (1993).
International Search Report for International Application No. PCT/US 2004/015368, (2005).
International Search Report for International Application No. PCT/US 2004/024441, (2005).
International Search Report for International Application No. PCT/US 2004/037390, (2006).
Joe et al., "Animal Models of Rheumatoid Arthritis and Related Inflammation," *Curr. Rheumatol. Rep.*, 1:139-148 (1999).

Keesler et al., "Purification and Activation of Recombinant p38 Isoforms Alpha, Beta, Gamma, and Delta," *Protein Expr. Purif.*, 14:221-228 (1998).

Keffer et al., "Transgenic Mice Expressing Human Tumour Necrosis Factor: A Predictive Genetic Model of Arthritis," *Embo J.*, 10:4025-4031 (1991).

Laufer et al., "An in vitro Screening Assay for the Detection of Inhibitors of Proinflammatory Cytokine Synthesis: a Useful Tool for the Development of New Antiarthritic and Disease Modifying Drugs," *Osteoarthritis Cartilage*, 10:961-967 (2002).

Laufer and Wagner, "From Imidazoles to Pyrimidines: New Inhibitors of Cytokine Release," *J. Med. Chem.*, 45:2733-2740 (2002).

Lee et al., "A Protein Kinase Involved in the Regulation of Inflammatory Cytokine Biosynthesis," *Nature*, 372:739-746 (1994).

Lee et al., "Bicyclic Imidazoles as a Novel Class of Cytokine Biosynthesis Inhibitors," *Ann. N.Y. Acad. Sci.*, 696:149-170 (1993).

Lee et al., "Inhibition of p38 MAP Kinase as a Therapeutic Strategy," *Immunopharmacology*, 47:185-201 (2000).

Liverton et al., "Design and Synthesis of Potent, Selective, and Orally Bioavailable Tetrasubstituted Imidazole Inhibitors of p38 Mitogen-Activated Protein Kinase," *J. Med. Chem.*, 42:2180-2190 (1999).

McLay et al., "The Discovery of RPR 200765A, a p38 MAP Kinase Inhibitor Displaying a Good Oral Anti-Arthritic Efficacy," *Bioorg. Med. Chem.*, 9:537-554 (2001).

Mekonnen et al., "A New and Facile Synthesis of Imidazo[2,1-b]Oxazoles," *J. Heterocyclic Chem.*, 34:589-599 (1997).

Ono and Han, "The p38 Signal Transduction Pathway: Activation and Function," *Cell. Signal.*, 12:1-13 (2000).

Pargellis et al., "Inhibition of p38 MAP Kinase by Utilizing a Novel Allosteric Binding Site," *Nat. Struct. Biol.*, 9:268-272 (2002).

Pugsley, "Etanercept. Immunex.," *Curr. Opin. Investig. Drugs*, 2:1725-1731 (2001).

Raingeaud et al., "Pro-Inflammatory Cytokines and Environmental Stress Cause p38 Mitogen-Activated Protein Kinase Activation by Dual Phosphorylation on Tyrosine and Threonine," *J. Biol. Chem.*, 270:7420-7426 (1995).

Raingeaud et al., "MKK3- and MKK6-Regulated Gene Expression is Mediated by the p38 Mitogen-Activated Protein Kinase Signal Transduction Pathway," *Mol. Cell. Biol.*, 16:1247-1255 (1996).

Regan et al., "Pyrazole Urea-Based Inhibitors of p38 MAP Kinase: From Lead Compound to Clinical Candidate," *J. Med. Chem.*, 45:2994-3008 (2002).

Revesz et al., "SAR of 4-Hydroxypiperidine and Hydroxyalkyl Substituted Heterocycles as Novel p38 Map Kinase Inhibitors," *Bioorg. Med. Chem. Lett.*, 10:1261-1264 (2000).

Turconi et al., "Synthesis of a New Class of 2,3-Dihydro-2-Oxo-1H-Benzimidazole-1-Carboxylic Acid Derivatives as Highly Potent 5-HT$_3$ Receptor Antagonists," *J. Med. Chem.*, 33:2101-2108 (1990).

* cited by examiner

INHIBITORS OF P38 AND METHODS OF USING THE SAME

REFERENCE TO RELATED APPLICATIONS

This application is a national phase application under 35 U.S.C. §371 of International Application Number PCT/US2004/015368, filed May 14, 2004, which application claims the benefit of U.S. Provisional Patent Application Ser. No. 60/470,735 filed May 15, 2003 and U.S. Provisional Patent Application Ser. No. 60/512,298, filed Oct. 17, 2003, all of which applications are herein incorporated by reference in their entireties.

BACKGROUND OF THE INVENTION

Many chronic and acute conditions are associated with perturbation of the inflammatory response. A large number of cytokines participate in this response, including, but not limited to, IL-1, IL-6, IL-8 and TNFα. Although these cytokines are normally expressed in response to many physiological stimuli, excess, unregulated, or excess and unregulated production of these cytokines often leads to inflammation and tissue damage. This is one mechanism by which diseases such as rheumatoid arthritis mediate morbidity (Keffer, J., et al, EMBO J., 13: 4025-4031, 1991, Feldmann, M., et al, Annu. Rev. Immunol., 14: 397-440, 1996 and Bingham, C. O., J. Rheumatol. Suppl., 65: 3-9, 2002). Currently there are several therapeutic agents that aim to reduce systemic levels of proinflammatory cytokines such as TNFα (Pugsley, M. K. Curr. Opin. Invest. Drugs, 2: 1725-1731, 2001 and Bondeson, J., and Maini, R. N., J. Clin. Pract., 55: 211-216, 2001), thus ameliorating the disease. These therapeutics act directly to reduce circulating levels or neutralize activity of the cytokine. However, these therapeutics do not directly block intracellular proteins that regulate the expression and secretion of proinflammatory cytokines or regulate the expression of other mediators of inflammation and tissue destruction.

The p38 MAP Kinase (p38, also known as CSBP or SAPK) signaling pathway has been reported to be responsible for the expression of pro-inflammatory cytokines that are elevated in many inflammatory and auto-immune diseases (see, e.g., Dong, C., et al., Annu. Rev. Immunol., 20: 55-72, 2002 and references cited therein). Thus, inhibitors of any part of the p38 MAP Kinase pathway or inhibitors of pathways that regulate the p38 MAP Kinase pathway may be useful as therapeutics for diseases or conditions in which inflammation or auto-immune responses are involved. (Lee, J. C., et al, Immunopharm, 47: 185-201, 2000). This pathway has been shown to be activated by cellular stressors, such as osmotic shock, UV light, free radicals, bacterial toxins, viruses, cytokines, and chemokines, to name a few, and in response, mediates the expression of several cytokines including, but not limited to, IL-1, IL-6, IL-8 and TNFα (Ono, K. and Han, J., Cellular Signalling, 12: 1-13, 2000 and references cited therein).

Typically the p38 MAP kinase pathway is directly or indirectly activated by cell surface receptors, such as receptor tyrosine kinases, chemokine or G protein-coupled receptors, which have been activated by a specific ligand, e.g., cytokines, chemokines or lipopolysaccharide (LPS) binding to a cognate receptor. Subsequently, p38 MAP kinase is activated by phosphorylation on residues threonine 180 and tyrosine 182. After activation, p38 MAP kinase can phosphorylate other intracellular proteins, including protein kinases, and can be translocated to the cell nucleus, where it phosphorylates and activates transcription factors leading to the expression of pro-inflammatory cytokines and other proteins that contribute to the inflammatory response, cell adhesion, and proteolytic degradation. For example, in cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of physiological responses to cellular stress, acute or chronic cellular stress leads to the excess, unregulated, or excess and unregulated expression of proinflammatory cytokines. This, in turn, leads to tissue damage, often resulting in pain and debilitation. The fact that there are four known isoforms of p38 MAP kinase (p38α, p38β, p38δ and p38γ), each showing different expression levels, tissue distributions and regulation, support the concept that they are involved in the etiology or sequelae of many diseases and physiological disturbances.

Indeed, many autoimmune diseases and diseases associated with chronic inflammation, as well as acute responses, have been linked to activation of p38 MAP kinase and over-expression or dysregulation of inflammatory cytokines. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; cancer; restenosis; silicosis; pulmonary sarcosis; bone resorption diseases, such as osteoporosis; graft-versus-host reaction; and auto-immune diseases, such as Multiple Sclerosis, lupus and fibromyalgia; AIDS and other viral diseases such as Herpes Zoster, Herpes Simplex I or II, influenza virus and cytomegalovirus; and diabetes mellitus.

Many studies have shown that reducing the activity of p38 MAP kinase, its upstream activators or its downstream effectors, either through genetic or chemical means, blunts the inflammatory response and prevents or minimizes tissue damage (see, e.g., English, J. M. and Cobb, M. H., Trends in Pharmacol. Sci., 23: 40-45, 2002; and Dong, C., et al, Annu. Rev. Immunol., 20: 55-72, 2002). Thus, inhibitors of p38 activity, which also inhibit excess or unregulated cytokine production and may inhibit more than a single pro-inflammatory cytokine, may be useful as anti-inflammatory agents and therapeutics. Furthermore, the large number of diseases associated with p38 MAP kinase-associated inflammatory responses indicates that there is a need for effective methods for treating these conditions. However, as of the filing date of the present application, there are no approved drugs available that are known to directly inhibit the p38 MAP kinase family of enzymes, and those approved drugs that act by reducing or neutralizing cytokine levels through binding to the cytokine are generally not orally bioavailable and must therefore be administered by techniques such as injection.

Accordingly, new compounds and methods for treating p38- and cytokine-associated conditions are needed.

SUMMARY OF THE INVENTION

In general, the present invention relates to compounds capable of inhibiting p38 map kinase, methods for inhibiting p38 map kinase in vivo or in vitro, methods for treating conditions associated with p38 map kinase activity or cytokine activity.

In one aspect, the invention provides compounds represented by Formula I:

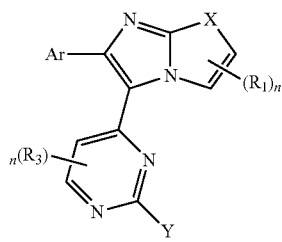

in which:

X is O or $S(O)_m$; Y is $OR_4$, or $NR_4R_5$; m is 0, 1, or 2; n is 1 or 2; $R_1$ represents 1 or 2 substituents independently selected from the group consisting of hydrogen, —CN, —COOH, halogen, $C_1$-$C_6$ alkyl, $C_1$-$C_6$ alkoxy; $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; Ar is an aryl group; $R_3$ represents 1-2 substituents independently selected from the group consisting of hydrogen, halogen, amino, $C_1$-$C_6$ alkyl, $C_1$-$C_6$ alkoxy, $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; $R_4$ and $R_5$ are each independently selected from the group consisting of hydrogen, $C_1$-$C_6$ alkyl, $C_3$-$C_6$ cycloalkyl, aryl, and heterocyclyl; or $R_4$ and $R_5$, taken together with the N atom to which they are attached, form a heterocyclic ring having from 3 to 8 atoms in the ring; or a prodrug, solvate, or salt (preferably a pharmaceutically acceptable salt) thereof;

with the proviso that when X is $S(O)_m$, m is 0, Ar is phenyl, Y is $NR_4R_5$, $R_4$ is hydrogen and $R_5$ is alkyl, then if $R_5$ is a hydroxyalkyl group, $R_5$ 1) is not —$CH_2(CH_3)_2CH_2OH$, and 2) is not substituted at the carbon atom alpha to the N atom with a phenyl group (that is, the carbon atom of $R_5$ that is attached to the N atom does not bear a phenyl group).

In preferred embodiments of Formula I, X is O or S, most preferably O. In preferred embodiments, Ar is phenyl or naphthyl, most preferably phenyl; in preferred embodiments, the phenyl group may be substituted with 1-3 halogen or trifluoromethyl substituents. A most preferred phenyl group is 4-fluorophenyl.

In additional preferred embodiments, Y is $NR_4R_5$, and preferably $R_4$ is hydrogen. In preferred embodiments, $R_5$ is selected from the group consisting of $C_2$-$C_6$ hydroxyalkyl, $C_2$-$C_6$ aminoalkyl, hydroxyaryl, aminoaryl, $C_3$-$C_6$ cycloalkyl and heterocyclyl, and still more preferably $R_5$ is a nitrogen-containing heterocycle (an azacycle).

In further preferred embodiments, $R_1$ and $R_3$ each represent H for all occurrences.

In other preferred embodiments, X is $S(O)_m$, and m is 0. In further preferred embodiments, Ar is phenyl or naphthyl, more preferably phenyl; in preferred embodiments, the phenyl group may be substituted with 1-3 halogen or trifluoromethyl substituents. A most preferred phenyl group is 4-fluorophenyl. In additional preferred embodiments, Y is $NR_4R_5$ and $R_4$ is hydrogen; $R_5$ is preferably a $C_2$-$C_6$ hydroxyalkyl group, a $C_2$-$C_6$ aminoalkyl group, a hydroxyaryl group, an aminoaryl group, or a nitrogen-containing heterocyclic ring having from 3 to 8 atoms in the ring, of which 1-3 atoms are nitrogen. In preferred embodiments, $R_1$ and $R_3$ are both hydrogen for all occurrences.

In another aspect, the invention provides pharmaceutical compositions comprising one or more compounds of Formula I, together with a pharmaceutically acceptable carrier.

In another aspect, the invention provides methods for treating p38-associated conditions. The methods include administering to the mammal an effective amount of compound of Formula I, such that the p38-associated condition is treated. In preferred embodiments, the p38-associated condition is rheumatoid arthritis, osteoarthritis or gouty arthritis (more preferably rheumatoid arthritis); Crohn's disease, ulcerative colitis, inflammatory bowel disease or psoriasis; or a proliferative disease, an auto-immune disease or an inflammatory disease.

In still another aspect, the invention provides methods for treating conditions associated with cytokine activity. The methods include administering to a subject in need of treatment an effective amount of compound of Formula I, such that the condition associated with altered cytokine activity is treated. In preferred embodiments, the p38-associated condition is rheumatoid arthritis, osteoarthritis or gouty arthritis; Crohn's disease, ulcerative colitis, inflammatory bowel disease or psoriasis; or a proliferative disease, an auto-immune disease or an inflammatory disease.

In still another aspect, the invention provides methods for treating conditions associated with specific isoforms of p38, for example, p38α, p38β, p38δ, or p38γ, or any combination thereof, and most preferably p38α. In preferred embodiments, the p38-associated condition is rheumatoid arthritis, osteoarthritis or gouty arthritis; Crohn's disease, ulcerative colitis, inflammatory bowel disease or psoriasis; or a proliferative disease, an auto-immune disease or an inflammatory disease.

In still another aspect, the invention provides methods for treating conditions associated with or mediated by p38, other kinases, or p38 and other kinases.

In still another aspect, the invention provides methods for treating disease conditions associated with a cytokine or cytokines, in which the cytokine (or cytokines) is (are) preferably selected from the group consisting of, but not limited to, IL-1, IL-6, IL-8, and TNFα. In general, the methods include administering to a mammal (e.g., a mammal in need of such treatment) an effective amount of a compound of Formula I, such that the mammal is treated. A preferred subject mammal is a human.

In yet another aspect, the invention provides methods for inhibiting the activity of p38 in a cell, in vitro or in vivo. In general, the methods include contacting a cell containing p38 with an effective p38-inhibiting amount of a compound of Formula I, under conditions such that p38 activity in the cell is inhibited.

In another aspect, the invention provides methods for determining the presence, location or quantity or any combination thereof of p38 protein in a cell or tissue sample. The methods include: a) contacting the cell or tissue sample with a compound of Formula I under conditions such that the compound of Formula I can bind to p38 protein; and b) determining the presence, location or quantity or any combination thereof of the compound of Formula I in the cell or tissue sample, thereby determining the presence, location or quantity or any combination thereof of p38 protein in the cell or tissue sample.

In certain embodiments of the therapeutic methods of the invention, one or more compound of Formula I may be combined with another agent, e.g., another pharmaceutically-active agent, for use in the inventive methods.

In still another aspect, the invention provides compounds represented by Formula II:

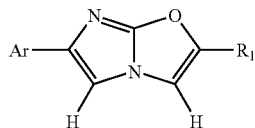

in which:

R$_1$ is selected from the group consisting of hydrogen, —CN, —COOH, halogen, C$_1$-C$_6$ alkyl, C$_1$-C$_6$ alkoxy; C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl; and Ar is an aryl group. Compounds of Formula II are useful, inter alia, for the synthesis of the imidazooxazole and imidazothiazole compounds of Formula I. In preferred embodiments of Formula II, Ar is phenyl or naphthyl, most preferably phenyl; in certain preferred embodiments, the phenyl group is substituted with 1-3 halogen, trifluoromethyl, or C$_1$-C$_6$ alkoxy substituents. A most preferred phenyl group is 4-fluorophenyl. In further preferred embodiments, R$_1$ is H.

In yet another aspect, the invention provides compounds of Formula III:

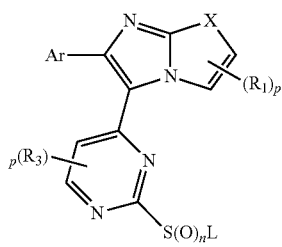

in which:

X is O or S(O)$_m$; m and n are each independently 0, 1, or 2; p is 1 or 2; R$_1$ is independently selected from the group consisting of hydrogen, —CN, —COOH, halogen, C$_1$-C$_6$ alkyl, C$_1$-C$_6$ alkoxy; C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl; Ar is an aryl group; R$_3$ is independently selected from the group consisting of hydrogen, halogen, amino, C$_1$-C$_6$ alkyl, C$_1$-C$_6$ alkoxy, C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl; and L is a C$_1$-C$_6$ alkyl group or an aryl group; or a salt thereof. In preferred embodiments of Formula III, X is O or S, most preferably O. In preferred embodiments, Ar is phenyl or naphthyl, most preferably phenyl; in certain preferred embodiments, the phenyl group is substituted with 1-3 halogen, trifluoromethyl, or C$_1$-C$_6$ alkoxy substituents. A most preferred phenyl group is 4-fluorophenyl. In further preferred embodiments, R$_1$ and R$_3$ each represent H for all occurrences. Compounds of Formula III are useful, e.g., for preparing compounds of Formula I, as described herein.

In yet another aspect, the invention provides methods for making compounds of Formula III. The method includes reacting a compound represented by Formula IV:

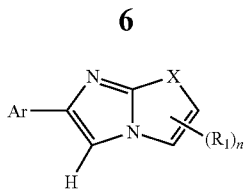

in which:

X is O or S(O)$_m$; m is 0, 1, or 2; n is 1 or 2; R$_1$ is independently selected from the group consisting of hydrogen, —CN, —COOH, halogen, C$_1$-C$_6$ alkyl, C$_1$-C$_6$ alkoxy; C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl; and Ar is an aryl group; or a salt thereof, with a compound represented by Formula V:

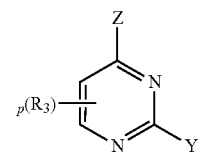

in which:

Z is selected from the group consisting of halogen, triflate, mesylate, or another suitable group; p is 1 or 2; R$_3$ is independently selected from the group consisting of hydrogen, halogen, amino, C$_1$-C$_6$ alkyl, C$_1$-C$_6$ alkoxy, C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl;

Y is S(O)$_n$L; n is 0, 1, or 2; and L is a C$_1$-C$_6$ alkyl group; or a salt thereof, in the presence of a metal catalyst and under conditions such that the compound of Formula III is formed, thereby preparing the compound of Formula III. In preferred embodiments, in the compound of Formula IV, X is O or S, most preferably O; in certain preferred embodiments, in the compound of Formula IV, Ar is phenyl or naphthyl, most preferably phenyl; in certain preferred embodiments, the phenyl is substituted with 1-3 halogen, trifluoromethyl, or C$_1$-C$_6$ alkoxy substituents; a most preferred phenyl group is 4-fluorophenyl. In further preferred embodiments, R$_1$ and R$_3$ each represent H for all occurrences in compounds of Formula IV or V.

The present invention includes a method for preparing a compound of Formula I or a salt thereof comprising reacting a compound of Formula III in which n is 2 with a nucleophile of the formula HOR$_4$ or HNR$_4$R$_5$, in which R$_4$ and R$_5$ have the meanings described in Formula I, or a conjugate base thereof, under conditions such that the group —S(O)$_n$ is displaced and a compound of Formula I, or a salt thereof, is formed.

These and other aspects and advantages of the invention will be apparent from the description herein.

DETAILED DESCRIPTION

Figure 1:
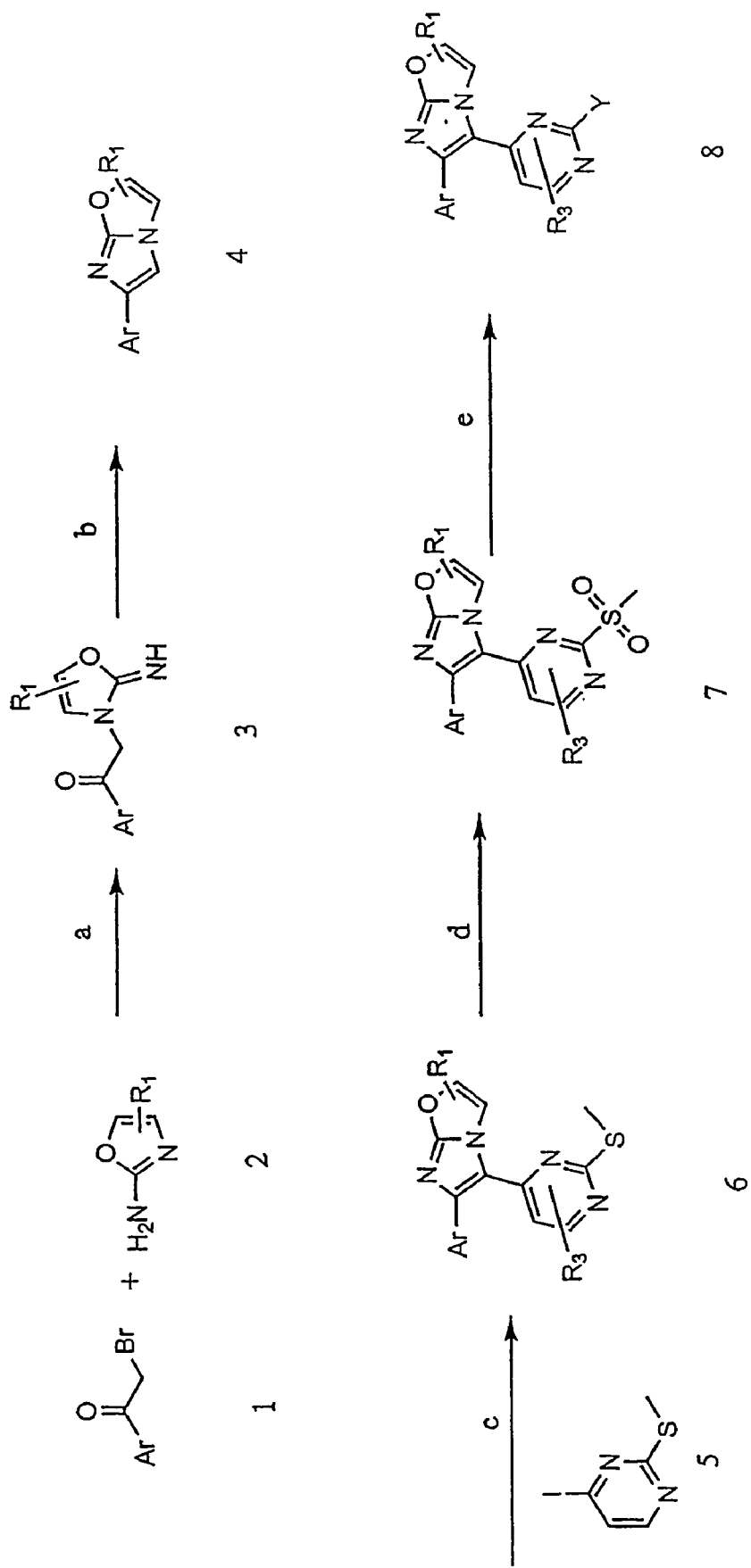
FIG. 1 illustrates one method for preparing imidazooxazole compounds of Formula I.

The present invention provides compounds, pharmaceutical compositions, and methods useful for treatment of human and veterinary conditions related to p38 or cytokine activity or associated with p38 or cytokines.

DEFINITIONS

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. A $C_1$-$C_6$ alkyl group is an alkyl group having from one to six carbon atoms in the straight or branched alkyl backbone. Alkyl groups optionally can be substituted with one or more moieties such as hydroxyl group, carboxylate, oxo, halogen, thiol, cyano, nitro, amino, —$NR_{12}R_{13}$, $C_1$-$C_6$ alkylthio, arylthio, $C_1$-$C_6$ alkyl, $C_1$-$C_6$ alkoxy, aryloxy, alkylcarbonyloxy, arylcarbonyloxy, $C_3$-$C_6$ cycloalkyl, $C_3$-$C_6$ cycloalkyloxy, $C_2$-$C_6$ alkenyl, $C_2$-$C_6$ alkynyl, aryl, aminocarbonyl, $C_1$-$C_6$ alkylcarbonyl, $C_3$-$C_6$ cycloalkylcarbonyl, heterocyclylcarbonyl, arylcarbonyl, aryloxycarbonyl, $C_1$-$C_6$ alkoxycarbonyl, $C_3$-$C_6$ cycloalkyloxycarbonyl, heterocyclyloxycarbonyl, $C_1$-$C_6$ alkylsulfonyl, arylsulfonyl, a heterocyclyl group, and the like.

A "cycloalkyl" group refers to a cyclic alkyl group which has a ring having from three to seven carbon atoms in the ring portion. A cycloalkyl group may be substituted with one or moieties as described for alkyl groups.

The term "alkenyl" refers to a hydrocarbon radical having at least one carbon-carbon double bond. A $C_2$-$C_6$ alkenyl group is an alkenyl group having from two to six carbon atoms in straight or branched alkenyl backbone. Exemplary alkenyl radicals include, without limitation, vinyl, propenyl, 2-butenyl, and the like. An alkenyl group may be substituted with one or moieties as described for alkyl groups.

The term "alkynyl," as used herein, refers to a hydrocarbon radical having at least one carbon-carbon triple bond. A $C_2$-$C_6$ alkynyl group is an alkynyl group having from two to six carbon atoms in straight or branched alkynyl backbone. Exemplary alkynyl moieties include propynyl, 3-hexynyl, and the like. An alkynyl group may be substituted with one or moieties as described for alkyl groups.

The term "aryl" refers to an aromatic carbocyclic or heteroaromatic moiety, having one, two, or three rings. An aryl group may be carbocyclic or may optionally contain from 1-4 heteroatoms (such as nitrogen, sulfur, or oxygen) in the aromatic ring. Exemplary aryl radicals include, without limitation, phenyl, naphthyl, pyridyl, pyrimidyl, triazyl, quinazolinyl, thiazolyl, benzothiophenyl, furanyl, imidazolyl, and the like. An aryl group optionally can be substituted with one or more substituents such as hydroxyl group, halogen, thiol, cyano, nitro, amino, —$NR_{12}R_{13}$, $C_1$-$C_6$ alkylthio, arylthio, $C_1$-$C_6$ alkyl, $C_1$-$C_6$ alkoxy, aryloxy, alkylcarbonyloxy, arylcarbonyloxy, $C_3$-$C_6$ cycloalkyl, $C_3$-$C_6$ cycloalkyloxy, $C_2$-$C_6$ alkenyl, $C_2$-$C_6$ alkynyl, aryl, carboxylate, aminocarbonyl, $C_1$-$C_6$ alkylcarbonyl, $C_3$-$C_6$ cycloalkylcarbonyl, heterocyclylcarbonyl, arylcarbonyl, aryloxycarbonyl, $C_1$-$C_6$ alkoxycarbonyl, $C_3$-$C_6$ cycloalkyloxycarbonyl, heterocyclyloxycarbonyl, aryloxycarbonyl, $C_1$-$C_6$ alkoxycarbonyl, $C_1$-$C_6$ alkylsulfonyl, arylsulfonyl, a heterocyclyl group, and the like.

The term "heterocyclyl" or "heterocycle" refers to a stable non-aromatic 3-7 membered monocyclic heterocyclic ring or 8-11 membered bicyclic heterocyclic ring which is either saturated or unsaturated, and may be fused, spiro or bridged to form additional rings. Each heterocycle consists of one or more carbon atoms and from one to four heteroatoms selected from the group consisting of nitrogen, oxygen and sulfur. A heterocyclyl radical may be attached at any endocyclic carbon which results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, pyranyl, piperazinyl, morpholinyl, thiamorpholinyl, thiamorpholinyl sulfone, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetrahydrofurofuranyl and tetrahydropyranofuranyl. A heterocycle may optionally be substituted with one or more substituents as described above for alkyl groups, although an endocyclic oxygen may not be substituted, and an endocyclic nitrogen atom may be substituted with hydrogen, $C_1$-$C_6$ alkyl, $C_3$-$C_6$ cycloalkyl, $C_2$-$C_6$ alkenyl, $C_2$-$C_6$ alkynyl, aryl, aminocarbonyl, $C_1$-$C_6$ alkylcarbonyl, arylcarbonyl, aryloxycarbonyl, $C_1$-$C_6$ alkoxycarbonyl, $C_1$-$C_6$ alkylsulfonyl, arylsulfonyl, or a heterocyclyl group. An "azacycle," as used herein, refers to an endocyclic-nitrogen-containing heterocycle as described above. Preferred azacycles include (without limitation) substituted or unsubstituted pyrrolidinyl, piperidinyl, piperazinyl, morpholino, azepinyl, quinuclidinyl (1-azabicyclo[2.2.2]octanyl) and tropanyl (8-methyl-8-azabicyclo[3.2.1]octanyl).

The term "halogen" refers to an atom selected from fluorine, chlorine, bromine, and iodine.

The term "amino," as used herein, refers to a moiety represented by the formula —$NR_{10}R_{11}$, in which $R_{10}$ and $R_{11}$ are each independently selected from the group consisting of hydrogen, $C_1$-$C_6$ alkyl, $C_3$-$C_6$ cycloalkyl, aryl, and a heterocyclyl moiety; or $R_{10}$ and $R_{11}$, together with the nitrogen atom to which they are both attached, form a 3-8 membered heterocyclic ring (which may be fused or bridged as described above for heterocyclyl moieties). Preferred amino groups include —$NH_2$, monoalkylamino (—$NHC_1$-$C_6$ alkyl), dialkylamino (—$N(C_1$-$C_6$ alkyl)$_2$), monoarylamino (—NH-aryl), arylalkylamino (—$N(aryl)(C_1$-$C_6$ alkyl)), and the like.

$R_{12}$ is selected from the group consisting of hydrogen, $C_1$-$C_6$ alkyl, and aryl. $R_{13}$ is selected from the group consisting of —C(O)—$C_1$-$C_6$ alkyl, —C(O)—$C_3$-$C_6$ cycloalkyl, —C(O)-aryl, —C(O)-heterocyclyl, —C(O)O—$C_1$-$C_6$ alkyl, —C(O)O—$C_3$-$C_6$ cycloalkyl, —C(O)O-aryl, —C(O)O-heterocyclyl, —C(O)-amino, —$SO_2$—$C_1$-$C_6$ alkyl, —$SO_2$—$C_3$-$C_6$ cycloalkyl —$SO_2$-aryl, and —$SO_2$-heterocyclyl.

Unless specifically indicated otherwise, the N-oxide form of any nitrogen atom is included in the compounds and methods of the invention.

I. Compounds of the Invention

In one aspect, the invention provides compounds represented by Formula I:

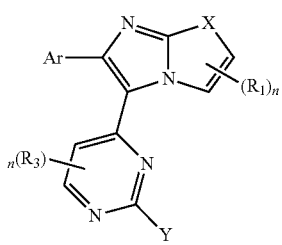

in which:

X is O or $S(O)_m$; Y is $OR_4$, or $NR_4R_5$; m is 0, 1, or 2; n is 1 or 2; $R_1$ is independently selected from the group consisting of hydrogen, —CN, —COOH, halogen, $C_1$-$C_6$ alkyl, $C_1$-$C_6$ alkoxy, $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; Ar is an aryl group; $R_3$ is independently selected from the group consisting of hydrogen, halogen, amino, $C_1$-$C_6$ alkyl, $C_1$-$C_6$ alkoxy, $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; $R_4$ and $R_5$ are each independently selected from the group consisting of hydrogen, $C_1$-$C_6$ alkyl, $C_3$-$C_6$ cycloalkyl, aryl, and heterocyclyl; or $R_4$ and $R_5$, taken together with the N atom to which they are attached, form a heterocyclic ring having from 3 to 8 atoms in the ring; or a salt (preferably a pharmaceutically acceptable salt) thereof;

with the proviso that: when X is $S(O)_m$, m is 0, Ar is phenyl, Y is $NR_4R_5$, $R_4$ is hydrogen and $R_5$ is alkyl, then if $R_5$ is a hydroxyalkyl group, $R_5$ 1) is not —$CH_2(CH_3)_2CH_2OH$, and 2) is not substituted at the carbon atom alpha to the N atom with a phenyl group (that is, the carbon atom of $R_5$ that is attached to the N atom of $NR_4R_5$ does not bear a phenyl group.

In preferred embodiments of Formula I, X is O or S, most preferably O. In preferred embodiments, Ar is phenyl or naphthyl, most preferably phenyl; in preferred embodiments, the phenyl group may be substituted with 1-3 halogen or trifluoromethyl substituents. A most preferred phenyl group is 4-fluorophenyl.

In additional preferred embodiments, Y is $NR_4R_5$, and preferably $R_4$ is hydrogen. In certain preferred embodiments, $R_5$ is selected from the group consisting of $C_2$-$C_6$ hydroxyalkyl, $C_2$-$C_6$ aminoalkyl, hydroxyaryl, aminoaryl, $C_3$-$C_6$ cycloalkyl and heterocyclyl, and still more preferably $R_5$ is $C_2$-$C_6$ hydroxyalkyl or a nitrogen-containing heterocycle (an azacycle), more preferably quinuclidin-3-yl.

In further preferred embodiments, $R_1$ and $R_3$ each represent H for all occurrences.

In other preferred embodiments, X is $S(O)_m$, and m is 0. In further preferred embodiments, Ar is phenyl or naphthyl, more preferably phenyl; in preferred embodiments, the phenyl group may be substituted with 1-3 halogen or trifluoromethyl substituents. A most preferred phenyl group is 4-fluorophenyl. In additional preferred embodiments, Y is $NR_4R_5$ and $R_4$ is hydrogen; $R_5$ is preferably a $C_2$-$C_6$ hydroxyalkyl group, a $C_2$-$C_6$ aminoalkyl group, a hydroxyaryl group, an aminoaryl group, or a nitrogen-containing heterocyclic ring having from 3 to 8 atoms in the ring, of which 1-3 atoms are nitrogen. In preferred embodiments, $R_1$ and $R_3$ are both hydrogen for all occurrences.

Compounds of Formula I can also include tracers, tags or labeling moieties, e.g., radioisotopes (such as tritium, carbon-14, or sulfur-35), fluorescent labels, and the like, which are known to one of ordinary skill in the art. Such labeled compounds can be used in methods for detecting or determining the presence of p38 in a cell or a tissue type.

In preferred embodiments, compounds of Formula I are selected to preserve the desired activity of the compounds (e.g., inhibition of cytokine activity, including inhibition of TNFα activity and IL-1 activity, or inhibition of p38 activity). Thus, substituents ($R_1$, $R_3$, $R_4$, Y, etc.) of a compound of Formula I should be selected to preserve such activity. Preservation of activity can be determined using in vivo and in vitro assays such as the assays described elsewhere in this specification.

For example, as described herein, preferred compounds of Formula I include compounds in which the group Ar is a phenyl or naphthyl group, more preferably substituted with at least one halogen moiety, preferably a fluorine atom, more preferably situated in the 4-position of the phenyl ring to which it is attached (relative to the attachment point for the phenyl ring to the imidazooxazole or imidazothiazole moiety).

In certain preferred embodiments, in a compound of Formula I, $R_3$ is hydrogen.

In preferred embodiments of the compounds of Formula I, Y is —$OR_4$ or —$NR_4R_5$, more preferably —$NR_4R_5$. In preferred embodiments, —$NR_4R_5$ represents —NH-hydroxyalkyl or —NH-heterocyclyl, in which the heterocyclyl moiety is a nitrogen-containing ring system having from 3 to 8 atoms in the ring system, and 1 to 3 atoms in the ring system are nitrogen atoms.

In other embodiments of Formula I, Y is —$NHR_7$, and $R_7$ is selected from the group consisting of —C(O)-alkyl, —C(O)-aryl, —C(O)O-alkyl, —C(O)O-aryl, —C(O)—$NR_8R_9$, —$S(O)_2$-alkyl, and —$S(O)_2$-aryl, in which $R_8$ and $R_9$ are each independently selected from hydrogen, alkyl, and aryl.

In general, structures depicted herein are meant to include all stereochemical forms of the structure, i.e., the R and S configurations for each asymmetric center, unless a particular stereochemistry is specifically indicated. Therefore, single stereochemical isomers (i.e., substantially pure enantiomers and diasteromers) as well as enantiomeric and diastereomeric mixtures, such as racemic mixtures, of the present compounds are within the scope of the invention. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated.

The present invention also includes compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the compounds of the invention. Examples of pharmaceutically-acceptable prodrug types contemplated by the present invention are described in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The compounds and compositions of the invention can also include metabolites. As used herein, the term "metabolite" means a product of metabolism of a compound of the invention or a pharmaceutically acceptable salt, analog, or derivative thereof, that exhibits a similar activity in vitro or in vivo to a compound of the invention.

The compounds and compositions of the invention can also include hydrates and solvates. As used herein, the term "solvate" refers to a complex formed by a solute (in this invention, a compound of Formula I and a solvent. Such solvents for the purpose of the invention preferably should not interfere with the biological activity of the solute. Solvents may be, by way of example, water, ethanol, or acetic acid.

II. Methods and Intermediates for Preparing Compounds of the Invention

Compounds of the invention can be prepared in a variety of ways, some of which are known in the art. For example, a method for synthesis of pyrimidyl-substituted imidazothiazoles has been described in PCT patent publication WO 03/00682. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$., John Wiley & Sons: New York, 1999 are useful and recognized reference textbooks of organic synthesis known to those in the art. The following descriptions of synthetic methods are designed to illustrate, but not limit, general procedures for the preparation of compounds of the invention.

In an embodiment, the invention includes intermediate compounds. For example, the present invention provides novel compounds represented by Formula II:

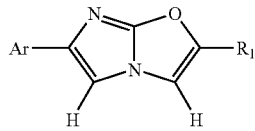

in which:

$R_1$ is selected from the group consisting of hydrogen, —CN, —COOH, halogen, $C_1$-$C_6$ alkyl, $C_1$-$C_6$ alkoxy, $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; and Ar is an aryl group; or a salt thereof. As the skilled artisan will recognize from the teachings herein, compounds of Formula II are useful, inter alia, for the synthesis of the imidazooxazole compounds of Formula I. For example, as shown in FIG. 1, compounds of Formula II, such as 4, can be reacted with an appropriate halopyrimidine compound (such as 5) under Heck reaction conditions, typically using a palladium catalyst (such as Pd(OAc)$_2$), to provide compounds of Formula I or precursors to such compounds. In preferred embodiments of compounds of Formula II, Ar is phenyl or naphthyl, most preferably phenyl; in certain preferred embodiments, the phenyl group is substituted, e.g., with 1-3 halogen, trifluoromethyl, or $C_1$-$C_6$ alkoxy substituents. In certain preferred embodiments, the phenyl group is selected from the group consisting of unsubstituted phenyl, 4-fluorophenyl, 3-methoxyphenyl, 4-methoxyphenyl, 3,4-difluorophenyl, 4-methylphenyl, 4-bromophenyl, 3-fluorophenyl, and 4-trifluoromethylphenyl. A most preferred phenyl group is 4-fluorophenyl. In preferred embodiments, $R_1$ is H. In a most preferred embodiment, $R_1$ is H and Ar is 4-fluorophenyl.

In yet another aspect, the invention provides compounds of Formula III:

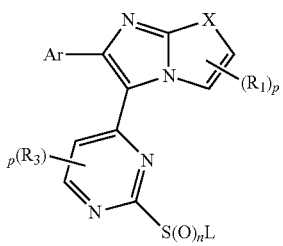

in which:

X is O or S(O)$_m$; m and n are each independently 0, 1, or 2; p is 1 or 2; $R_1$ is independently selected from the group consisting of hydrogen, —CN, —COOH, halogen, $C_1$-$C_6$ alkyl, $C_1$-$C_6$ alkoxy, $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; Ar is an aryl group; $R_3$ is independently selected from the group consisting of hydrogen, halogen, amino, $C_1$-$C_6$ alkyl, $C_1$-$C_6$ alkoxy, $C_3$-$C_6$ cycloalkyl, $C_3$-$C_6$ cycloalkyloxy, aryl, aminocarbonyl, $C_1$-$C_6$ alkylcarbonyl, and $C_1$-$C_6$ alkoxycarbonyl; and L is a $C_1$-$C_6$ alkyl group or an aryl group; or a salt thereof. Compounds of Formula III are useful, for example, for preparing additional compounds of Formula I, as described herein. For example, the group S(O)$_n$L in which n is 2 is generally a leaving group suitable for displacement by an nucleophile, including oxygen and nitrogen nucleophiles known in the art. For compounds of Formula II in which n is 0 or 1, oxidation of the thioalkyl sulfur atom can be accomplished, preferably in a selective manner, to provide compounds suitable for nucleophilic displacement. As described herein, Oxone™ is a preferred oxidant for this purpose. Salts forms of compounds of Formula III may include pharmaceutically-acceptable salts such as those described hereinbelow.

Compounds of Formula III can be prepared by the methods described herein, or by other methods that will be apparent to the ordinarily-skilled artisan. For example, as described herein, compounds of Formula III can be prepared by reaction of a compound of Formula II with a 4-halo-2-alkylthiopyrimidine under Heck conditions. The metal catalyst for the Heck reaction is typically a palladium catalyst, such as Pd(OAc)$_2$. Preferably, additives such as triphenyl phosphine or bases such as cesium carbonate can be used to facilitate the reaction.

In the reaction of a compound of Formula III with a nucleophile of the formula HOR$_4$ or HNR$_4$R$_5$, it is generally convenient to perform the reaction in the presence of a base to act as a proton sponge; hindered amine bases such as Hunig's base are useful for this purpose when an amine nucleophile is to be used for displacing the sulfone moiety of the compound of Formula III. Other hindered amine bases such as 2,6-lutidine may also be useful for this purpose. If oxygen nucleophiles are used for the displacement reaction, other bases, such as potassium carbonate (see, e.g., Example 3, infra), can be employed.

Figure 2:
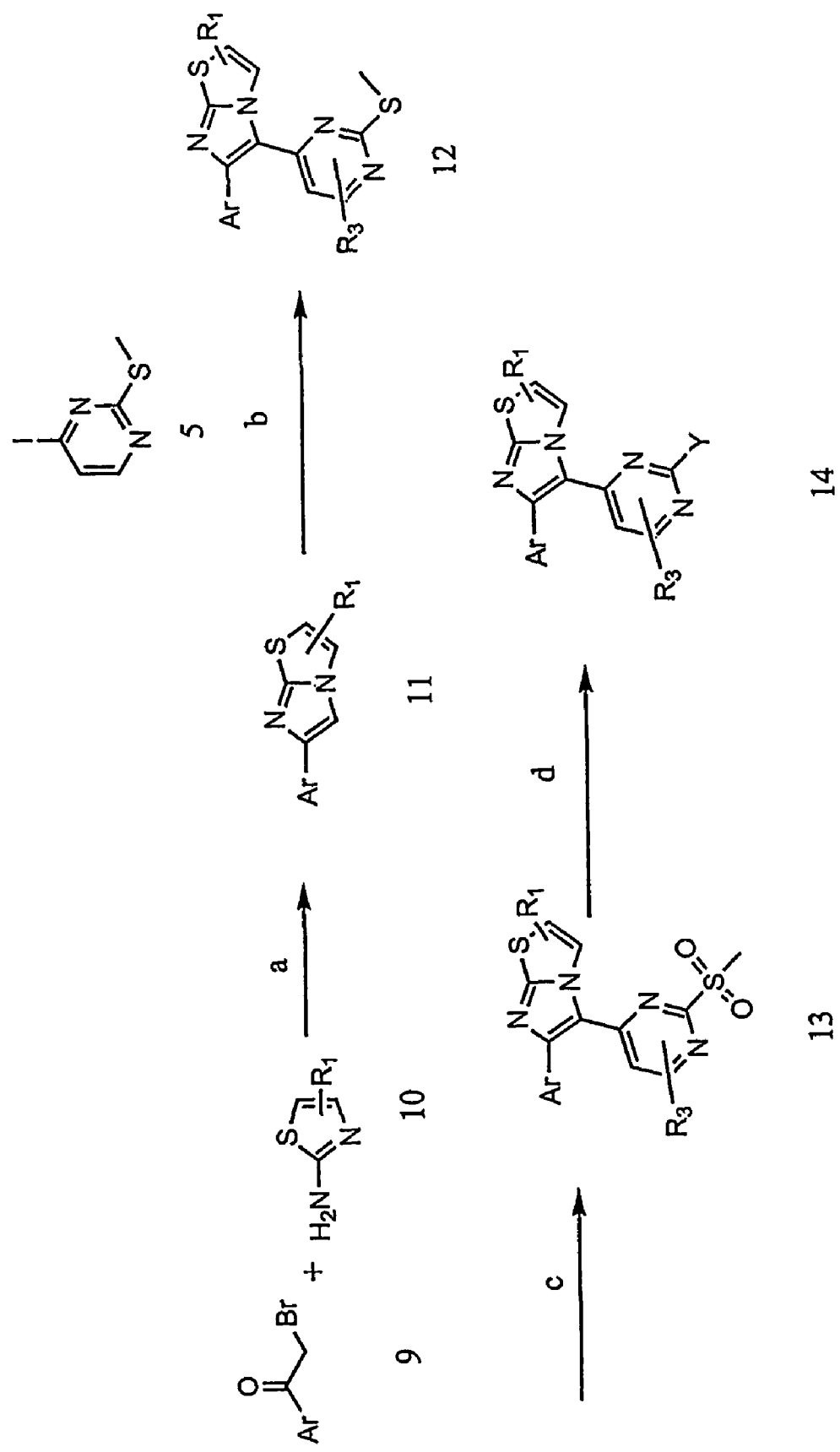
FIG. 2 illustrates one method for preparing imidazothiazole compounds of Formula I.
Figure 3:
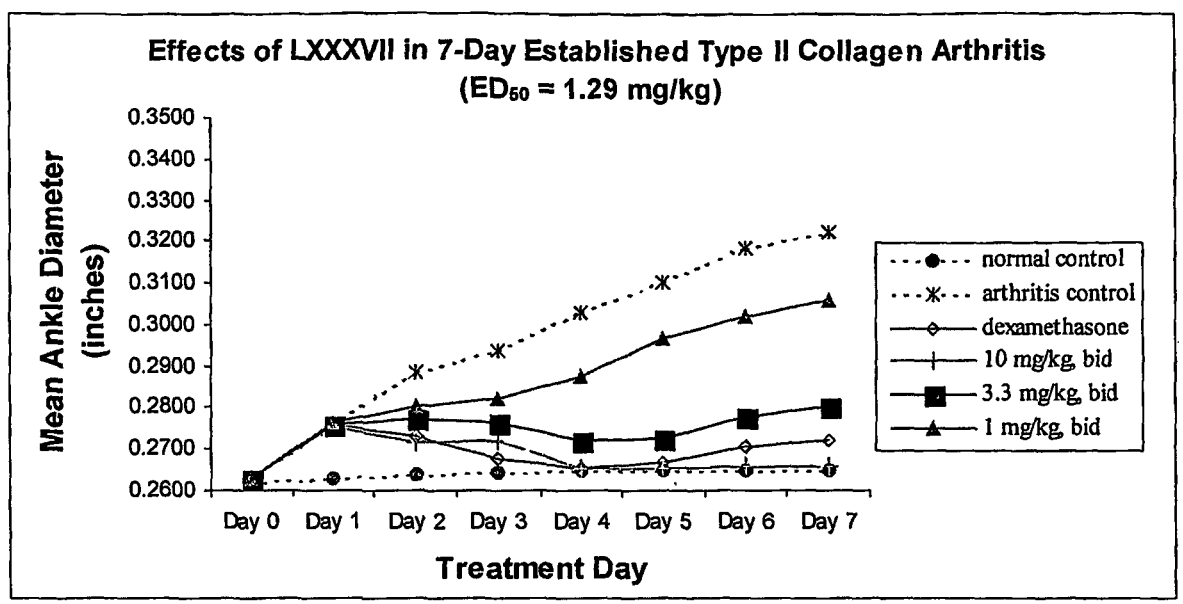
FIG. 3 illustrates mean increases in ankle diameter of rats upon treatment with compound LXXXVII.
Figure 4:
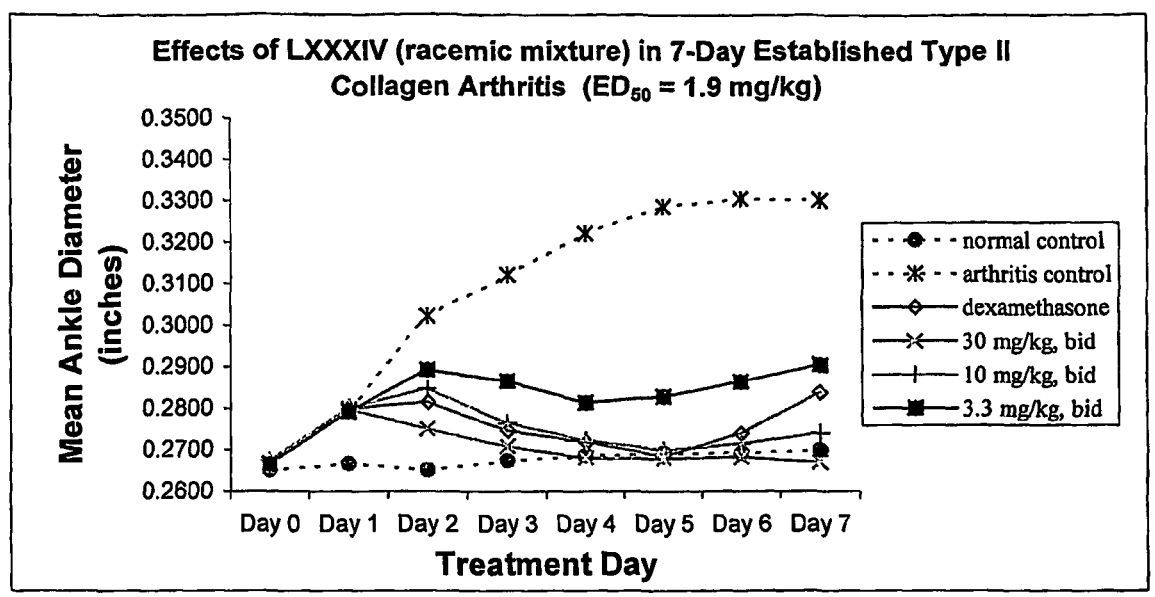
FIG. 4 illustrates mean increases in ankle diameter of rats upon treatment with compound LXXXIV.
Figure 5:
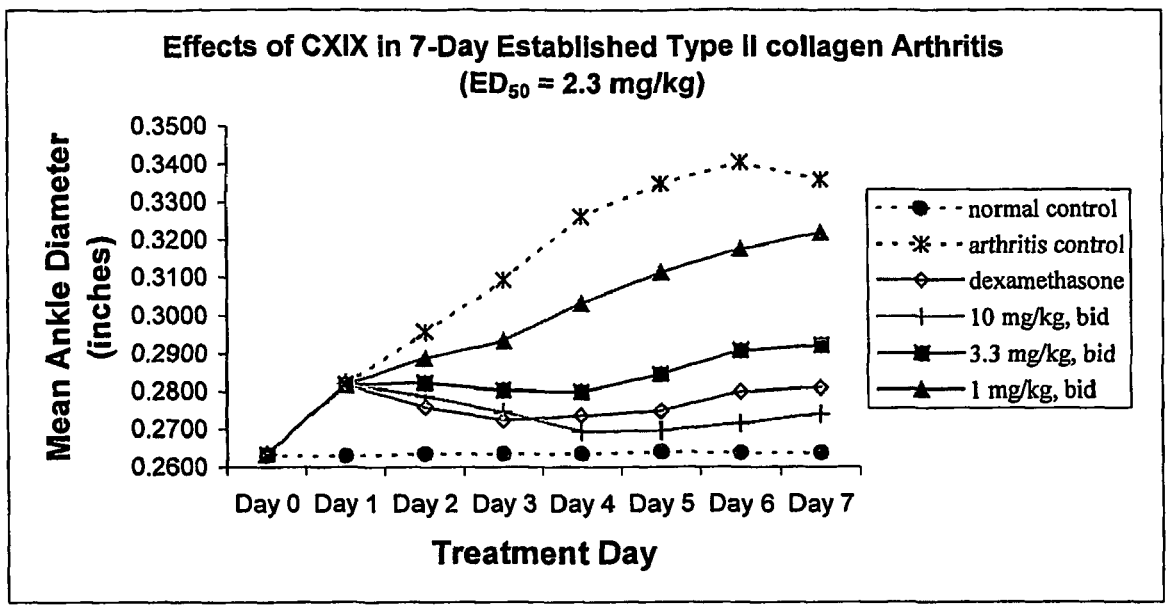
FIG. 5 illustrates mean increases in ankle diameter of rats upon treatment with compound CXIX.
Figure 6:
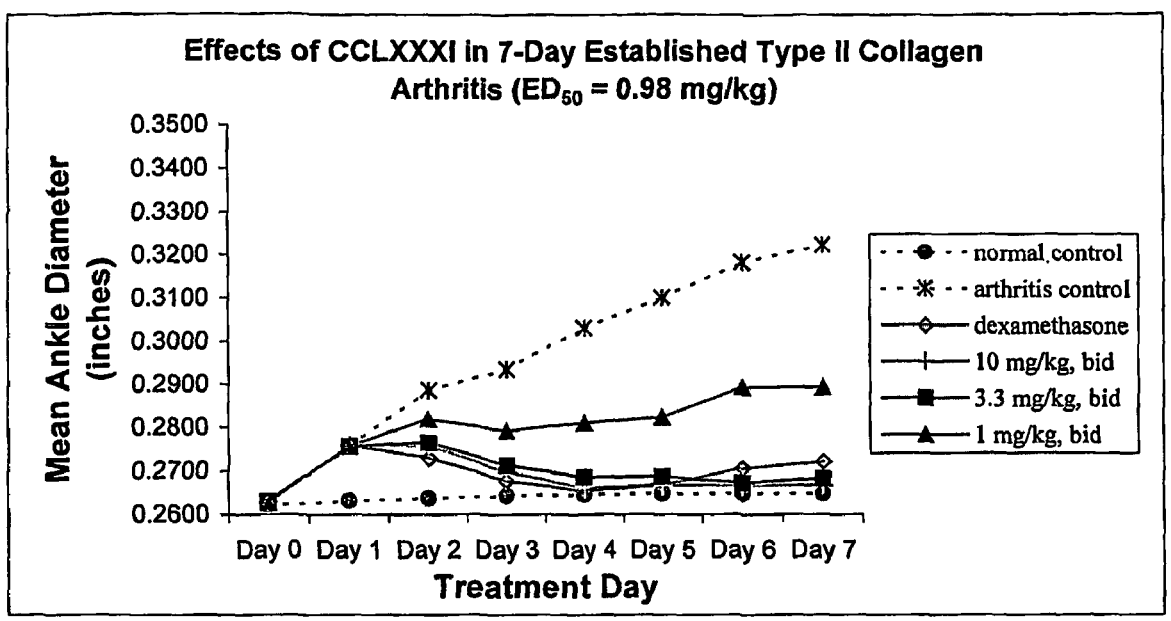
FIG. 6 illustrates mean increases in ankle diameter of rats upon treatment with compound CCLXXXI.
Figure 7:
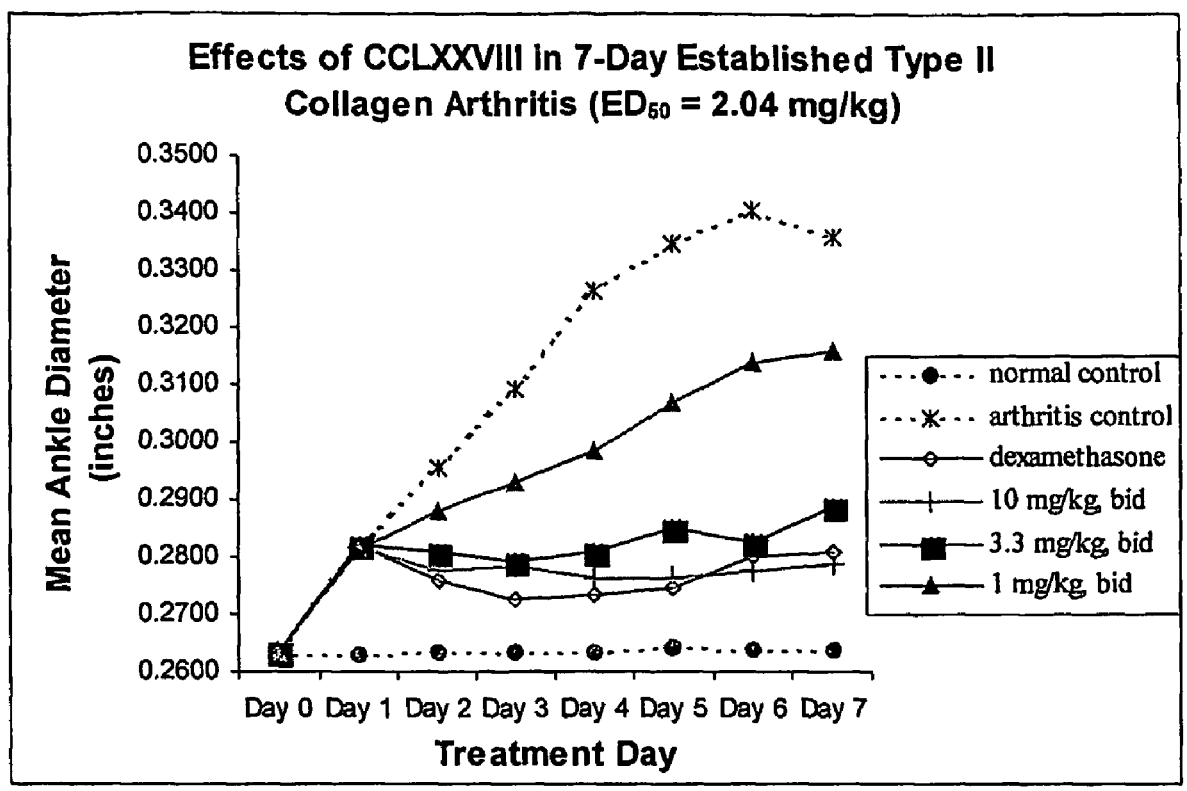
FIG. 7 illustrates mean increases in ankle diameter of rats upon treatment with compound CCLXXVIII.
Figure 8:
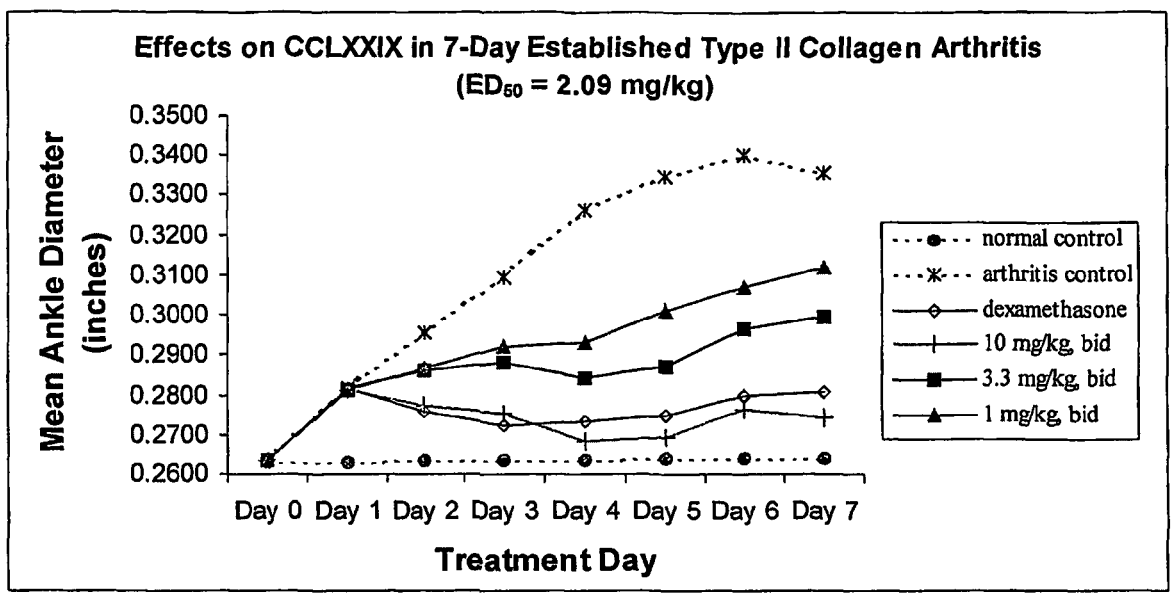
FIG. 8 illustrates mean increases in ankle diameter of rats upon treatment with compound CCLXXIX.
Figure 9:
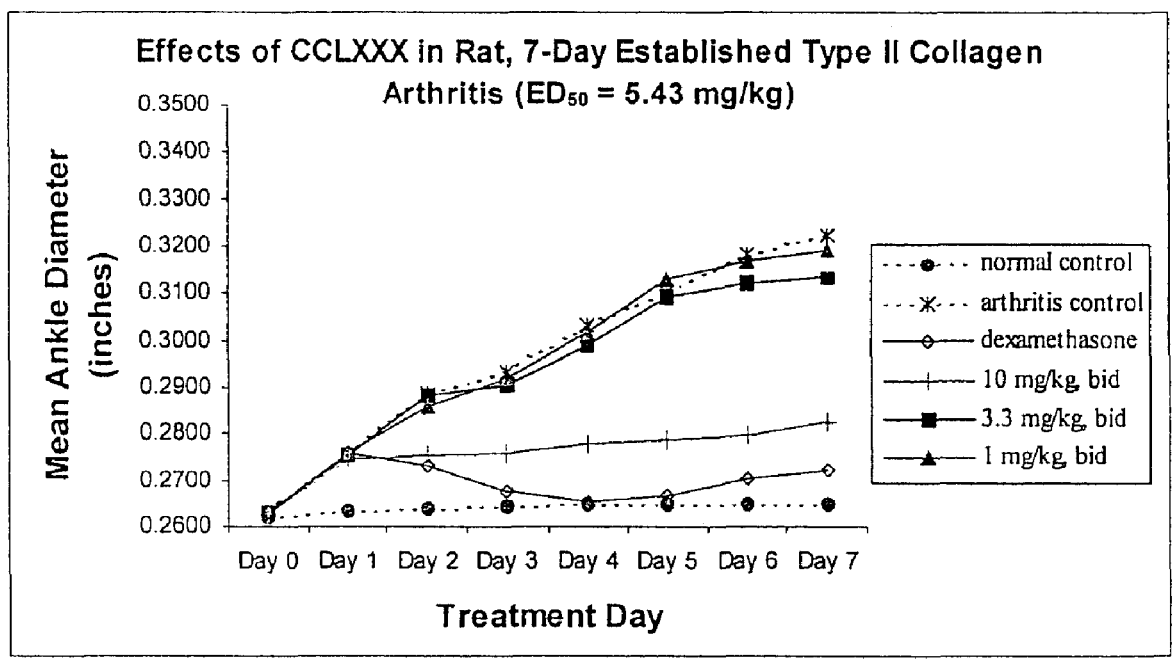
FIG. 9 illustrates mean increases in ankle diameter of rats upon treatment with compound CCLXXX.

In an embodiment, the invention provides methods for making compounds of Formula III. The method includes reacting a compound represented by Formula IV:

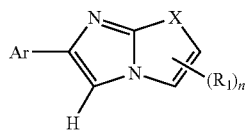

in which:

X is O or S(O)$_m$; m is 0, 1, or 2; n is 1 or 2; R$_1$ is independently selected from the group consisting of hydrogen, —CN, —COOH, halogen, C$_1$-C$_6$ alkyl, C$_1$-C$_6$ alkoxy, C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl; and Ar is an aryl group; or a salt thereof, with a compound represented by Formula V:

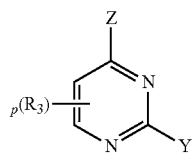

in which:

Z is selected from the group consisting of halogen, triflate, mesylate, or another suitable group; p is 1 or 2; R$_3$ is independently selected from the group consisting of hydrogen, halogen, amino, C$_1$-C$_6$ alkyl, C$_1$-C$_6$ alkoxy, C$_3$-C$_6$ cycloalkyl, C$_3$-C$_6$ cycloalkyloxy, aryl, aminocarbonyl, C$_1$-C$_6$ alkylcarbonyl, and C$_1$-C$_6$ alkoxycarbonyl; Y is S(O)$_n$L; n is 0, 1, or 2; and L is a C$_1$-C$_6$ alkyl group; or a salt thereof, in the presence of a metal catalyst and under conditions such that the compound of Formula III is formed, thereby preparing the compound of Formula III. The compounds of Formula IV can be prepared as described herein (e.g., as shown in FIGS. 1 and 2 and described in Examples 1 and 2), or may be prepared according to methods that are known or will be apparent to the skilled artisan in light of the teachings herein. In preferred embodiments of Formula IV, X is O; Ar is phenyl or naphthyl, most preferably phenyl; in certain preferred embodiments, the phenyl group is substituted, e.g., with 1-3 halogen, trifluoromethyl, or C$_1$-C$_6$ alkoxy substituents. In certain preferred embodiments, the phenyl group is selected from the group consisting of unsubstituted phenyl, 4-fluorophenyl, 3-methoxyphenyl, 4-methoxyphenyl, 3,4-difluorophenyl, 4-methylphenyl, 4-bromophenyl, 3-fluorophenyl, and 4-trifluoromethylphenyl. A most preferred phenyl group is 4-fluorophenyl. In preferred embodiments, R$_1$ is H for all occurrences. In a most preferred embodiment, X is O, R$_1$ is H and Ar is 4-fluorophenyl. Compounds of Formula V have been reported in the literature (e.g., 4-iodo-2-methylthio pyrimidine; see, e.g., PCT publication WO 02/04447 (2002)). Additional compounds of Formula V can be prepared by the skilled artisan in light of the teachings herein using no more than routine experimentation.

A method for preparing imidazooxazole compounds of the invention is described in the Examples below and illustrated in FIG. 1. In FIG. 1, step a, a suitably substituted α-haloketone 1 (in which Ar is an aryl moiety) is reacted with an optionally substituted 2-aminooxazole 2. This reaction is typically conducted in inert organic solvent such as acetonitrile or similar at room temperature. The product 3 is typically isolated from the reaction mixture as a solid hydrogen bromide salt by filtration. The cyclization of compound 3 to yield the imidazooxazole compound 4, indicated as step b in FIG. 1, is conveniently performed by the addition of a dehydrating regent, such as titanium tetrachloride, to the product from step a. This reaction, following appropriate pH modification of the resulting reaction mixture, provides 4. Coupling of 4 with a suitably substituted pyrimidine 5 to produce compound 6 is most frequently conducted with palladium catalysis as shown in step c of FIG. 1. Palladium catalysts suitable for Heck-type reactions are generally preferred. This reaction is typically carried out at elevated temperatures in anhydrous solvents, most conveniently dimethylformamide. A preferred pyrimidine reagent is 4-iodo-2-thiomethylpyrimidine, although other 4-halo-pyrimidines can be employed. Because the Heck-type reaction of compounds 4 and 5 to provide 6 does not always go to completion, a mixture of 4 and 6 may be taken through the next step together, with separation (and preferably recovery and recycling) of the unreacted starting material 4 at a later stage.

The oxidation step d (FIG. 1) can be conducted with a variety of standard oxidants known in the literature. One preferred method is to employ an aqueous solution of Oxone™ at room temperature. Displacement of the sulfone leaving group of 7 in step e with an oxygen or nitrogen nucleophile to provide additional compounds of the invention 8 (in which Y is a group as defined in Formula I) can be carried out using a number of standard procedures depending upon the nature of the new bond being created. In the case of amine nucleophiles, for instance, one preferred method is to conduct the reaction with a salt of a primary or secondary amine in a dimethylsulfoxide (DMSO) solution together with a hindered organic base, such as diisopropylethylamine, at an elevated temperature with shaking. Another preferred method is to use the amine free base in excess in hot dimethylsulfoxide with either shaking or stirring. The compounds 8 can then be isolated and purified using standard techniques. Further functionalization of compounds 8 can be performed, if desired. For example, deprotection to yield an unprotected compound can be performed as is routine to one of ordinary skill in the art (e.g., a protecting group such a t-butoxycarbonyl group can be removed from a protected amine to yield the unprotected amine). Alternatively, formation of amides or sulfonamides can be achieved by acylation of a primary or secondary amine (see, e.g., compounds CCLXXVIII and CCLXXIX of Table 1, prepared from compound CCLXXX).

An analogous method for preparing imidazothiazole compounds of the invention is shown in FIG. 2.

As shown in FIG. 2, step a, a suitably substituted α-haloketone 9 (in which Ar is an aryl moiety) is reacted with an optionally-substituted 2-aminothiazole 10 to yield the fused heterocycle 11. This reaction is typically conducted in inert organic solvent such as ethanol or the like, optionally at elevated temperatures. Coupling of 11 with a suitably substituted pyrimidine 5 to yield 12 is most frequently conducted with palladium catalysis as in step b, FIG. 2. This reaction is typically carried out at elevated temperatures in anhydrous solvents, most preferably dimethylformamide. A preferred pyrimidine reagent is 4-iodo-2-thiomethylpyrimidine, although other halopyrimidines may be employed. The thiomethyl group of 12 can be oxidized in step c to provide a sulfone group suitable for displacement reaction in step d. The oxidation step c can be conducted with a variety of standard oxidants known in the literature. A preferred method is to employ an aqueous solution of Oxone™ at room temperature, which advantageously does not cause excessive oxidation of the imidazothiazole sulfur atom. Displacement of the leaving group of 13 in step d with an oxygen or nitrogen nucleophile to provide additional compounds of the invention 14 (in which Y is a group as defined in Formula I) can be carried out using a number of standard procedures depending upon the nature of the new bond being created. In the case of amine nucleophiles, for instance, one preferred method is to conduct the reaction of 13 with a salt of a primary or secondary amine, in a dimethylsulfoxide solution together with a hindered organic base, such as diisopropylethylamine, at an elevated temperature with shaking. Another preferred method is to use the amine free base in excess in hot dimethylsulfoxide with either shaking or stirring. As described above, further functionalization of products 14 can then be performed if desired.

III. Therapeutic and Diagnostic Methods of the Invention

In another aspect, the invention provides methods for treating disease conditions associated with (e.g., mediated directly or indirectly by) p38 or one or more cytokines. For example, in a preferred embodiment, the methods include administering to a subject in need of treatment (e.g., a mammal in need of such treatment) a therapeutically or prophylactically effective amount of a compound of the invention. The compound of the invention is preferably a compound of Formula I. Alternatively, the compound may be a compound of Formula II, Formula III, Formula IV, or Formula V, or any combination thereof. A subject may include one or more cells or tissues, or organisms. A preferred subject is a mammal. A mammal may include any mammal. As a non-limiting example, preferred mammals include cattle, pigs, sheep, goats, horses, camels, buffalo, cats, dogs, rats, mice, and humans. A highly preferred subject mammal is a human.

According to the methods of the invention, the compound (s) may be administered to the subject via any drug delivery route known in the art. Specific exemplary administration routes include oral, ocular, rectal, buccal, topical, nasal, ophthalmic, subcutaneous, intramuscular, intraveneous (bolus and infusion), intracerebral, transdermal, and pulmonary.

In one embodiment, the invention provides methods for treating disease conditions in which p38 activity contributes to the disease phenotype. The method includes administering a therapeutically or prophylactically effective amount of a compound of the invention to a subject in need thereof. Again, the compound of the invention is preferably a compound of Formula I. Alternatively, the compound may be a compound of Formula II, Formula III, Formula IV, or Formula V, or any combination thereof.

The term "p38-associated condition" means a disease or other deleterious condition in which the p38 MAP kinase signaling pathway is implicated, whether directly or indirectly. This includes, but is not limited to, conditions caused by IL-1, TNFα, IL-6 or IL-8 dysregulation or overexpression resulting from sustained, prolonged, enhanced or elevated levels of p38 activity. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with the prostaglandin or cyclooxygenase pathways, e.g., conditions involving prostaglandin endoperoxide synthase-2. A p38-associated condition can include any condition associated with or mediated by an isoform of p38. In a preferred embodiment, the p38-associated condition is a condition associated with p38α.

The term "modulating p38 activity" means increasing or decreasing p38 activity, whether in vitro or in vivo. Modulating p38 activity preferably means decreasing (inhibiting) p38 activity. In certain preferred embodiments, p38 activity in a cell is inhibited by at least 20%, more preferably at least 30%, 40%, 50%, 80%, 90%, 95%, or 99% compared to the p38 activity of an untreated control cell. In preferred embodiments, p38 activity in a cell (or tissue) is restored to a normal range for the cell (or tissue) type upon treatment according to the methods of the invention.

In another embodiment, the invention provides methods for treating disease conditions associated with a cytokine or cytokines. The method includes administering a therapeutically or prophylactically effective amount of a compound of the invention to a subject in need thereof. Again, the compound of the invention is preferably a compound of Formula I. Alternatively, the compound may be a compound of Formula II, Formula III, Formula IV, or Formula V, or any combination thereof. In a preferred embodiment, at least one of the cytokine or cytokines is preferably selected from the group consisting of IL-1, IL-6, IL-8, and TNFα. In a more preferred embodiment, all of the cytokine or cytokines are selected from the group consisting of IL-1, IL-6, IL-8, and TNFα. By way of non-limiting example, the methods include administering to a subject in need of treatment (e.g., a mammal in need of such treatment) an effective amount of a compound of the invention. A subject may include one or more cells or tissues, or organisms. A preferred subject is a mammal. A mammal may include any mammal. As a non-limiting example, preferred mammals include cattle, pigs, sheep, goats, horses, camels, buffalo, cats, dogs, rats, mice, and humans. A highly preferred subject mammal is a human.

A condition associated with altered cytokine activity, as used herein, refers to a condition in which cytokine activity is altered compared to a non-diseased state. This includes, but is not limited to, conditions caused by IL-1, TNFα, IL-6 or IL-8 overproduction or dysregulation resulting in sustained, prolonged, enhanced or elevated levels of cytokine activity, which may be associated with p38 activity. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with the cyclooxygenase and lipoxygenase signaling pathways, such as prostaglandin endoperoxide synthase-2. A cytokine-associated condition can include any condition associated with or mediated by IL-1 (particularly IL-1β), TNFα, IL-6 or IL-8, or any other cytokine which can be regulated by p38. In preferred embodiments, the cytokine-associated condition is a condition associated with TNFα.

The terms "therapeutically effective amount" and "prophylactically effective amount", as used herein, refer to an amount of a compound of the invention sufficient to treat, ameliorate, or prevent the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the initial target plasma concentration may range from approximately 5 μg/mL to approximately 100 μg/mL, preferably from approximately 10 μg/mL to approximately 100 μg/mL, more preferably from approximately 20 μg/mL to approximately 100 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The inventive methods can also be used to treat autoimmune diseases and diseases associated with acute and chronic inflammation. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; chronic obstructive pulmonary disease; chronic pulmonary inflammation; inflammatory bowel disease; Crohn's disease; psoriasis; eczema; ulcerative colitis; glomerular nephritis; scleroderma; chronic thyroiditis; Grave's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as Multiple Sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the invention can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation. In addition, compounds of the invention may be useful for treatment of protozoal diseases in animals, including mammals.

In an embodiment, the methods of the invention can be used to treat humans or non-human animals, preferably mammals. Mammals that can be treated include, without limitation, cattle, pigs, sheep, goats, horses, camels, buffalo, cats, dogs, rats, and mice.

It will be appreciated that treatment according to the invention includes preventing a disease, ameliorating symptoms, slowing disease progression, reversing damage, or curing a disease.

In one aspect, treating a disease condition associated with p38 or one or more cytokines results in an increase in average survival time of a population of treated subjects in comparison to a population of untreated subjects. Preferably, the average survival time is increased by more than 30 days; more preferably, by more than 60 days; more preferably, by more than 90 days; and even more preferably by more than 120 days. An increase in survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating a disease condition associated with p38 or one or more cytokines results in a decrease in the mortality rate of a population of treated subjects in comparison to a population of subjects receiving carrier alone. In another aspect, treating a disease condition associated with p38 or one or more cytokines results in a decrease in the mortality rate of a population of treated subjects in comparison to an untreated population. In a further aspect, treating a disease condition associated with p38 or one or more cytokines results a decrease in the mortality rate of a population of treated subjects in comparison to a population receiving monotherapy with a drug that is not a compound of the present invention, or a pharmaceutically acceptable salt, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating a disease condition associated with p38 or one or more cytokines results in a decrease in growth rate of a tumor. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating a disease condition associated with p38 or one or more cytokines results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating a disease condition associated with p38 or one or more cytokines results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating a disease condition associated with p38 or one or more cytokines results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating a disease condition associated with p38 or one or more cytokines results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

The methods of the present invention may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification.

As described elsewhere herein, the compounds of the invention may be formulated in pharmaceutical compositions, if desired, and can be administered by any route that permits treatment of the disease or condition. A preferred route of administration is oral administration. Administration may take the form of single dose administration, or the compound of the invention can be administered over a period of time, either in divided doses or in a continuous-release formulation or administration method (e.g., a pump). However the compounds of the invention are administered to the subject, the amounts of compound administered and the route of administration chosen should be selected to permit efficacious treatment of the disease condition.

The methods of the invention also include the use of a compound or compounds of the invention together with one or more additional therapeutic agents for the treatment of disease conditions. Thus, for example, in certain embodiments, the invention provides the use of a compound of the invention, or a pharmaceutically acceptable salt or solvate thereof, in combination with other pharmaceutically active agents in the treatment of disease. Pharmaceutically active agents include any pharmaceutical agents that are useful for the treatment of any disease condition. In one non-limiting example, the compounds of the invention are pharmaceutically active agents that can be combined with other pharmaceutically active agents for the treatment of rheumatoid arthritis. Such other pharmaceutically active agents include, but are not limited to: matrix metalloprotease inhibitors and other DMARDs (disease-modifying anti-rheumatic drugs) such as methotrexate, sulfasalazine, hydroxychloroquine, penicillamine, cyclosporin A, gold sodium thiomalate, auroanofin and aurothioglucose; CD8 antagonists; anti-TNFα agents; immunosuppressants and NSAIDs (non-steroidal anti-inflammatories). For treatment of other disease conditions, any additional active agents may be used, as will be apparent to the skilled artisan.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In an embodiment of the present invention, methods are provided for inhibiting the activity of p38 in a cell, in vitro or in vivo. The methods include contacting a cell or tissue containing p38 with an effective p38-inhibiting amount of a compound of the invention, under conditions such that p38 activity in the cell or tissue is inhibited. Contacting a cell refers to a condition in which a compound or other composition of matter is in direct contact with a cell or tissue, or is close enough to induce a desired biological effect in a cell or tissue. For example, contacting a cell or tissue containing p38 with a compound of the invention may be conducted by any means that permits an interaction between p38 and the compound of the invention, resulting in the desired biological effect in a cell. Contacting a cell or tissue may be accomplished, for example, by introduction of a compound of the invention such as a Formula I compound, prodrug or intermediate. Contacting a cell or tissue may be accomplished by introduction of a pharmaceutical composition. Contacting a cell or tissue may be accomplished by direct introduction of the active compound to the cell or tissue containing p38. Alternatively, for example, contacting a cell or tissue may be accomplished by introducing a compound in a manner that the compound will be targeted, directly or indirectly, to a cell or tissue containing p38. Contacting a cell or tissue may be accomplished under conditions such that a compound of the invention, preferably Formula I, can bind to p38 protein. Such conditions may include proximity of the compound and p38-containing cell or tissue, pH, temperature, or any condition that affects the binding of a compound of the invention to p38 protein.

In another aspect, the invention provides a method for modulating p38 activity in a cell or secreted by a cell. The method includes contacting a cell containing p38 with an effective p38-inhibiting amount of a compound of the invention, under conditions such that p38 activity in the cell is modulated (more preferably, inhibited). In certain embodiments, the cell is contacted with the compound of the invention in vitro; in other embodiments, the cell is contacted with the compound of the invention in vivo. In certain embodiments, the compound of the invention is provided in the form of a pharmaceutical composition, together with a pharmaceutically acceptable carrier.

In another aspect, the invention provides a method for modulating cytokine activity or levels in a cell. The method includes contacting a cell containing cytokines with an effective cytokine-inhibiting amount of a compound of the invention, under conditions such that cytokine activity or levels in the cell are modulated (more preferably, inhibited). In certain embodiments, the cell is contacted with the compound of the invention in vitro; in other embodiments, the cell is contacted with the compound of the invention in vivo. In certain embodiments, the compound of the invention is provided in the form of a pharmaceutical composition, together with a pharmaceutically acceptable carrier.

In another aspect, the invention provides methods for determining whether a compound of Formula I is potentially useful as a therapeutic agent for the treatment of p38- or cytokine-associated conditions. In some embodiments, the methods comprise contacting p38 with a compound of the invention, and determining whether the compound of the invention modulates (preferably, inhibits) the activity of p38. In some embodiments, the methods comprise contacting p38 with a compound of the invention, and determining whether the compound of the invention modulates (preferably, inhibits) the activity of cytokines. In preferred embodiments, the contacting step takes place in vitro; in certain preferred embodiments, the contacting step comprises contacting a cell comprising p38 with a compound of Formula I.

The methods of the invention have many uses. For example, methods of inhibiting p38 activity in vitro may be useful, e.g., in developing screening assays (e.g., as a positive control), or as a research or diagnostic tool for studying the role of p38 in cellular function (e.g., inhibiting p38 to determine the effect of such inhibition on other functions in the cell). Especially useful for this purpose are compounds of the invention in which the compounds contain a label or tag such as a radioisotope or a fluorescent label. Such labeled compounds can be used in methods for detecting or determining the presence, activity or distribution of p38 in a cell or a tissue type, e.g., by contacting a cell or tissue with a labeled compound of the invention, and then detecting the presence or absence of the label in the cell or tissue.

Accordingly, diagnostic tests are contemplated as part of the present invention. For example, a tissue biopsy sample can be taken from a subject suffering from a p38-associated or cytokine-associated condition. The biopsy sample can be tested to determine the level of p38 activity (or cytokine levels) present in the sample; the sample can then be contacted with a compound of the invention, and the p38 activity (or cytokine levels) measured to determine whether the compound of Formula I has a desired effect (e.g., inhibition of p38 or cytokine activity). Such a test could be used to determine whether treatment with a compound of the invention is likely to be effective in that subject. Alternatively, the sample could be contacted with a labeled compound of the invention (e.g., a fluorescently-labeled compound) and the sample then examined (e.g., under a confocal microscope) to determine the distribution of p38 in the tissue sample. Repeated biopsy samples taken during a course of treatment could also be used to study the efficacy of the treatment. Other diagnostic tests using the compounds of the invention will be apparent to one of ordinary skill in the art in light of the teachings of this specification.

Thus, for example, the invention provides methods for determining the presence, location, or quantity, or any combination thereof of p38 protein in a cell or tissue sample. The methods include a) contacting the cell or tissue sample with a compound of the invention under conditions such that the compound can bind to p38 protein; and b) determining the presence, location, or quantity, or any combination thereof of the compound of the invention in the cell or tissue sample, thereby determining the presence, location, or quantity, or any combination thereof of p38 protein in the cell or tissue sample. Determining the presence, location, or quantity, or any combination thereof of the compound of the invention in the cell or tissue sample may be conducted by any means that reveals the presence, location, or quantity, or any combination thereof of the compound in the cell or tissue. For example, as described previously, radioactive or fluorescent labeling methods may be used. Additional methods of determining the presence, location, or quantity, or any combination thereof of a compound of the invention will be apparent to a skilled artisan.

In another embodiment, the invention provides methods for determining (1) whether a compound of the invention will be a useful therapeutic agent for treatment of a subject suffering from a p38-associated condition, or (2) the severity of disease or (3) the course of disease during treatment with a disease-modifying agent. The methods include: a) obtaining a cell or tissue sample from the subject before, during and after termination of treatment with a compound of the invention or another disease-modifying agent; b) contacting the sample with a compound of the invention; and c) determining the amount of the compound of the invention that binds to the sample, wherein binding to p38 protein by the compound is related to the amount of p38 protein in the sample.

In another embodiment, the invention provides methods for determining (1) whether a compound of the invention will be a useful therapeutic agent for treatment of a subject suffering from a cytokine-associated condition, or (2) the severity of disease or (3) the course of disease during treatment with a disease-modifying agent. The methods include: a) obtaining a cell or tissue sample from the subject before, during and after termination of treatment with a compound of the invention or another disease-modifying agent; b) contacting the sample with a compound of the invention and c) determining the amount of the compound of the invention that binds to the sample, wherein binding to p38 protein by the compound is related to the amount of p38 protein in the sample, and the amount of p38 in the sample is related to the quantity of cytokines released. In an exemplary embodiment, such a method may be conducted by obtaining cells from a cancer cell line, contacting cells from the cancer cell line, such as, for example, cells from a metastatic breast carcinoma, colorectal carcinoma, malignant melanoma, gastric cancer, or non-small cell lung cancer line with a compound of the present invention and determining the binding.

IV. Pharmaceutical Compositions

While it is possible for the compounds of the present invention to be administered neat, it may be preferable to formulate the compounds as pharmaceutical compositions. As such, in yet another aspect of the invention, pharmaceutical compositions useful in the methods of the invention are provided. More particularly, the pharmaceutical compositions of the invention may be useful, inter alia, for treating conditions associated with p38 activity or cytokine activity or any combination thereof. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. A preferred subject is a mammal. A mammal includes any mammal, such as by way of non-limiting example, cattle, pigs, sheep, goats, horses, camels, buffalo, cats, dogs, rats, mice, and humans. A highly preferred subject mammal is a human.

The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment or prevention of bacterial infection (e.g., anti-bacterial or anti-microbial agents).

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition of the invention, a pharmaceutically acceptable salt of a compound of the invention may be dissolved in an aqueous solution of an organic or inorganic acid, such as 0.3 M solution of succinic acid, or more preferably, citric acid. If a soluble salt form is not available, the compound of formula (I) may be dissolved in a suitable co-solvent or combination of co-solvents. Examples of suitable co-solvents include alcohol, propylene glycol, polyethylene glycol 300, polysorbate 80, glycerin and the like in concentrations ranging from 0 to 60% of the total volume. In one embodiment, the active compound of Formula I is dissolved in DMSO and diluted with water. The pharmaceutical composition may also be in the form of a solution of a salt form of the active ingredient in an appropriate aqueous vehicle, such as water or isotonic saline or dextrose solution. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-β-cyclodextrin and even more preferably from 2.5% to 10% hydroxypropyl-β-cyclodextrin. The amount of solubility enhancer employed will depend on the amount of the compound of the present invention in the composition.

A pharmaceutical composition contains a total amount of the active ingredient(s) sufficient to achieve an intended therapeutic effect. More specifically, in some embodiments, the pharmaceutical composition contains a therapeutically effective amount (i.e., an amount of a p38-inhibiting compound of the invention that is effective in the prevention or treatment of the existing symptoms of a disease or condition associated with or mediated directly or indirectly by p38). In certain embodiments, the pharmaceutical composition contains a therapeutically effective amount (i.e., an amount effective to prevent development of or to alleviate the existing symptoms of a disease or condition associated with a cytokine or cytokines, such as, but not limited to, IL-1, IL-6, IL-8 and TNFα) of a cytokine-inhibiting compound of the invention. The total amounts of the compound of the invention that may be combined with the carrier materials to produce a unitary dosing form will vary depending upon the host treated and the particular mode of administration. Preferably, the compositions are formulated so that a dose of between 0.01 to 100 mg/kg body weight/day of a p38-inhibiting agent is administered to a patient receiving the compositions.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. The following examples describe in detail the chemical synthesis of representative compounds of the present invention. The procedures are illustrations, and the invention should not be construed as being limited by the chemical reactions and conditions they express. No attempt has been made to optimize the yields obtained in these reactions, and it would be obvious to one skilled in the art that variations in reaction times, temperatures, solvents, and/or reagents could increase the yields.

Example 1

Preparation of 3-({4-[6-(4-fluorophenyl)imidazo[2,1-b][1,3]oxazol-5-yl]pyrimidin-2-yl}amino)-2,2-dimethylpropan-1-ol A compound of the invention represented by Formula I (in which X is O) was prepared according to the following representative method.

Commercially-available compounds were used as received unless otherwise stated.

Step 1

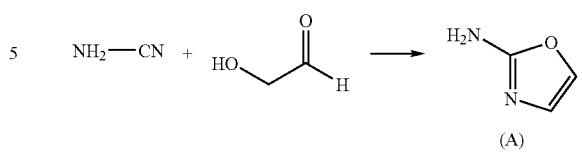

(A)

2-Amino-oxazole

To a solution of cyanamide (33 ml, 50% wt in water, 0.416 mol) in THF (100 ml), was added an aqueous solution of 2-hydroxyacetaldehyde (25 g, 0.416 mol) in water (40 ml), followed by the dropwise addition of 2M sodium hydroxide (42 ml, 0.083 mol) at 0° C. Stirring was continued for a total of 24 hours. Then, the reaction mixture was concentrated in vacuo to remove most of the THF. The remaining water layer was extracted with ethyl acetate (4×200 ml). The extract was dried over sodium sulfate and the solvent was evaporated in vacuo. This gave the white solid product A (23 g, 66%).

Step 2:

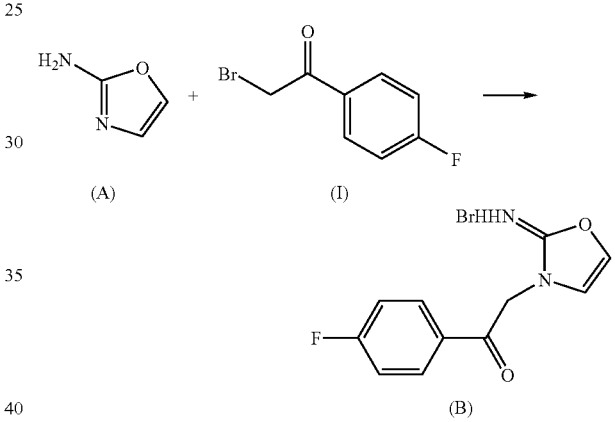

To a solution of 2-bromo-1-(4-fluorophenyl)-ethanone (CAS# 403-29-2, I) (60 g, 0.376 mol) in anhydrous tetrahydrofuran (THF) solution (200 ml) was added over 20 minutes a solution of 2-amino-oxazole (A) (16 g, 0.19 mol) in anhydrous acetonitrile at room temperature. The mixture was stirred for 24 hours before cooling to 0° C. The precipitate was collected by filtration and washed with cold acetonitrile (3×30 mL) and dried in a vacuum oven to yield light yellow crystals of 1-(4-fluorophenyl)-2-(2-imino-1,3-oxazol-3(2H)-yl)ethanone hydrobromide (B) (42.0 g, 77%). MS (ES+) 203 (M+1).

$^1$H NMR (300 MHz, DMSO) δ: 7.95 (brs, 1H), 9.7 (brs, 1H), 8.14 (m, 2H), 7.99 (d, J=0.9, 1H), 7.61 (d, J=1.5 Hz, 1H), 7.51 (t, J=8.7 Hz, 2H), 5.79 (s, 2H).

Step 3:

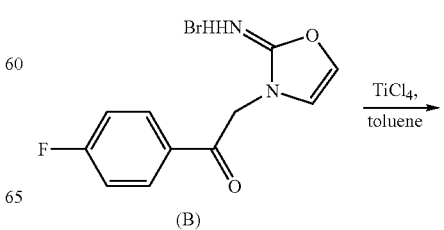

(B)

-continued

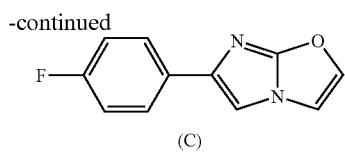

(C)

1-(4-Fluorophenyl)-2-(2-imino-1,3-oxazol-3(2H)-yl) ethanone hydrobromide (B) (13.0 g, 43.0 mmol) was suspended in anhydrous toluene (100 mL) and stirred in an ice bath at −10° C.

Titanium tetrachloride (24 mL, 0.225 mol) was added drop-wise over 20 minutes. After addition was complete the mixture was allowed to stir at 0° C. for 1 hour before heating at 110° C. for 5 hours. The reaction mixture was allowed to cool to room temperature, the excess toluene was decanted and ice water (200 mL) was added. After vigorously stirring for 1 hour the mixture was treated with sodium carbonate and stirring continued for 30 minutes. Ethyl acetate (100 mL) was added to the mixture and stirring continued for an additional hour. The organic phase was removed and the aqueous residue extracted with ethyl acetate (3×100 mL). The combined organic phase was dried over anhydrous sodium sulfate, filtered and concentrated in vacuo to provide the title compound (8.0 g, 92%).

MS (ES+) 203 (M+1);
$^1$H NMR (300 MHz, DMSO) δ: 7.95 (brs, 1H), 7.92 (brs, 1H), 7.79 (m, 2H), 7.74 (d, J=8.4, 1H), 7.19 (m, 2H).

Step 4:

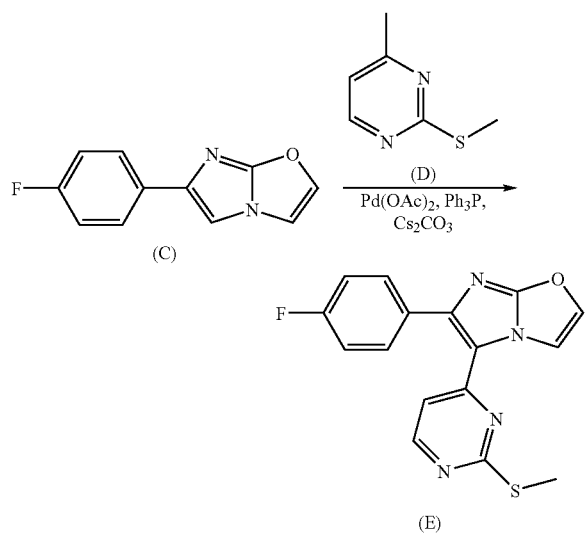

To a solution of 6-(4-fluorophenyl)imidazo[2,1-b][1,3]oxazole (C) (1 g, 4.9 mmol) and 4-iodo-2-thiomethylpyrimidine (D) (2.49 g, 9.8 mmol) in degassed dimethylformamide (10 mL) under argon is added Pd(OAc)$_2$ (0.222 g, 0.9 mmol) and triphenylphosphine (0.518 g, 1.9 mmol) sequentially. Cesium carbonate (2.41 g, 7.4 mmol) is added to the mixture and the reaction vessel flushed with argon and sealed. The reaction mixture is heated at 80° C. for 15 hours with vigorous magnetic stirring. The viscous slurry is cooled to room temperature and filtered through a bed of Celite on top of silica gel. The residue is washed with ethyl acetate (3×10 mL) and filtered. The filtrate is washed with water (2×100 ml). The organic phase is dried over anhydrous magnesium sulfate, filtered and the solvent removed in vacuo. The residue is purified by silica gel column chromatography to provide 6-(4-fluorophenyl)-5-[2-(methylsulfanyl)pyrimidin-4-yl] imidazo[2,1-b][1,3]oxazole (E) (Compound X, Table 1) as a light yellow solid (0.474 g, 30%), m.p. 144-145° C.;

$^1$H NMR (300 MHz CDCl$_3$) δ: 8.2 (d, 1H), 8.1 (s, 1H), 7.6 (t, 2H), 7.4 (s, 1H), 7.1 (t, 2H), 6.8 (d, 1H), 2.6 (s, 3H).

$^{13}$C NMR (300 MHz in CDCl$_3$): 172.3, 164.5, 161.2, 156.1, 155.8, 147.0, 137.6, 130.9, 130.8, 130.4, 116.0, 115.8, 115.5, 114.7, 110.5, and 14.2.

Step 5:

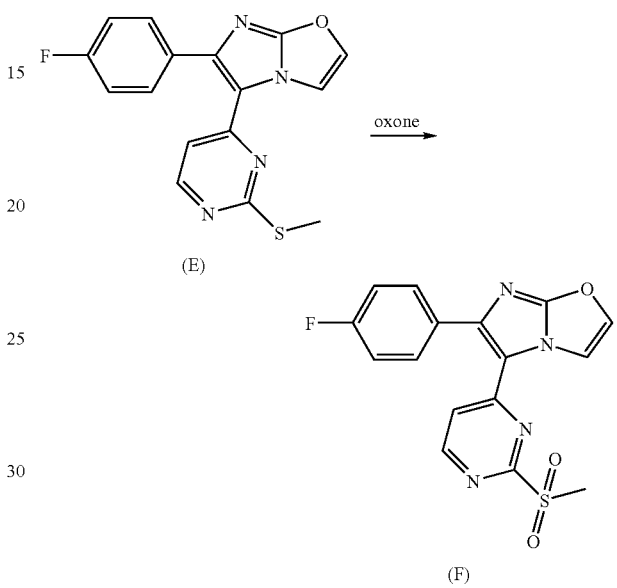

To a solution of 6-(4-fluorophenyl)-5-[2-(methylsulfanyl) pyrimidin-4-yl]imidazo[2,1-b][1,3]oxazole (E) (2.0 g, 6.13 mmol) in methanol (250 mL) is slowly added Oxone™ (potassium monopersulfate) (11.3 g, 18.4 mmol) in water (50 mL). The mixture is stirred at room temperature for 24 hours. The solvent is removed in vacuo and the residue dissolved in dichloromethane, washed with water, and dried over anhydrous sodium sulfate. The solids are removed by filtration and the solvent removed in vacuo. The residue is purified by silica gel column chromatography to provide 6-(4-fluorophenyl)-5-[2-(methylsulfonyl)pyrimidin-4-yl]imidazo[2,1-b][1,3] oxazole (F) (Compound XI, Table 1)) as a white solid (1.8 g, 82%).

MS (ES+) 359 (M+1).
$^1$H NMR (300 MHz, DMSO) δ 8.75 (brm. 1H), 8.22 (brd, 2H), 7.68 (m, 2H), 7.30-7.42 (m, 3H), 3.39 (s, 3H).

Step 6:

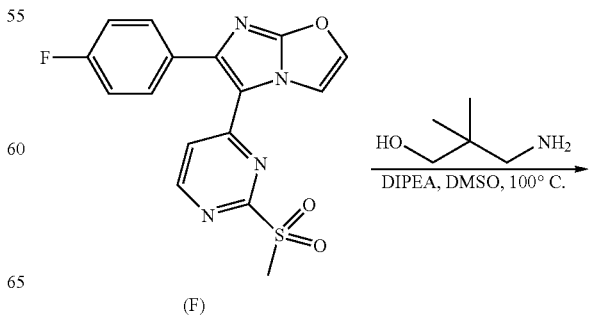

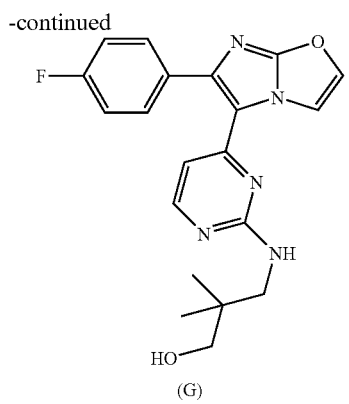

(G)

3-({4-[6-(4-Fluorophenyl)imidazo[2,1-b][1,3]oxazol-5-yl]pyrimidin-2-yl}amino)-2,2-dimethylpropan-1-ol (Compound XXXIX, Table 1).

To a solution of 6-(4-fluorophenyl)-5-[2-(methylsulfonyl)pyrimidin-4-yl]imidazo[2,1-b][1,3]oxazole (F) (0.5 g, 1.4 mmol) in dimethylsulfoxide is added 3-amino-2,2-dimethyl propanol (0.430 mg, 3.8 mmol) followed by the addition of diisopropylethylamine (0.631 g, 5.0 mmol). The mixture is heated at 100° C. overnight. After cooling to room temperature the reaction is diluted with water and extracted with dichloromethane (2×50 ml). The combined organic phase is dried over anhydrous sodium sulfate, filtered and the solvent removed in vacuo. The residue is purified by silica gel column chromatography eluting with ethyl acetate/hexane (3:1) to provide 3-({4-[6-(4-fluorophenyl)imidazo[2,1-b][1,3]oxazol-5-yl]pyrimidin-2-yl}amino)-2,2-dimethylpropan-1-ol (G) (0.46 g, 86%), m.p. 149° C.;

$^1$H NMR (300 MHz CDCl$_3$) δ: 8.06 (s, 1H), 7.98 (d, J=5.4 Hz, 1H), 7.59 (m, 2H), 7.45 (s, 1H), 7.11 (t, 2H), 6.49 (d, J=5.4 Hz, 1H), 3.29 (d, J=7.2 Hz, 2H), 3.21 (s, 2H), 0.95 (s, 6H).

The compounds shown in Table 1 (which is attached hereto and incorporated herein by reference) may be prepared in a manner similar to the above example.

Example 2

Preparation of 4-{4-[6-(4-fluorophenyl)-imidazo[2,1-b]thiazol-5-yl]-pyrimidin-2-ylamino}-piperidine-1-carboxylic acid tert-butyl ester An exemplary compound of the invention represented by Formula I (X=S) was prepared according to the following representative method.

Step 1:

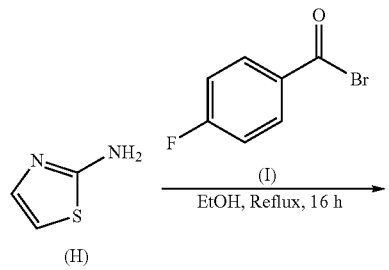

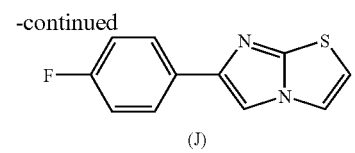

(J)

To a mixture of 2-aminothiazole (H) (23.7 g, 0.23 mol) and 2-bromo-1-(4-fluorophenyl)-ethanone (I) (50 g, 0.23 mol) is added absolute ethanol (600 mL). The reaction is allowed to reflux with vigorous stirring for 16 hours. The reaction mixture is reduced to half its original volume in vacuo. The remaining liquid is poured onto ice and the solution made basic by the addition of ammonium hydroxide solution (30%). The resulting fine solid is filtered and washed with water. The dark yellow solid so obtained is dried in a vacuum oven at 50° C. to provide 6-(4-fluorophenyl)-imidazo[2,1-b]thiazole (J) (43.0 g, 86%).

ESMS [M+H]$^+$=219;

$^1$H NMR (300 MHz CDCl$_3$) δ 8-7.6 (m, 3H), 7.38 (bs, 1H), 7.08 (bs, 2H), 6.79 (bs, 1H); $^{13}$C 75 MHz (NMR CDCl$_3$) δ: 163.2 (d, C—F, J=244.7 Hz), 150.1, 146.8, 130.3 (C—C—C—C—F), 126.7 (d, C—C—C—F, J=7.73 Hz), 118.4, 115.5 (d, C—C—F, J=21.4 Hz), 112.4, 107.6;

Step 2:

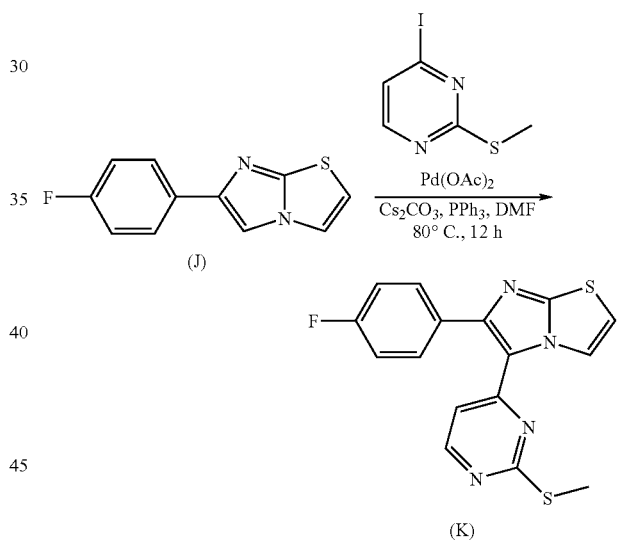

To a mixture of 6-(4-fluorophenyl)-imidazo[2,1-b]thiazole (J) (6.0 g, 27.6 mmol), 4-iodo-2-thiomethylpyrimidine (10.4 g, 41.3 mmol), cesium carbonate (13.4 g, 41.3 mmol), triphenylphosphine (2.88 g, 11 mmol), and palladium acetate (1.22 g, 5.5 mmol) is added anhydrous dimethylformamide (60 mL). The reaction mixture is sealed and shaken at 80° C. for 12 hours. The reaction was quenched by addition of water (200 mL). The aqueous layer is extracted with ethyl acetate (3×100 mL). The organic phase is washed sequentially with water (100 mL) and a saturated aqueous, sodium chloride solution (100 mL). The organic phase is dried over sodium sulfate, filtered, and the solvent evaporated in vacuo. The crude product is purified by silica gel column chromatography, eluting with a gradient of ethyl acetate/hexane (20-30%). After evaporation of the solvent, 6-(4-fluorophenyl)-5-(2-methylsulfanyl-pyrimidin-4-yl)-imidazo[2,1-b]thiazole (K) (Compound CXXXIX, Table 2) is obtained as a white solid (3.5 g, 37%) m.p. 151-152° C.;

ESMS [M+H]⁺=343;

¹H NMR (300 MHz, CDCl₃) δ: 8.61 (d, J=4.41 Hz, 1H), 8.27 (d, J=5.43 Hz, 1H), 7.66-7.58 (m, 2H), 7.2-7.12 (m, 2H), 7.0 (d, J=4.56 Hz, 1H), 6.86 (d, J=5.43 Hz, 1H), 2.64 (s, 3H);

¹³C NMR (75 MHz, CDCl₃) δ: 172.6, 163.1 (d, C—F, J=247.1 Hz), 156.4, 156.1, 152.7, 150.0, 131.1 (d, C—C—C—F, J=8.1 Hz), 130.7 (d, C—C—C—C—F, J=3.15 Hz), 122.2, 120.2, 115.9 (d, C—C—F, J=21.5 Hz), 112.8, 111.9, 14.2;

Anal. calcd. for C₁₆H₁₁FN₄S₂: C, 56.12; H, 3.24; N, 16.36. Found C, 55.81; H, 3.20; N, 16.10.

Step 3:

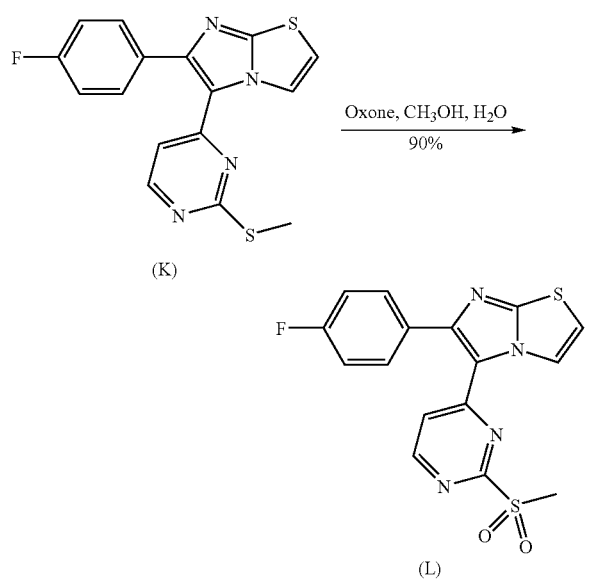

Step 4:

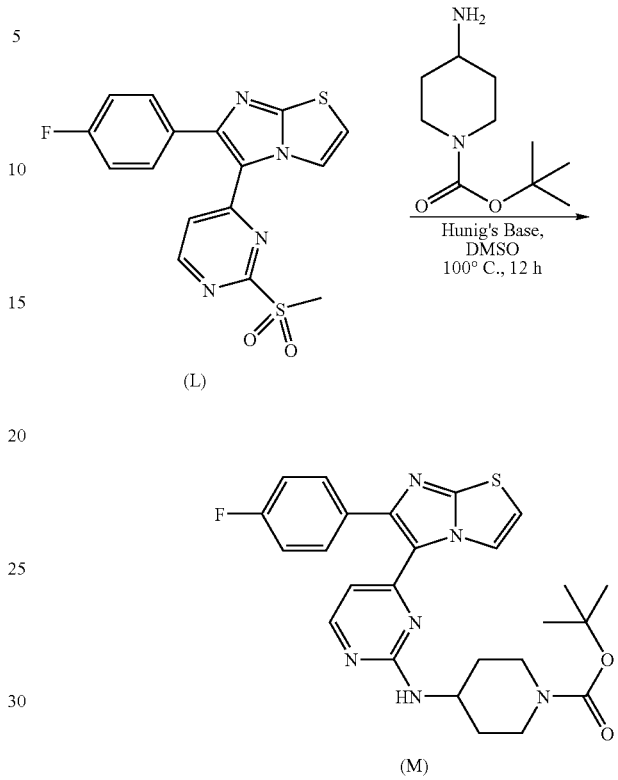

To a solution of the mixture (1.1:1) of 6-(4-fluorophenyl)-5-(2-methylsulfanyl-pyrimidin-4-yl)-imidazo[2,1-b]thiazole (K) and 6-(4-fluorophenyl)-imidazo[2,1-b]thiazole (J) (0.205 g, 0.6 mmol) in methanol (25 mL) is added drop-wise a solution of oxone (1.23 g, 1.8 mmol) in water (5 mL). The reaction is stirred at room temperature for 16 hours. The volatiles are removed in vacuo at room temperature. To the residue is added dichloromethane. The organic phase is washed sequentially with water and a saturated, aqueous sodium chloride solution. The organic phase is dried over anhydrous sodium sulfate, filtered, and the solvent evaporated in vacuo. The crude product is purified by silica gel column chromatography, eluting with ethyl acetate hexane (1:1) to yield 6-(4-fluorophenyl)-5-(2-methanesulfonyl-pyrimidin-4-yl)-imidazo[2,1-b]thiazole (L) (Compound CXL, Table 2) as a white solid (0.113 g, 98%); m.p. 197-198° C.;

ESMS [M+H]⁺=375;

¹H NMR (300 MHz, CDCl₃) δ: 8.84-8.9 (m, 1H), 8.56-8.5 (bd, 1H), 7.68-7.58 (m, 2H), 7.38-7.30 (m, 1H), 7.26-7.16 (m, 2H), 7.1 (m, 1H), 3.38 (s, 3H);

¹³C NMR (75 MHz, CDCl₃) δ: 165.8, 163.4 (d, C—F, J=248.6 Hz), 157.4, 156.9, 154.4, 152.1, 131.1 (d, C—C—C—F, J=8.3 Hz), 130.3 (d, C—C—C—C—F, J=6.3 Hz), 123.2, 119.5, 117.3, 116.2 (d, C—C—F, J=21.6 Hz), 113.9, 39.2;

Anal. calcd. for C₁₆H₁₁FN₄O₂S₂.0.045 CHCl₃: C, 51.33; H, 2.96; N, 14.96. Found: C, 50.76; H, 2.83; N, 14.62.

To a solution of 6-(4-fluorophenyl)-5-(2-methanesulfonyl-pyrimidin-4-yl)-imidazo[2,1-b]thiazole (L) (1.05 g, 2.8 mmol) in dimethylsulfoxide (12.0 mL) is added 4-amino-piperidine-1-carboxylic acid tert-butyl ester (1.12 g, 5.6 mmol) followed by Hunig's Base (0.76 mL, 5.6 mmol). The reaction mixture is sealed and set to shake at 100° C. for 12 hours. After cooling to room temperature, water is added (50 mL) and the aqueous phase extracted with ethyl acetate (4×20 mL). The combined organic phase is washed with a saturated, aqueous, sodium chloride solution (3×50 mL) and dried over anhydrous sodium sulfate. The organic phase is filtered and the solvent evaporated in vacuo. The crude product is purified by silica gel column chromatography eluting with ethyl acetate/hexane (3/2). The compound 4-{4-[6-(4-fluorophenyl)-imidazo[2,1-b]thiazol-5-yl]-pyrimidin-2-ylamino}-piperidine-1-carboxylic acid tert-butyl ester (M) (Compound CCXXXIII, Table 2) is obtained as a light yellow solid (1.2 g, 88%); m.p. 209-211° C.;

¹H NMR (300 MHz, CDCl₃) δ: 8.51 (d, J=6 Hz), 8.07 (d, J=7.2 Hz), 7.65-7.5 (m, 2H), 7.16-7.1 (m, 2H), 6.93 (d, J=6 Hz), 6.48 (d, J=7.2 Hz), 5.17 (bs, 1H), 3.9-4.2 (m, 5H), 3.03-2.97 (m, 2H), 2.16-2.07 (m, 2H), 1.49 (s, 9H);

¹³C NMR (75 MHz, CDCl₃) δ: 162.96 (d, C—F, J=247 Hz), 161.5, 157.7, 156.94, 154.7, 151.9, 148.99, 131.07 (d, C—C—C—F, J=8.5 Hz), 130.9 (d, C—C—C—C—F, J=3.2 Hz), 121.7, 120.8, 115.6 (d, C—C—F, J=21.6 Hz), 107.2, 79.7, 48.4, 42.7 (bs), 32.2, 28.4;

ESMS [M+H]⁺=495;

Anal. calcd. for C₂₅H₂₇FN₆O₂S.0.065CH₂Cl₂: C, 60.71; H, 5.50; N, 16.99. Found: C, 60.15; H, 5.14; N, 16.41.

Example 3

Preparation of N'-{4-[6-(4-fluorophenyl)imidazo[2,1-b][1,3]thiazol-5-yl]pyrimidin-2-yl}-N,N-dimethyl-ethane-1,2-diamine

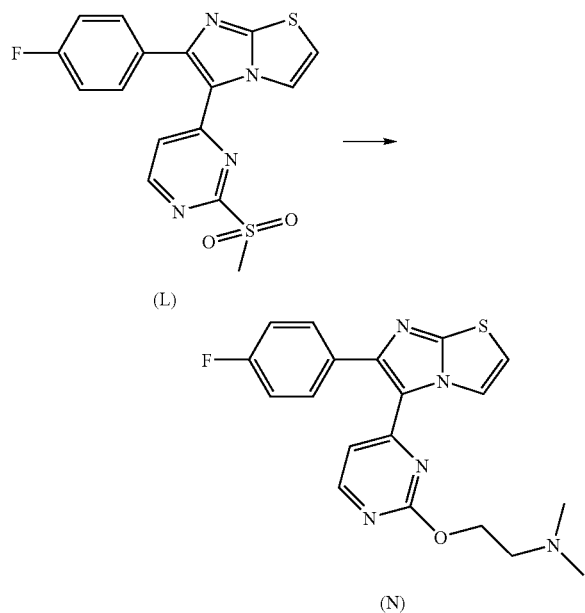

To a solution of 6-(4-fluorophenyl)-5-[2 (methylsulfonyl)pyrimidin-4-yl]imidazo[2,1-b][1,3]thiazole (L; see Example 2, supra) (200 mg, 0.53 mmol) in dry dimethylsulfoxide (4 mL) is added N,N-dimethylethanolamine (273 mg, 3.06 mmol) and potassium carbonate (365 mg, 2.64 mmol). The reaction mixture is stirred at 100° C. for 6 hours, diluted with water (5 mL), and extracted with ethyl acetate (2×10 ml). The organic phase is washed with water, dried over anhydrous sodium sulfate, filtered and the solvent evaporated in vacuo. The residue is purified by silica gel column chromatography to provide the compound N'-{4-[6-(4-fluorophenyl)imidazo[2,1-b][1,3]thiazol-5-yl]pyrimidin-2-yloxy}-N,N-dimethyl-ethanamine (N) (108 mg).

$^1$H NMR (300 MHz, DMSO) δ: 8.55 (d, J=4.8 Hz, 1H), 8.41 (d, J=5.4 Hz, 1H), 7.65 (m, 2H), 7.52 (d, J=4.5 Hz, 1H), 7.32 (t, J=9.3 Hz, 2H), 6.82 (d, J=5.4 Hz, 1H), 4.53 (t, J=5.7 Hz, 2H), 2.98 (t, J=5.7 Hz, 2H), 2.46 (s, 6H). MS (ES+) 384 (M+1).

The compounds shown in Table 2 (which is attached hereto and incorporated herein by reference) may be prepared in a manner similar to Examples 2 and 3.

Example 4

Compounds of the invention are screened for the ability to inhibit ATF2 phosphorylation by p38 MAP Kinase in vitro. The ability of compounds to inhibit ATF2 phosphorylation in this in vitro assay is correlated with the inhibition of p38 MAP Kinase and TNFα expression in vivo, and is therefore an indicator of potential in vivo therapeutic activity (Raingeaud, J., et al, J. Biol. Chem., 270: 7420-7426, 1995, Brinkman, M. N., et al, J. Bil. Chem. 274: 30882-30886, 1999 and Fuchs, S. Y. et al, J. Biol. Chem. 275: 12560-12564, 2000).

Materials: All kinases and the substrate ATF2 are acquired from Upstate (Charlottesville, Va.). p38 MAP Kinases are recombinant human full-length proteins with an amino-terminal GST fusion, expressed in and purified from E. coli. ATF2 is a GST fusion protein containing amino acids 19-96 of human ATF2 expressed in E. coli. All proteins were aliquoted and stored at −80° C.

Methods: p38 MAP Kinase assays are performed using an assay buffer containing 25 mM HEPES, pH 7.5, 10 mM MgCl$_2$, 2 mM DTT, 20 mM β-glycerophosphate, 0.1 mM Na$_3$VO$_4$, 40 µM ATP and 1.25 µM of ATF2, together with 6 ng of p38α protein, 12 ng p38β protein, 1.5 ng p38γ, or 0.4 ng JNK2α2. Compounds are serially diluted in DMSO and 2 µL of test compound at 25× final concentration is used. The vehicle control receives DMSO only. Test compounds are pre-incubated with 20 µl of enzyme in kinase buffer (25 mM HEPES, pH 7.5, 10 mM MgCl$_2$, 2 mM DTT, 20 mM β-glycerophosphate and 0.1 mM Na$_3$VO$_4$) at room temperature for 15 minutes. Reactions are initiated by addition of 30 µl substrate solution to yield a final concentration of 40 µM ATP and 1.25 µM ATF2 in kinase buffer. The reactions are incubated for 30 minutes at 37° C. and terminated by the addition of 18 µl of 200 mM EDTA. An ELISA method is used to measure the phosphorylation of ATF2 at Thr 69. High binding 96-well plates (Corning 3369) are coated with 50 µl of kinase reaction for 1 hour at 37° C. The coated plates are washed with 200 µl washing buffer (25 mM Tris HCl, pH 8.3, 192 mM glycine, 0.1% SDS and 0.05% Tween-20) three times. The plates are then washed three times with SuperBlock in TBS (Pierce, 37535). After blocking, plates are incubated with 50 µl of rabbit anti-phospho-ATF2 antibody (Cell Signaling, 9221 L, 1:500) for 30 minutes at 37° C. Plates are washed three times with washing buffer prior to incubation with 50 µl HRP-conjugated goat anti-rabbit antibody (Cell Signaling, 7074, 1:500) for 30 minutes at 37° C. Plates are then washed three times with washing buffer before incubation with 50 µl of Ultra TMB-ELISA (Pierce, 34028) for 8 minutes at room temperature. Finally, 50 µl of phosphoric acid (1 M) is added to stop reactions and plate absorbance is read at 450 nm on a SpectraMax 250 plate reader.

Results: The results of the p38α assay for certain compounds of the invention are shown in Table 1 and Table 2. It is found that compounds of the invention inhibit the phosphorylation of ATF2 in this in vitro assay. Preferred compounds exhibit IC$_{50}$ values of less than 500 nM, more preferably less than 100 nM, and still more preferably less than 20 nM.

Example 5

Compounds of the invention are screened for the ability to inhibit TNFα and IL-1β release from THP-1 cells stimulated with lipopolysaccharide (LPS) in vitro. The ability of compounds to inhibit TNFα and IL-1β release in this in vitro assay is correlated with the inhibition of p38 activity and TNFα and IL-1β expression in vivo, and is therefore an indicator of potential in vivo therapeutic activity (Lee J. C. et al, Ann. N.Y. Acad. Sci. 696: 149-170, 1993 and Nature, 372: 739-746, 1994).

Materials: THP-1 cells from ATCC (TIB202) are maintained at 37° C., 5% CO$_2$ in RPMI 1640 media (MediaTech, Herndon, Va.) containing 4.5 g/L glucose, supplemented with 10% fetal bovine serum, 1% penicillin/streptomycin and 50 µM β-mercaptoethanol.

Methods: Test compounds are initially dissolved in RPMI media with 1% DMSO (v/v). Compounds are then serially diluted in RPMI media for all subsequent dilutions. The assay is performed under sterile conditions. THP-1 cells at a culture density of 6-8×10⁵ cells/ml are collected and resuspended in the RPMI media at 10⁶ cells/ml. 100 μl of resuspended cells are added to each well, which contain 100 μl of a test compound. Test compounds are prepared at twice the final concentration. Final DMSO concentration is no more than 0.5% (v/v). Cells are preincubated with compound for 30 minutes at 37° C., 5% $CO_2$ prior to stimulation with lipopolysaccharide (LPS) (Sigma L-2880, 4 mg/ml stock in PBS). The final LPS concentration in each well is 10 or 30 μg/ml for TNFα and IL-1β release, respectively. Unstimulated control cell suspensions receive PBS vehicle only. Cell mixtures are incubated for 18 or 48 hours for TNFα and IL-1β release, respectively. 150 μl of supernatants are taken and transferred to a fresh plate and stored at −20° C. until further analysis. TNFα and IL-1β levels are measured using ELISA kits (Biosource (KHC3012 for TNFα; KAC1192 for IL-1β). A SpectraMAX 250 is used as the plate reader. Analysis is performed by non-linear regression to generate a dose response curve. The calculated $IC_{50}$ value is the concentration of the test compound that causes a 50% decrease in TNFα or IL-1β levels.

Results: Compounds of the invention inhibit the release of TNFα, IL-1β or both TNFα, and IL-1β in this in vitro assay. The TNFα inhibition data for certain compounds of the invention are shown in Tables 1 and 2. Preferred compounds exhibit $IC_{50}$ values for TNFα and/or IL-1β of less than 500 nM, more preferred compounds less than 200 nM, still more preferred compounds less than 100 nM, and even still more preferred compounds less than 20 nM.

Example 6

Compounds of the invention are screened for the ability to inhibit TNFα release from primary human peripheral blood mononuclear cells (PBMC) stimulated with lipopolysaccharide (LPS) in vitro. The ability of compounds to inhibit TNFα release in this in vitro assay is correlated with the inhibition of p38 activity and is therefore an indicator of potential in vivo therapeutic activity (Osteoarthritis & Cartilage, 10: 961-967, 2002 and Laufer, S. A. and Wagner, G. K., J. Med. Chem. 45: 2733-2740, 2002).

Materials and Methods: Human peripheral blood mononuclear cells (PBMC) are isolated by differential centrifugation through a Ficoll-HyPaque density gradient from pooled serum of 3-8 individual blood donors. Isolated PBMC contain approximately 10% CD-14 positive monocytes, 90% lymphocytes and <1% granulocytes and platelets. PBMC (10⁶/ml) are cultured in polystyrene plates and stimulated with lipopolysaccharide (LPS; 50 ng/ml; Sigma, St. Louis, Mo.) in the presence and absence of compound, in duplicate, for 24 hr at 37° C. in GIBCO™ RPMI medium (Invitrogen, Carlsbad, Calif.) without serum. The TNFα level in cell supernatants is determined by ELISA using a commercially available kit (MDS Panlabs #309700).

Results: Preferred compounds of the invention inhibit the release of TNFα in this assay with an $IC_{50}$ value of less than 500 nM, more preferably less than 100 nM, and still more preferably less than 20 nM.

Example 7

Compounds of the invention are screened for the ability to inhibit the release of TNFα in an in vivo animal model. (See, e.g., Griswold D. E. et al, Drugs Exp. Clin. Res. 19: 243-248, 1993, Badger, A. M. et al, J. Pharmacol. Exp. Ther., 279: 1453-1461, 1996, Dong, C. et al, Annu. Rev. Immunol., 20: 55-72, 2002 (and references cited therein), Ono, K. and Han, J., Cellular Signalling, 12: 1-13, 2000 (and references cited therein) and Griffiths, J. B. et al, Curr. Rheumatol. Rep., 1: 139-148, 1999).

Without being bound by any particular theory, it is believed that inhibition of TNFα in this model is due to inhibition of p38 MAP kinase by the compound.

In Vivo LPS Challenge Study

Male Sprague-Dawley rats (0.2-0.35 kg) are randomly divided into groups of six or more and are dosed intravenously by infusion or bolus injection, or are dosed orally with test compounds in a suitable formulation in each case. Thirty minutes following end of infusion or bolus injection, and 1-2 hr following oral administration, lipopolysaccharide E. coli/0127:B8 (0.8 mg/kg) is administered IV. Blood samples are collected 1.5 hours post-treatment with LPS. Serum TNFα levels are determined using the ELISA kit from Biosource (KRC3011C) and compared to that from vehicle-treated control.

Results: Preferred compounds of the invention inhibit the release of TNFα in this in vivo assay. Preferred compounds delivered intravenously exhibit an $ED_{50}$ value of less than 20 mg/kg, more preferably less than 5 mg/kg, and still more preferably less than 1 mg/kg. Preferred compounds delivered orally exhibit an $ED_{50}$ value of less than 100 mg/kg, more preferably less than 20 mg/kg, and still more preferably less than 1 mg/kg.

Example 8

Kinase Selectivity

A selectivity panel is used to test the cross-reactivity of compounds of the invention with the β and γ isoforms of p38 MAP kinase, $Src^{p60}$ and JNK2α2. The p38β, p38γ, and JNK2α2 assays are described in Example 4. The $Src^{p60}$ assay measures the ability of compounds to inhibit $Src^{p60}$-catalyzed phosphorylation of a peptide substrate.

Methods: Compounds are serially diluted in DMSO and 1 μL of test compound at 25× final concentration is used. The vehicle control receives DMSO only. Test compounds are pre-incubated with 10 μL of water containing 5.3 units of $Src^{p60}$ enzyme (Upstate, Charlottesville, Va.) at room temperature for 15 minutes. Reactions are initiated by addition of 14 μL substrate cocktail (45 mM HEPES, pH 7.5, 18 mM $MgCl_2$, 36 mM β-glycerophosphate and 0.18 mM $Na_3VO_4$, 71.5 μM ATP and 1.8 μM CDC2p34 substrate ((Biotin-KVEKIGEGTYGVVYK-amide, custom synthesis, New England Peptide). The reactions are incubated for 3.5 hr at room temperature and terminated by the addition of 25 μl of 25 mM EDTA. 8 μl of reaction mix is transferred to a Costar Black 96-well polystyrene plate and 96 μl of detection mixture (30 μl of APC-Strepavidin (Perkin Elmer Life Sciences) (1 mg/ml in water), 8 μl Eu-P66 (Perkin Elmer Life Sciences) (500 μg/ml) in 1 ml of Tris-EDTA buffer pH 8.0 (Fluka)). The reactions are incubated for 1 hr at room temperature. Time resolved fluorescence is read at 665 and 615 nm using the Victor V program LANCE 615/665 on a Victor² V plate reader (Perkin Elmer Life Sciences).

Results: Table III shows kinase selectivity panel data. Selectivity over p38β ranged from 3- to 71-fold, with LXXX-VII exhibiting 17-fold selectivity over p38β as compared to p38α. The lowest value observed for selectivity over p38γ and Src was 465-fold as compared to p38α. While Compounds LXXXVII, LXXXIV, LXXI, CXIX and CCLXXXI exhibited selectivities over JNK2α2 that ranged from 83- to 191-fold, compounds CCLXXVII, CCLXXIX and CCLXXX showed somewhat lower selectivity over JNK2α2, ranging from 28- to 64-fold of the activity against p38α.

TABLE III

In vitro potency and selectivity of lead compounds. $IC_{50}$ values (nM) are reported.

| cmpd | Selectivity ($IC_{50}$ nM) | | | |
|---|---|---|---|---|
| | p38β | p38γ | Src | JNK2α2 |
| LXXXVII | 150 | 59500 | 25930 | 1040 |
| LXXXIV | 1288 | >81268 | >29488 | 2258 |
| LXXI | 114 | >519000 | 12940 | 1588 |
| CXIX | 288 | >100000 | >100000 | 2078 |
| CCLXXXI | 24.6 | >100000 | >9025 | 762 |
| CCLXXVIII | 6.3 | >100000 | >70000 | 53.6 |
| CCLXXIX | 1.8 | >100000 | >64000 | 23.3 |
| CCLXXX | 95.4 | >100000 | >11000 | 646 |

Various compounds of the present invention are screened against a panel of 24 additional kinases (Upstate, Charlottesville, Va.). Compounds are tested 0.1 μM and 1 μM in reactions containing 40 μM ATP. Incorporation of radiolabeled phosphate ($^{32}P$) into each kinase substrate is measured in the presence and absence of test compound. Tables IV(a) and IV(b) show the broad kinase panel selectivity values for these compounds. Results are reported as the percent decrease in the amount of $^{32}P$ incorporated into the substrate in the presence of compound, compared to buffer control.

TABLE IV(a)

Broad selectivity panel. Compounds are screened against kinases at concentrations of 0.1 and 1 μM, and compared to kinase activity in the absence of compound. Percent inhibition at each concentration is reported.

| | LXXXVII | | LXXI | | CXIX | | CCLXXXI | |
|---|---|---|---|---|---|---|---|---|
| compound | 0.1 μM | 1 μM | 0.1 μM | 1 μM | 0.1 μM | 1 μM | 0.1 μM | 1 μM |
| CaMKIV | −12 | 10 | 5 | 6 | 13 | 7 | 12 | 33 |
| CDK2/cyclinA | 1 | 0 | 0 | 8 | −1 | −1 | −2 | 5 |
| CK2 | 4 | 4 | 3 | 12 | 9 | 3 | 6 | 16 |
| c-RAF | 15 | 58 | 7 | 42 | −3 | 3 | −4 | 8 |
| FGFR3 | −23 | −21 | −1 | 16 | 9 | −2 | −27 | 26 |
| GSKβ | 6 | 8 | −8 | 10 | 11 | 13 | 6 | 19 |
| InsR | −8 | 8 | −25 | 12 | 8 | 3 | −7 | 14 |
| JNK1α1 | −25 | 0 | −20 | 3 | 1 | −18 | −13 | 6 |
| JNK3-His | 19 | 61 | −7 | 59 | 19 | 56 | 19 | 75 |
| Lck | −15 | 18 | 8 | 17 | 13 | 10 | 26 | 35 |
| Lyn | −32 | −13 | 4 | 10 | 2 | −12 | −6 | 4 |
| MAPK1 | 12 | 27 | 27 | 56 | 7 | 15 | 25 | 49 |
| MAPK2 | −4 | 14 | −5 | 18 | 10 | 7 | 10 | 23 |
| MEK1 | 3 | −1 | 2 | 6 | −1 | 2 | −3 | 7 |
| MKK6 | −4 | 54 | −5 | 80 | 1 | 75 | 19 | 76 |
| p70S6K | −4 | −1 | −10 | 6 | 0 | −5 | −16 | −10 |
| PDGFR α | −6 | −11 | 10 | 9 | 26 | 10 | 11 | 21 |
| PKA | −10 | −6 | 16 | 11 | 1 | −8 | −11 | −2 |
| PKB α | −2 | 5 | −5 | 9 | 11 | 5 | −2 | 6 |
| PKBβ | −26 | −29 | −42 | −5 | −4 | −19 | −12 | 13 |
| ROCK-II | 2 | 8 | −7 | 10 | 16 | −8 | 10 | 9 |
| SAPK4 | −3 | −1 | −1 | 3 | 3 | −4 | 2 | 7 |
| Syk | 17 | 23 | −5 | 33 | 35 | 33 | 17 | 33 |
| ZAP-70 | −51 | −14 | −17 | 4 | 13 | −9 | 12 | 30 |

TABLE IV(b)

Broad selectivity panel. Compounds were screened against kinases at concentrations of 0.1 and 1 μM, and compared to kinase activity in the absence of compound. Percent inhibition at each concentration is reported.

| | CCLXXVIII | | CCLXXIX | | CCLXXX | |
|---|---|---|---|---|---|---|
| compound | 0.1 μM | 1 μM | 0.1 μM | 1 μM | 0.1 μM | 1 μM |
| CaMKIV | 8 | 21 | 18 | −2 | −10 | 7 |
| CDK2/cyclinA | 1 | 20 | 24 | 65 | 3 | 19 |
| CK2 | 5 | 10 | 8 | 4 | 10 | 32 |
| c-RAF | 26 | 66 | 32 | 83 | 21 | 75 |
| FGFR3 | 19 | 32 | 9 | 10 | −1 | 13 |
| GSK3β | 16 | 66 | 15 | 57 | 5 | 14 |
| InsR | −28 | −4 | 9 | 2 | 4 | 27 |
| JNK1α1 | −13 | 61 | 37 | 86 | −26 | 18 |
| JNK3-His | 78 | 100 | 97 | 101 | 39 | 84 |
| Lck | 5 | 31 | 2 | −3 | −3 | 27 |
| Lyn | −26 | −29 | −7 | −13 | −24 | 27 |
| MAPK1 | 25 | 63 | 29 | 79 | 20 | 45 |
| MAPK2 | 18 | 42 | 14 | 43 | −9 | 9 |
| MEK1 | 6 | 13 | 7 | 11 | 9 | 13 |
| MKK6 | 26 | 83 | 8 | 90 | 0 | 62 |
| p70S6K | −11 | 4 | 9 | 10 | 7 | 18 |
| PDGFR α | 23 | 17 | 0 | −9 | 1 | 8 |
| PKA | −6 | 10 | 6 | −2 | 0 | 11 |
| PKB α | −6 | 4 | 5 | 6 | −1 | 13 |
| PKBβ | −3 | 41 | 0 | −30 | −18 | 13 |
| ROCK-II | −6 | 6 | 10 | 12 | 8 | 10 |
| SAPK4 | −3 | −4 | 3 | 0 | 0 | 6 |

TABLE IV(b)-continued

Broad selectivity panel. Compounds were screened against kinases at concentrations of 0.1 and 1 μM, and compared to kinase activity in the absence of compound. Percent inhibition at each concentration is reported.

| compound | CCLXXVIII | | CCLXXIX | | CCLXXX | |
|---|---|---|---|---|---|---|
| | 0.1 μM | 1 μM | 0.1 μM | 1 μM | 0.1 μM | 1 μM |
| Syk | 7 | −6 | 3 | 10 | 5 | 40 |
| ZAP-70 | −53 | 18 | 13 | −1 | −2 | 9 |

Example 9

In Vivo Established Type II Collagen Arthritis Study

Compounds are tested in the collagen-induced model of arthritis in rats. Female Lewis rats (0.16-0.2 kg) are injected subcutaneously at the base of the tail and two sites on the back on day 0 and 6 with 300 μl of Freund's Incomplete Adjuvant containing 2 mg/ml of Bovine Type II Collagen. On day 9 of the study, caliper measurements of both hind leg ankle joints are performed. This measurement is considered the normal, pre-disease measurement. When ankle swelling is clearly established in at least one hind paw (caliper measurement increase from 0.263 to 0.282 inches), rats are enrolled into the treatment phase of the study. This occurs on day 10 or 11 of the study and is considered to be day 1 of arthritis. Enrolled animals are randomized and administered vehicle control or compound (1, 3.3, 10, or 30 mg/kg, bid), unless otherwise indicated, or dexamethasone (0.0375 mg/kg, bid) via oral gavage on days 1-7 of arthritis (treatment days). Ankle diameters are measured on each day of treatment. Mean increases in ankle diameter for 7 lead compounds are shown below in FIGS. 3-9.

Following sacrifice on day 7, both hind paws are removed from each animal and weighed. Knees and ankles from all animals in all groups are preserved, decalcified in 5% formic acid and trimmed into two approximately equal longitudinal (ankles) or frontal (knees) halves, dehydrated, cleared, infiltrated, and embedded in paraffin. Blocks are sectioned and stained with Toluidine Blue.

Tissues are examined microscopically and scored for knee and ankle inflammation (cellular infiltration), pannus formation and infiltration, cartilage damage (loss of Toluidine staining and collagen disruption) and bone resorption. Scoring is on a scale from 0-5, where a score of 0 is normal and a score of 5 indicates severe damage or evidence of disease or both.

Results: Tested compounds show dose-dependent inhibition of clinical and histopathologic parameters of arthritis, including inflammation and bone damage. The results are summarized as a 50% reduction in measurement of disease parameters ($ED_{50}$ in mg/kg) in Table V.

TABLE V

Inhibition of collagen-induced arthritis in rats by compounds of the present invention. $ED_{50}$ values in mg/kg are shown for several parameters of arthritis.

| Compound identifier | ankle diameter | paw weights | summed ankle histology | summed ankle histology |
|---|---|---|---|---|
| LXXXVII | 1.29 | 1.88 | 2.07 | 0.42 |
| LXXXIV | 1.9 | 2 | 2.6 | 0.6 |
| CXIX | 2.3 | 3.75 | 2.64 | 1.19 |
| CCLXXXI | 0.98 | 0.94 | 0.93 | 0.2 |
| CCLXXVIII | 2.04 | 1.55 | 3.09 | 1.24 |
| CCLXXIX | 2.09 | 2.57 | 4.29 | 0.72 |
| CCLXXX | 5.43 | 3.51 | 7.6 | 1.04 |

Example 10

Compounds are tested for activity against a variety of cancer cell lines. Cancer cell lines include those for breast carcinoma, colorectal carcinoma, malignant melanoma, gastric cancer, and non-small cell lung cancer (NSCLC).

The contents of all references cited herein are hereby incorporated by reference.

TABLE 1

| Structure | Compounds | p38α (ELISA) IC50 (nM) | TNFα (THP-1) IC50 (nM) |
|---|---|---|---|
| 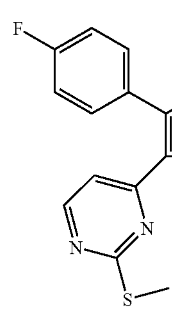 | X | | 1130 |

TABLE 1-continued

| Structure | Compounds | p38α (ELISA) IC50 (nM) | TNFα (THP-1) IC50 (nM) |
|---|---|---|---|
| (4-fluorophenyl imidazo-oxazole pyrimidine methylsulfonyl structure) | XI | 4430 | |
| Chiral (4-fluorophenyl imidazo-oxazole pyrimidine with isobutyl amino alcohol) | XII | 16.7 | 11.8 |
| (4-fluorophenyl imidazo-oxazole pyrimidine with serinol) | XIII | 13.0 | |
| (4-fluorophenyl imidazo-oxazole pyrimidine with ethanolamine) | XIV | 41.65 | 338 |

TABLE 1-continued
| Structure | Compounds | p38α (ELISA) IC50 (nM) | TNFα (THP-1) IC50 (nM) |
|---|---|---|---|
| 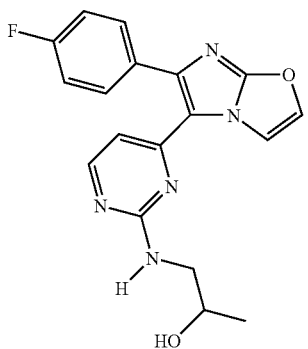 | XV | 30.7 | 18.8 |
| Chiral 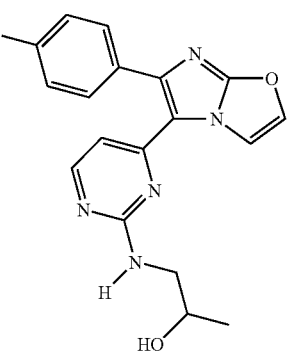 | XVI | 37.1 | 19.3 |
| 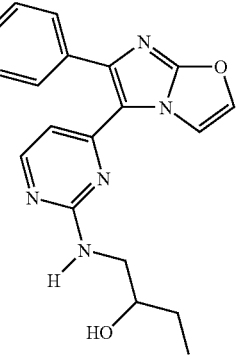 | XVII | 15.65 | 15.88 |
| 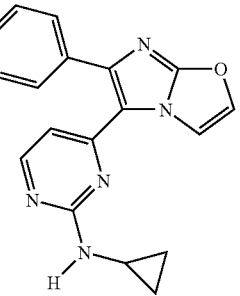 | XVIII | 0.44 | 11.2 |

TABLE 1-continued
| Structure | Compounds | p38α (ELISA) IC50 (nM) | TNFα (THP-1) IC50 (nM) |
|---|---|---|---|
| 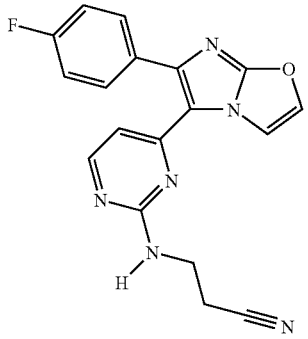 | XIX | 100 | 1140 |
| 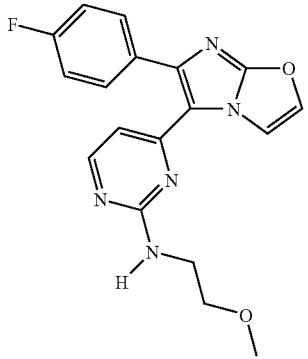 | XX | 24.3 | 65 |
| Chiral<br>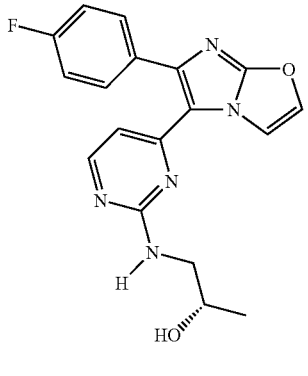 | XXI | 6.86 | 13.9 |
| Chiral<br>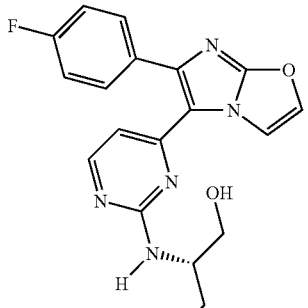 | XXII | 3.7 | 18.56 |

TABLE 1-continued
| Structure | Compounds | p38α (ELISA) IC50 (nM) | TNFα (THP-1) IC50 (nM) |
|---|---|---|---|
| 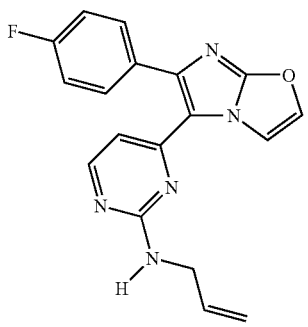 | XXIII | 11.9 | 9.08 |
| 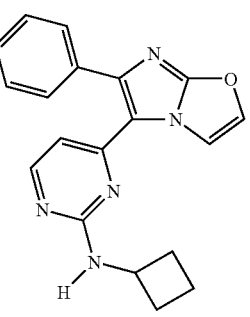 | XXIV | 15 | 1.78 |
| 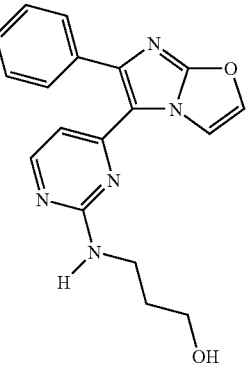 | XXV | 21.46 | 466 |
| 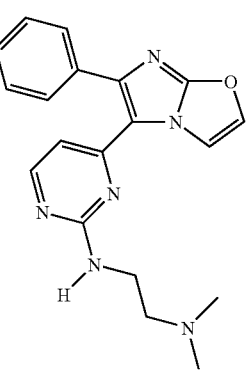 | XXVI | 480 | 100 |

TABLE 1-continued

| Structure | Compounds | p38α (ELISA) IC50 (nM) | TNFα (THP-1) IC50 (nM) |
|---|---|---|---|
| Chiral | XXVII | 20.5 | 6.08 |
| 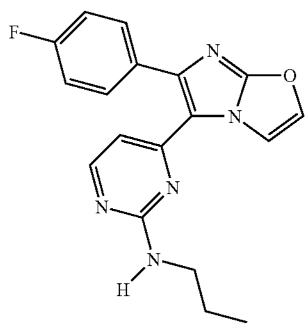 | XXVIII | 3.47 | 15.3 |
| 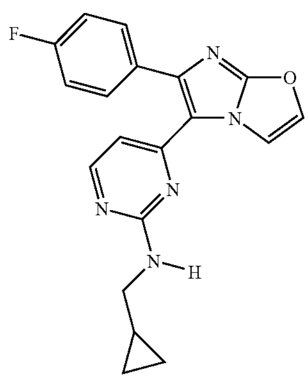 | XXIX | 4.28 | 4.45 |
| Chiral | XXX | 34.8 | 12.3 |

TABLE 1-continued

| Structure | Compounds | p38α (ELISA) IC50 (nM) | TNFα (THP-1) IC50 (nM) |
|---|---|---|---|
| 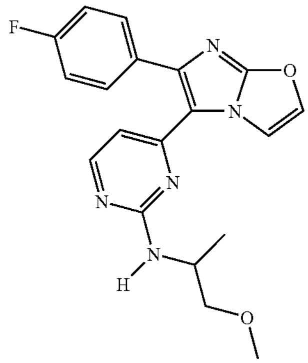 | XXXI | 1.6 | 10.3 |
| Chiral | XXXII | 19 | 4.89 |
| 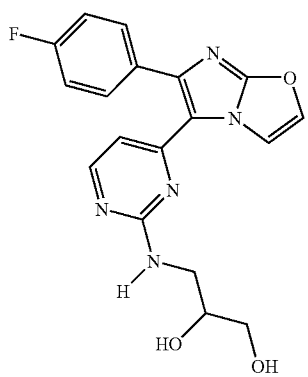 | XXXIII | 143 | 57 |
| 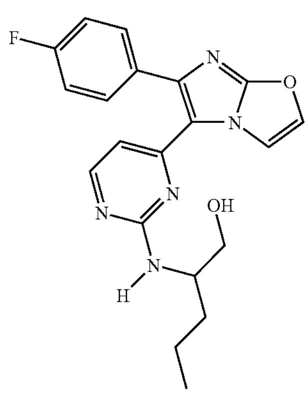 | XXXIV | 2.19 | 19.7 |

TABLE 1-continued

| Structure | Compounds | p38α (ELISA) IC50 (nM) | TNFα (THP-1) IC50 (nM) |
|---|---|---|---|
| 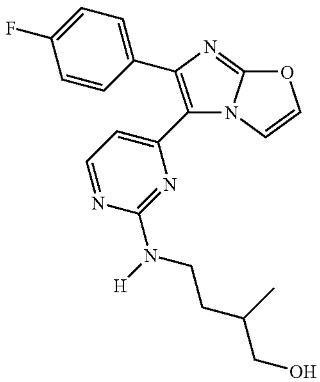 | XXXV | 17.9 | 17.9 |
| 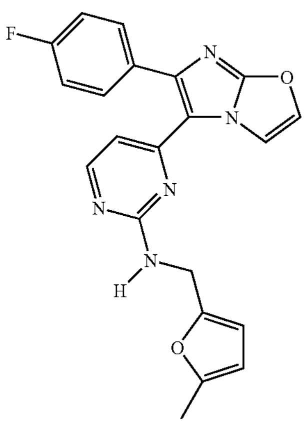 | XXXVI | 103 | 76.6 |
| 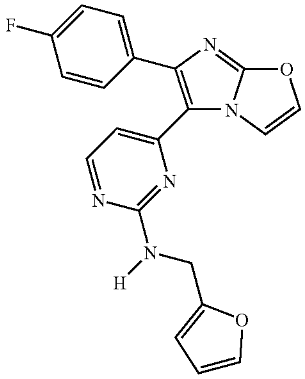 | XXXVII | 5.95 | 21.5 |

TABLE 1-continued

| Structure | Compounds | p38α (ELISA) IC50 (nM) | TNFα (THP-1) IC50 (nM) |
|---|---|---|---|
| 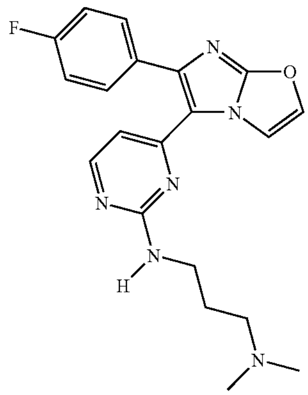 | XXXVIII | 343 | 168 |
| 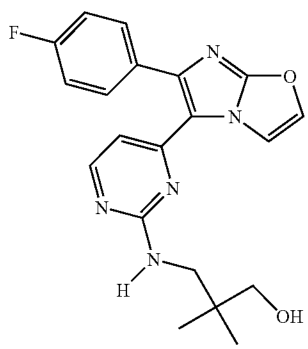 | XXXIX | 5.25 | 5.88 |
| 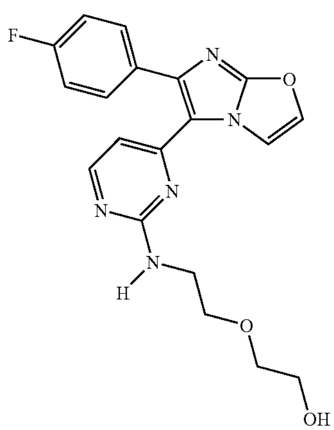 | XL | 79 | 93 |
| 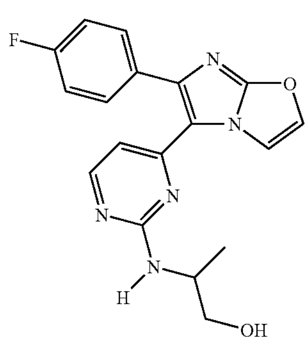 | XLI | 1.75 | 49.2 |

TABLE 1-continued
| Structure | Compounds | p38α (ELISA) IC50 (nM) | TNFα (THP-1) IC50 (nM) |
|---|---|---|---|
| Chiral 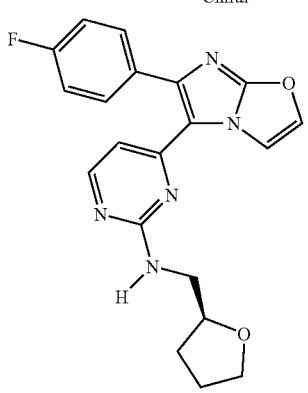 | XLII | 80.8 | 11.2 |
| 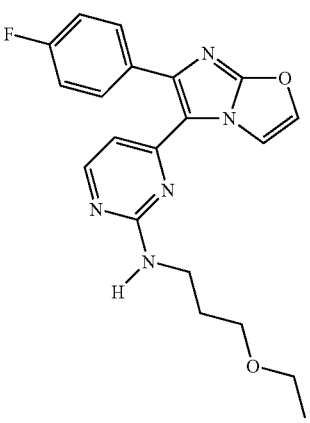 | XLIII | 1.56 | 13.5 |
| 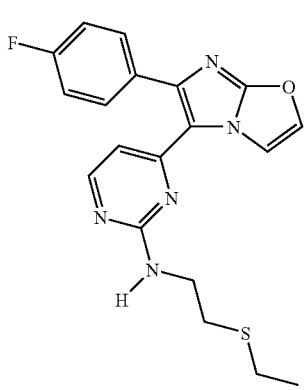 | XLIV | 10.5 | 34.5 |

TABLE 1-continued
| Structure | Compounds | p38α (ELISA) IC50 (nM) | TNFα (THP-1) IC50 (nM) |
|---|---|---|---|
| 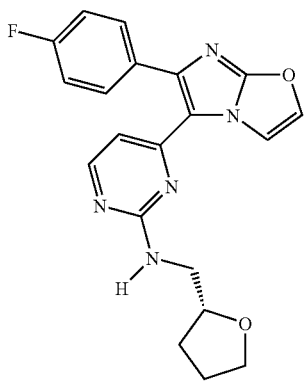 Chiral | XLV | 11.7 | 11.2 |
| 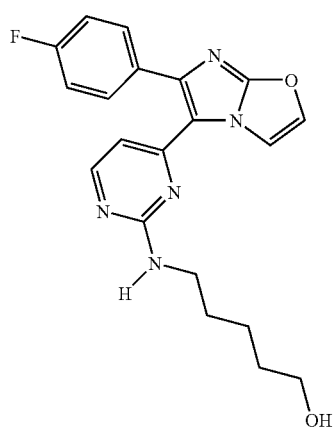 | XLVI | 23.1 | 17.2 |
| 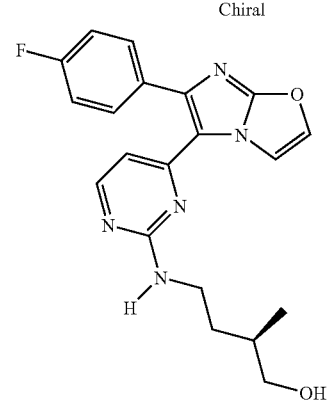 Chiral | XLVII | 31.4 | 13.7 |

TABLE 1-continued

| Structure | Compounds | p38α (ELISA) IC50 (nM) | TNFα (THP-1) IC50 (nM) |
| --- | --- | --- | --- |
| 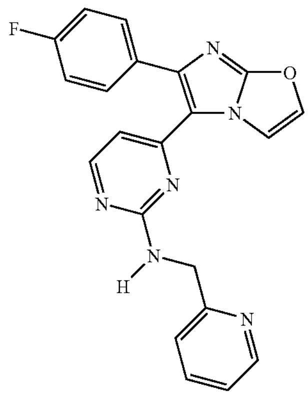 | XLVIII | 74 | 96.8 |
| 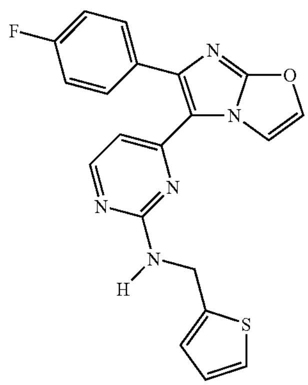 | XLIX | 5.87 | 20 |
| 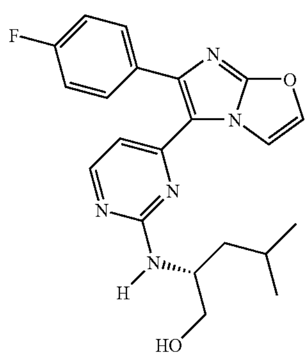 | L | 86.6 | 125 |
| 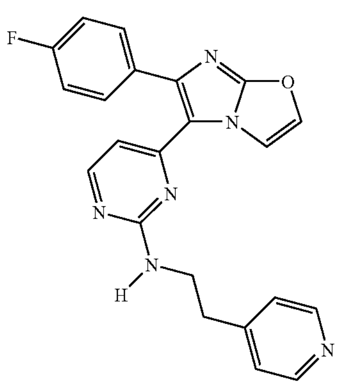 | LI | 8.06 | 94.4 |

TABLE 1-continued
| Structure | Compounds | p38α (ELISA) IC50 (nM) | TNFα (THP-1) IC50 (nM) |
|---|---|---|---|
| 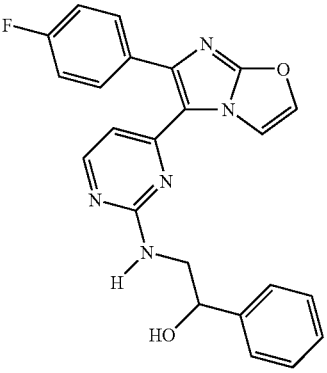 | LII | 54.5 | 60.9 |
| 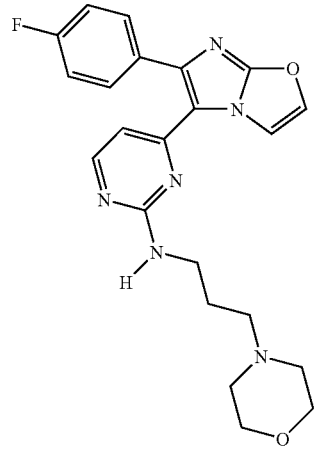 | LIII | 361 | 236 |
| 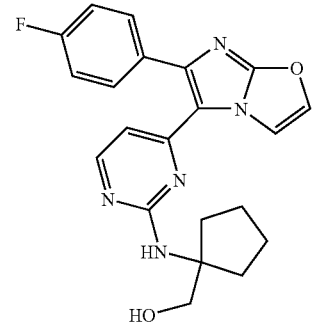 | LIV | 30.2 | 11.8 |

TABLE 1-continued

| Structure | Compounds | p38α (ELISA) IC50 (nM) | TNFα (THP-1) IC50 (nM) |
|---|---|---|---|
| 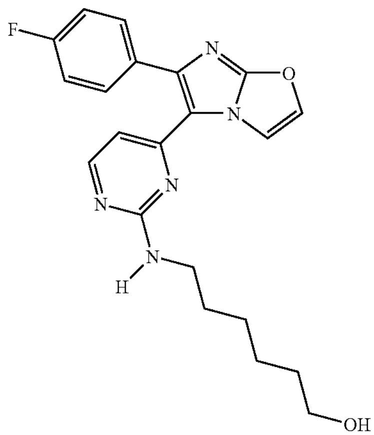 | LV | 23.1 | 25 |
| 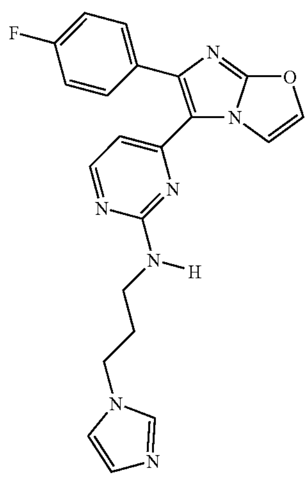 | LVI | 14 | 96.9 |
| Chiral | LVII | 8.96 | 58.5 |

TABLE 1-continued
| Structure | Compounds | p38α (ELISA) IC50 (nM) | TNFα (THP-1) IC50 (nM) |
|---|---|---|---|
| Chiral 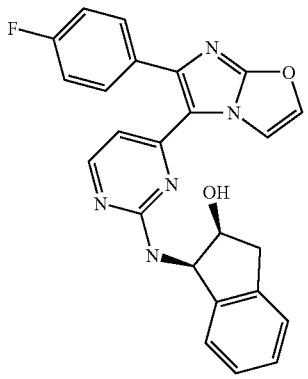 | LVIII | 97.9 | 1190 |
| 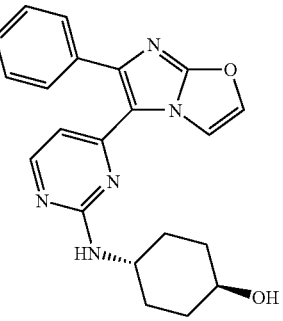 | LIX | 1.79 | 55.4 |
| 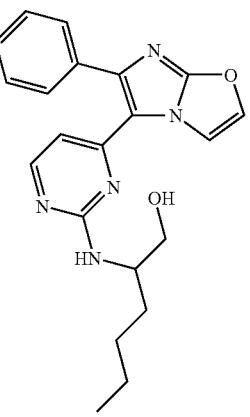 | LX | 20.5 | 69.7 |
| 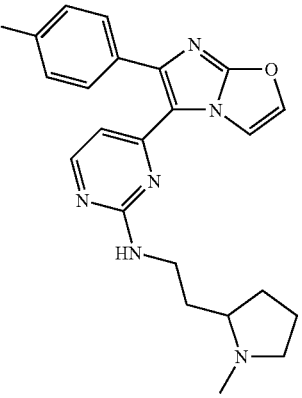 | LXI | 650 | |

TABLE 1-continued

| Structure | Compounds | p38α (ELISA) IC50 (nM) | TNFα (THP-1) IC50 (nM) |
| --- | --- | --- | --- |
| Chiral | LXII | 453 | 258 |
| Chiral | LXIII | 38.5 | 87.4 |
| Chiral | LXIV | 174 | 13.2 |

TABLE 1-continued

| Structure | Compounds | p38α (ELISA) IC50 (nM) | TNFα (THP-1) IC50 (nM) |
|---|---|---|---|
| Chiral | LXV | 86.6 | 26.3 |
| 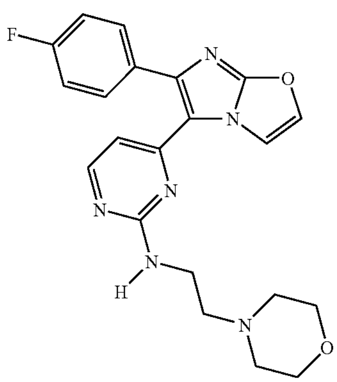 | LXVI | 75.9 | 193 |
| 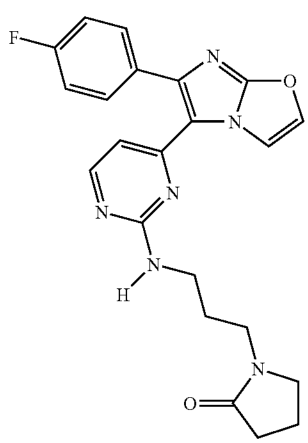 | LXVII | 33.4 | 177 |

TABLE 1-continued
| Structure | Compounds | p38α (ELISA) IC50 (nM) | TNFα (THP-1) IC50 (nM) |
| --- | --- | --- | --- |
| Chiral 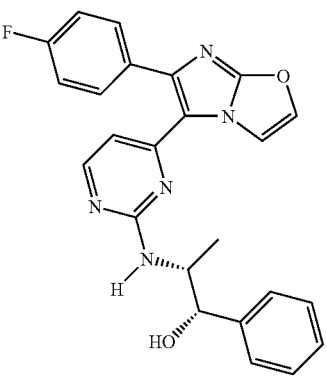 | LXVIII | 79.1 | 140 |
| 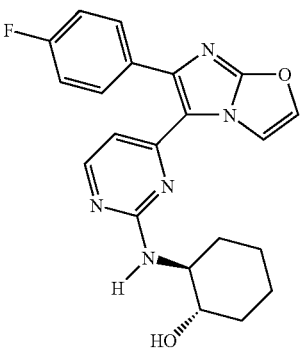 | LXIX | 83.3 | 11.4 |
| 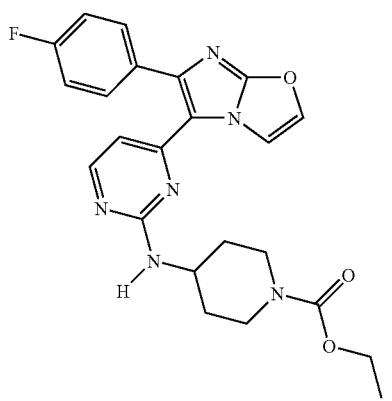 | LXX | 3.33 | 12.2 |

TABLE 1-continued

| Structure | Compounds | p38α (ELISA) IC50 (nM) | TNFα (THP-1) IC50 (nM) |
|---|---|---|---|
| (Chiral structure, S) | LXXI | 27.7 | 19.1 |
| (structure) | LXXII | 664 | |
| (structure) | LXXIII | 234 | 96.6 |

TABLE 1-continued
| Structure | Compounds | p38α (ELISA) IC50 (nM) | TNFα (THP-1) IC50 (nM) |
| --- | --- | --- | --- |
| 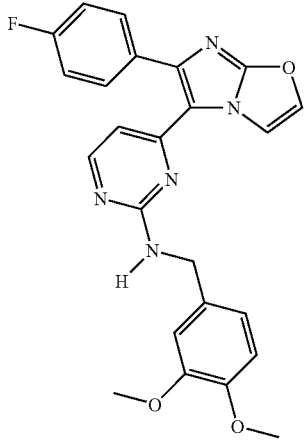 | LXXIV | 72.8 | 519 |
| 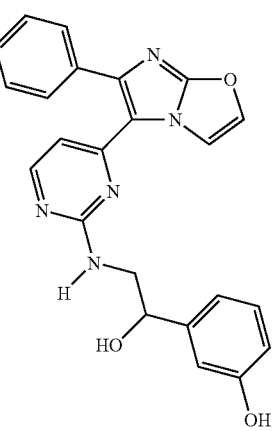 | LXXV | 5.09 | 26.63 |
| 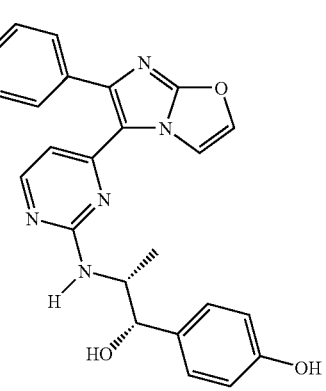 | LXXVI | 6.72 | 41.23 |

TABLE 1-continued

| Structure | Compounds | p38α (ELISA) IC50 (nM) | TNFα (THP-1) IC50 (nM) |
|---|---|---|---|
| 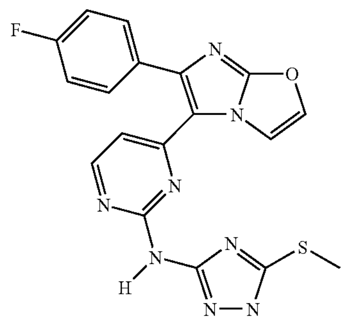 | LXXVII | 529 | |
| 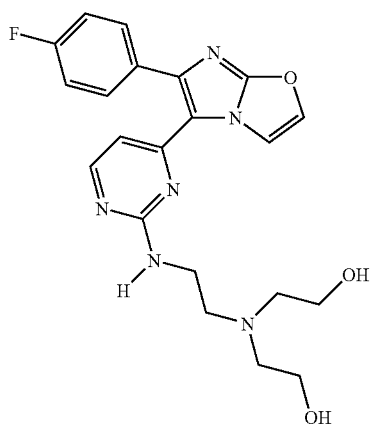 | LXXVIII | 370 | 318 |
| 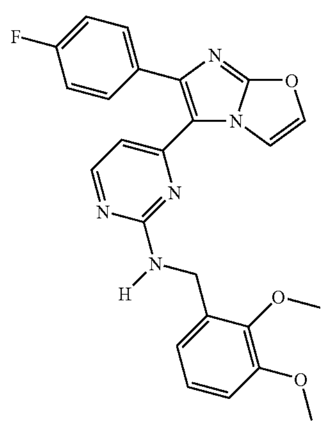 | LXXIX | 342 | 58.4 |
| 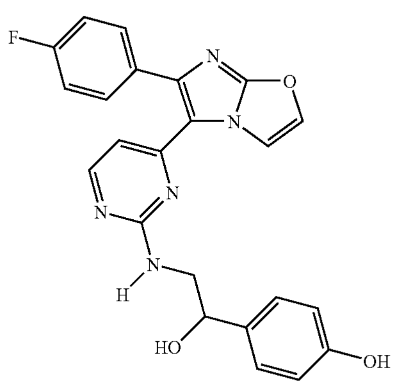 | LXXX | 82.5 | 88.4 |

TABLE 1-continued

| Structure | Compounds | p38α (ELISA) IC50 (nM) | TNFα (THP-1) IC50 (nM) |
|---|---|---|---|
| 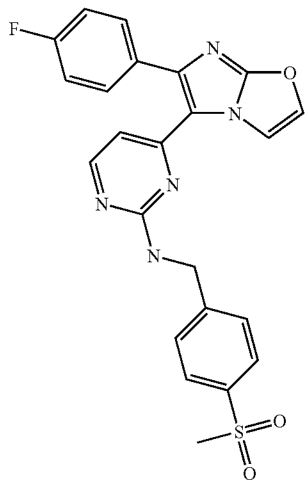 | LXXXI | 1230 | 1230 |
| 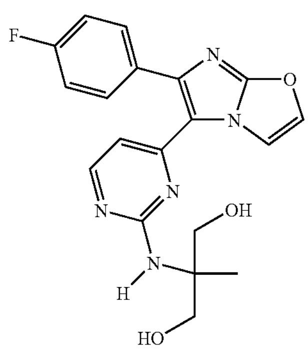 | LXXXII | 184 | 50.5 |
| Chiral | LXXXIII | 185 | 346 |

TABLE 1-continued

| Structure | Compounds | p38α (ELISA) IC50 (nM) | TNFα (THP-1) IC50 (nM) |
|---|---|---|---|
| Racemic | LXXXIV | 15.0 | 9.28 |
| 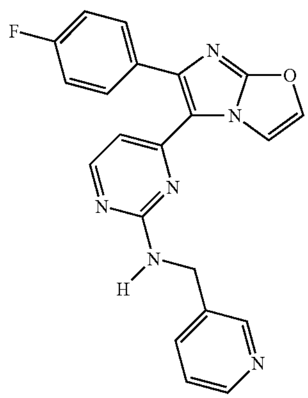 | LXXXV | 66.3 | 39.3 |
| 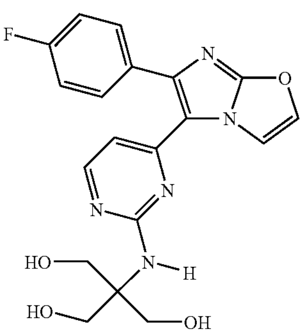 | LXXXVI | 227 | 150 |
| Chiral | LXXXVII | 8.7 | 1.87 |

TABLE 1-continued
| Structure | Compounds | p38α (ELISA) IC50 (nM) | TNFα (THP-1) IC50 (nM) |
|---|---|---|---|
| 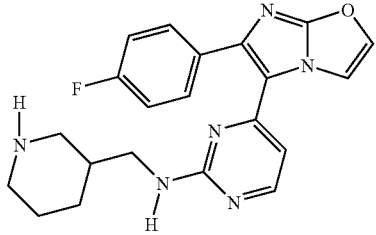 | LXXXVIII | 39.9 | 87 |
| 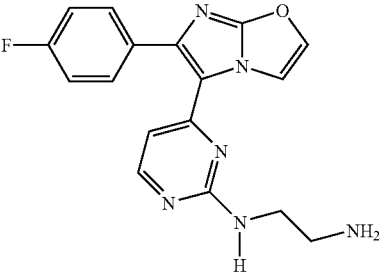 | LXXXIX | 253 | 599 |
| 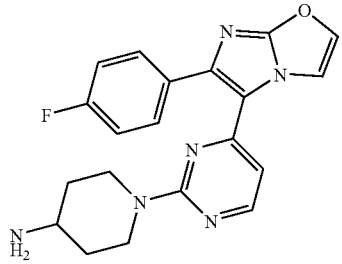 | XC | 866 | |
| 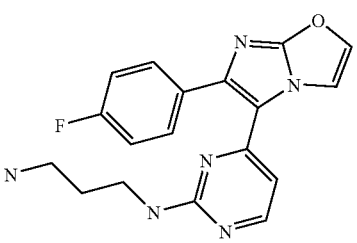 | XCI | 49.9 | 188 |
| 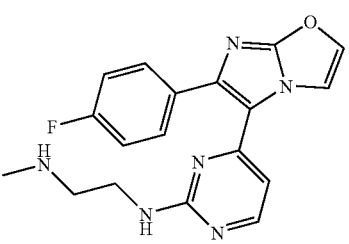 | XCII | 3330 | |

TABLE 1-continued
| Structure | Compounds | p38α (ELISA) IC50 (nM) | TNFα (THP-1) IC50 (nM) |
|---|---|---|---|
| 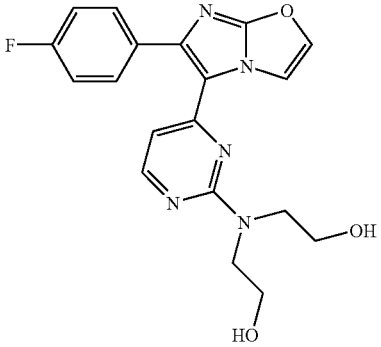 | XCIII | 120 | 457 |
| 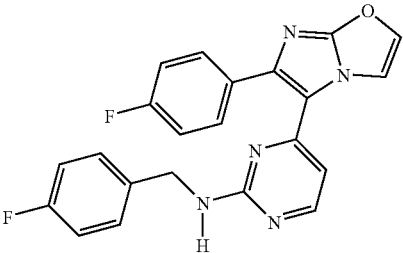 | XCIV | 90.9 | 394 |
| 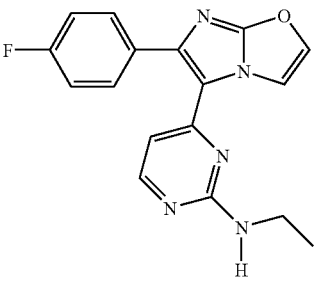 | XCV | 3.42 | 18 |
| 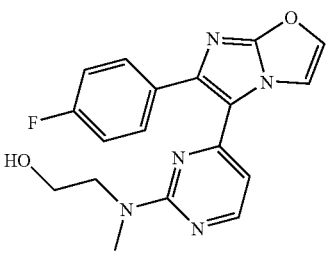 | XCVI | 969 | |
| 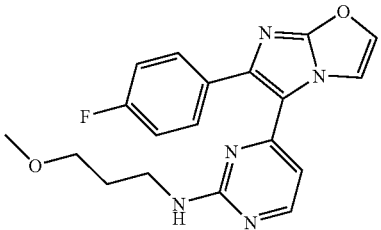 | XCVII | 1.41 | 12.1 |

TABLE 1-continued

| Structure | Compounds | p38α (ELISA) IC50 (nM) | TNFα (THP-1) IC50 (nM) |
| --- | --- | --- | --- |
| 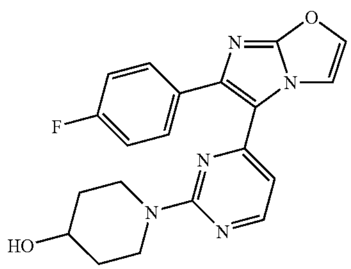 | XCVIII | 134 | 951 |
| 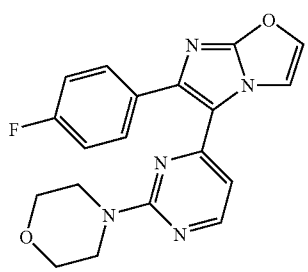 | XCIX | 71.1 | 854 |
| 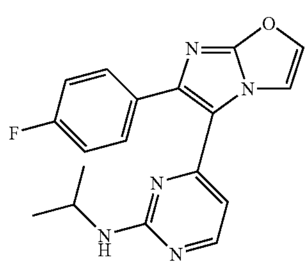 | C | 0.893 | 3.19 |
| Chiral | CI | 1420 | |
| Chiral | CII | 927 | |

TABLE 1-continued

| Structure | Compounds | p38α (ELISA) IC50 (nM) | TNFα (THP-1) IC50 (nM) |
|---|---|---|---|
| 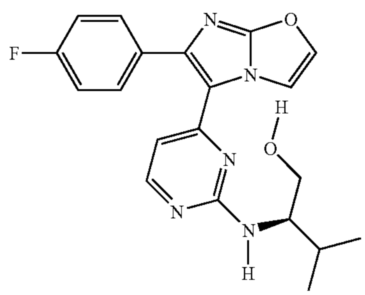 | CIII | 7.57 | 20 |
| 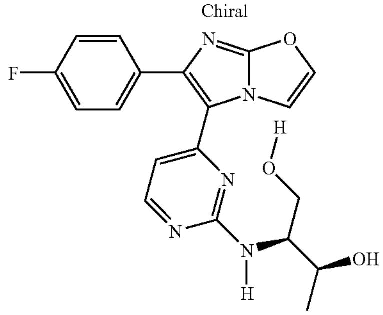 | CIV | 8.62 | 6 |
| 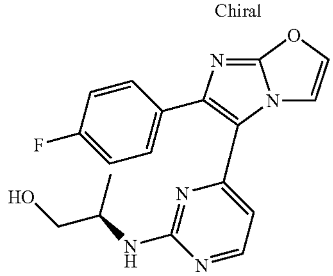 | CV | 3.09 | 8.67 |
| 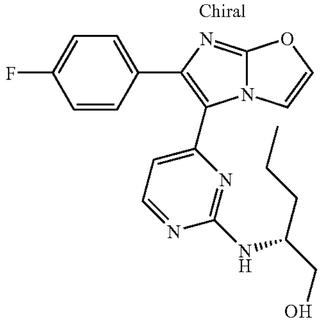 | CVI | 5.2 | 30.6 |

TABLE 1-continued

| Structure | Compounds | p38α (ELISA) IC50 (nM) | TNFα (THP-1) IC50 (nM) |
|---|---|---|---|
| (Chiral structure with 4-fluorophenyl imidazo-oxazole, pyrimidine, NH-CH(CH3)-CH(OH)-CH2OH) | CVII | 63.8 | 112 |
| (Chiral structure with 4-fluorophenyl imidazo-oxazole, pyrimidine, NH-CH(propyl)-CH2OH) | CVIII | 3.11 | 11.7 |
| (Structure with 4-fluorophenyl imidazo-oxazole, pyrimidine, NH-C(Et)(CH2OH)2) | CIX | 30.5 | 19.8 |
| (Structure with 4-fluorophenyl imidazo-oxazole, pyrimidine, NH-cyclohexyl-OH) | CX | 21.8 | 15 |

TABLE 1-continued
| Structure | Compounds | p38α (ELISA) IC50 (nM) | TNFα (THP-1) IC50 (nM) |
|---|---|---|---|
| 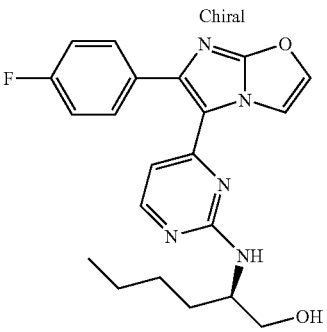 | CXI | 11.2 | 65.9 |
| 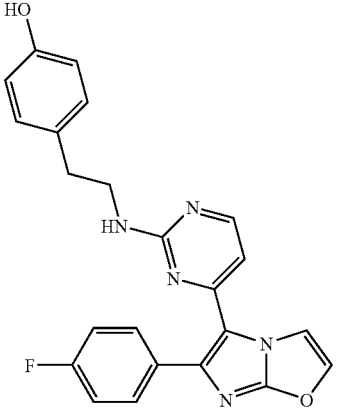 | CXII | 3.45 | 13.12 |
| 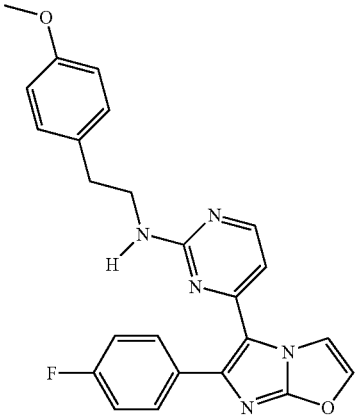 | CXIII | 7.88 | 127 |
| 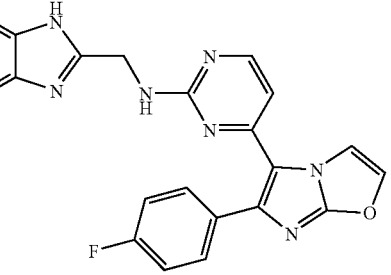 | CXIV | 183 | 913 |

TABLE 1-continued
| Structure | Compounds | p38α (ELISA) IC50 (nM) | TNFα (THP-1) IC50 (nM) |
|---|---|---|---|
| 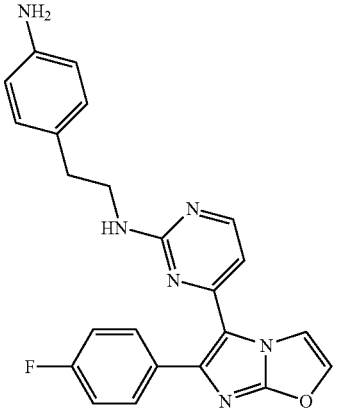 | CXV | 1.73 | 41.9 |
| 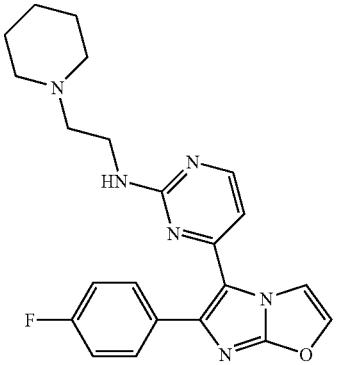 | CXVI | 236 | 376 |
| 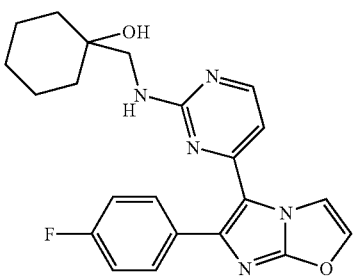 | CXVII | 20.6 | 47 |
| 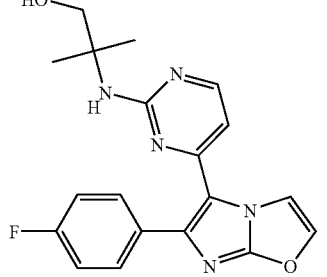 | CXVIII | 2.91 | 26.3 |

TABLE 1-continued

| Structure | Compounds | p38α (ELISA) IC50 (nM) | TNFα (THP-1) IC50 (nM) |
|---|---|---|---|
| 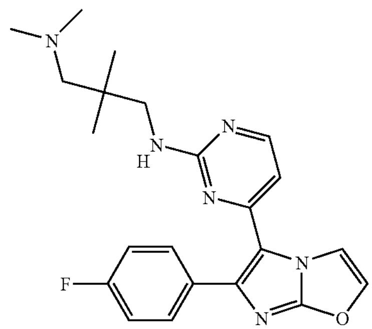 | CXIX | 17 | 33.1 |
| 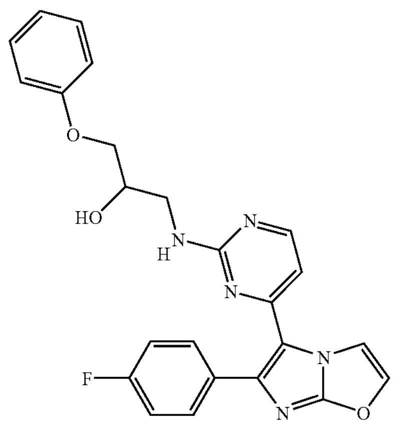 | CXX | 36.5 | 171 |
| 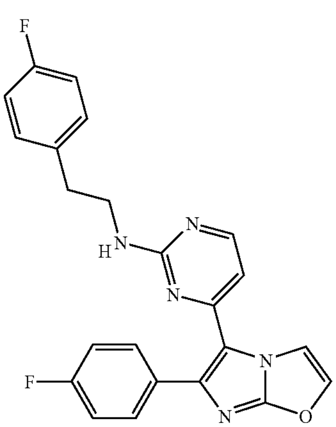 | CXXI | 11.2 | 26.4 |

TABLE 1-continued

| Structure | Compounds | p38α (ELISA) IC50 (nM) | TNFα (THP-1) IC50 (nM) |
| --- | --- | --- | --- |
| 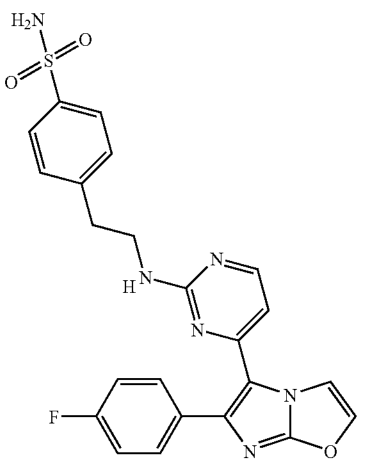 | CXXII | 5.44 | 22.7 |
| 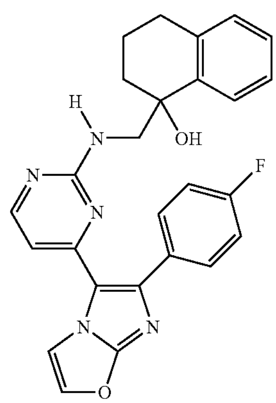 | CXXIII | 27.2 | 99 |
| 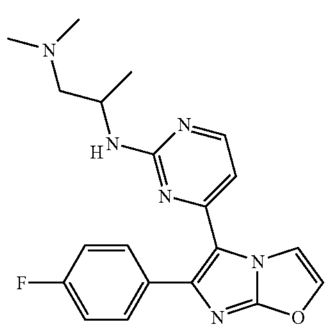 | CXXIV | 59.6 | 67.7 |

TABLE 1-continued
| Structure | Compounds | p38α (ELISA) IC50 (nM) | TNFα (THP-1) IC50 (nM) |
|---|---|---|---|
| 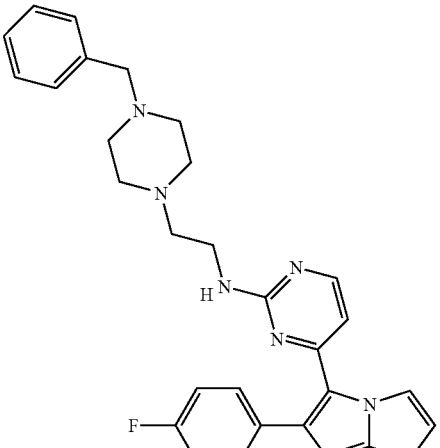 | CXXV | 258 | 1360 |
| Chiral 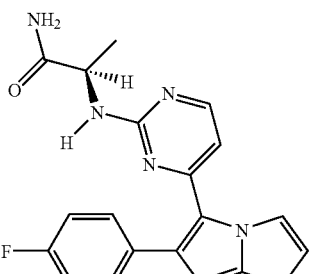 | CXXVI | 29.4 | 86.1 |
| 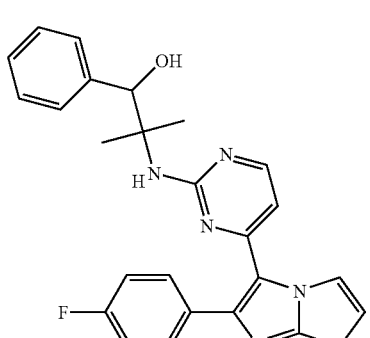 | CXXVII | 28.5 | 249 |
| Chiral 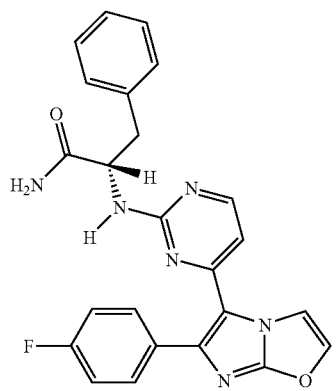 | CXXVIII | 71 | 1390 |

TABLE 1-continued
| Structure | Compounds | p38α (ELISA) IC50 (nM) | TNFα (THP-1) IC50 (nM) |
|---|---|---|---|
| 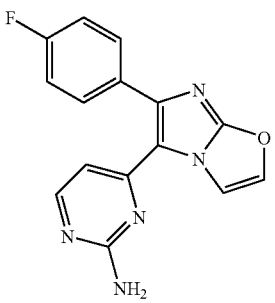 | CXXIX | 97.4 | |
| 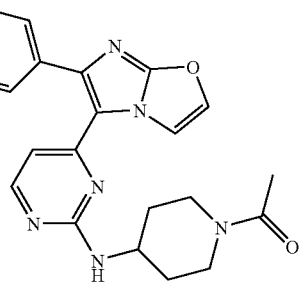 | CCLXXVIII | 2.38 | 9.26 |
| 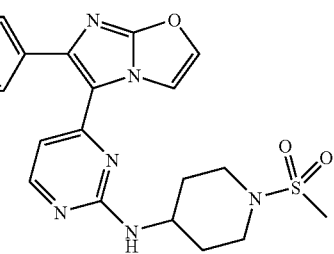 | CCLXXIX | 0.71 | 5.1 |
| 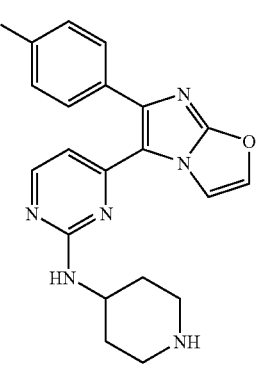 | CCLXXX | 13.05 | 7.89 |

TABLE 1-continued

| Structure | Compounds | p38α (ELISA) IC50 (nM) | TNFα (THP-1) IC50 (nM) |
|---|---|---|---|
| 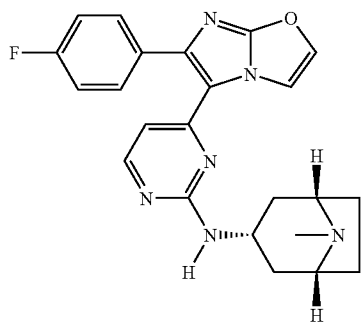 | CCLXXXI | 4.91 | 3.64 |
| 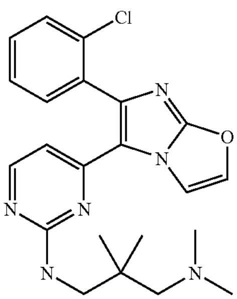 | CCLXXXII | 44.8 | 88.4 |
| 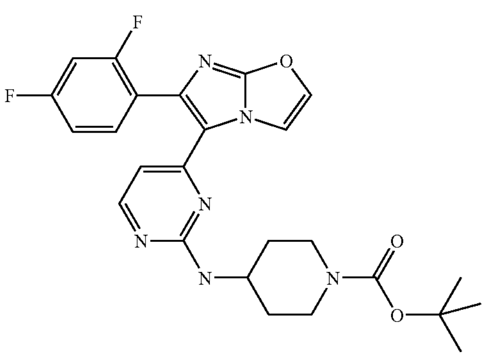 | CCLXXXIII | 1.1 | 52.7 |
| 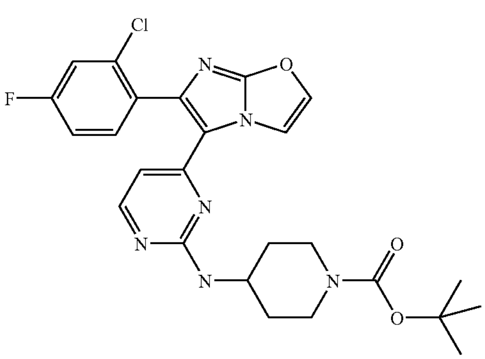 | CCLXXXIV | 1.4 | 96.2 |

TABLE 1-continued
| Structure | Compounds | p38α (ELISA) IC50 (nM) | TNFα (THP-1) IC50 (nM) |
|---|---|---|---|
| 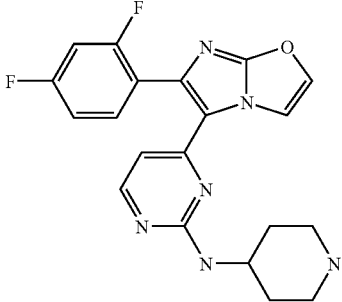 | CCLXXXV | 3.3 | 9.9 |
| 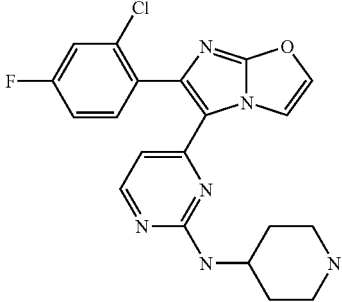 | CCLXXXVI | 7 | 67.3 |
| 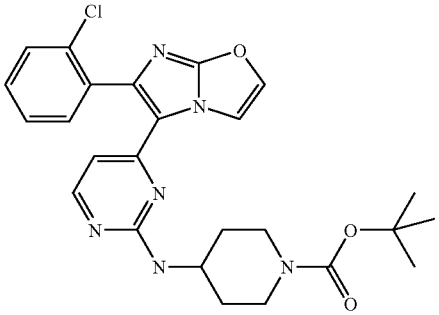 | CCLXXXVII | 8.2 | 170 |
| 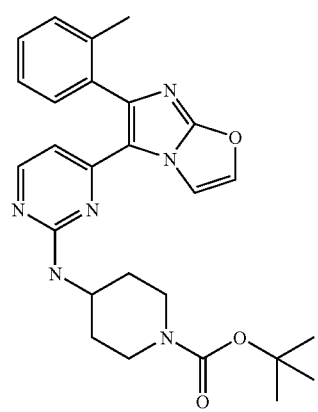 | CCLXXXVIII | 4.8 | 211 |

TABLE 1-continued

| Structure | Compounds | p38α (ELISA) IC50 (nM) | TNFα (THP-1) IC50 (nM) |
|---|---|---|---|
| Chiral | CCLXXXIX | 1.3 | 3.2 |
| Chiral | CCXC | 6.8 | 72 |
| Chiral | CCXCI | 11.2 | 77 |
| Chiral | CCXCII | 16.3 | 47.8 |

TABLE 1-continued

| Structure | Compounds | p38α (ELISA) IC50 (nM) | TNFα (THP-1) IC50 (nM) |
|---|---|---|---|
| Chiral | CCXCIII | 4.9 | 172 |
| Chiral | CCXCIV | 16.4 | 90 |
| Chiral | CCXCV | 9.7 | 8.7 |
| 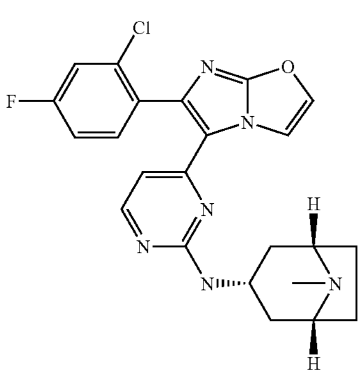 | CCXCVI | 3.6 | 15.5 |

TABLE 1-continued

| Structure | Compounds | p38α (ELISA) IC50 (nM) | TNFα (THP-1) IC50 (nM) |
| --- | --- | --- | --- |
| 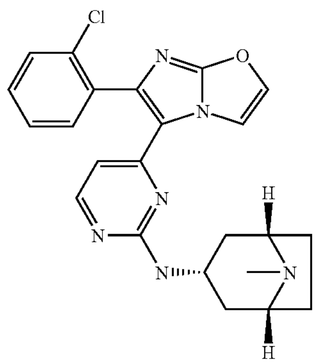 | CCXCVII | 6.8 | 24.4 |
| 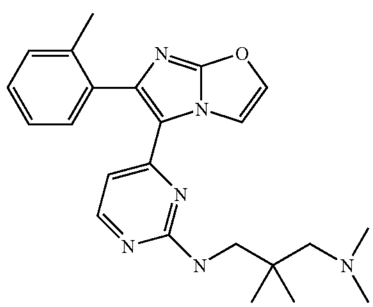 | CCXCVIII | 52.2 | 85.1 |
| 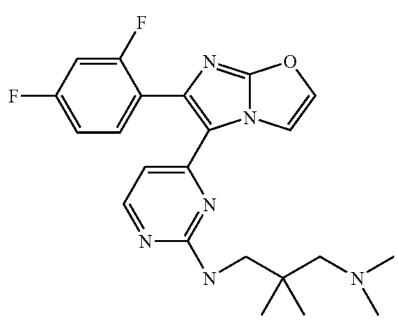 | CCXCIX | 6.1 | 17.8 |
| 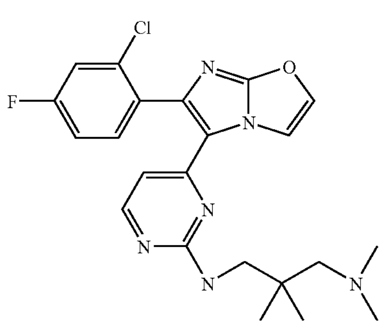 | CCXCX | 20.3 | 78.2 |

TABLE 1-continued

| Structure | Compounds | p38α (ELISA) IC50 (nM) | TNFα (THP-1) IC50 (nM) |
|---|---|---|---|
| 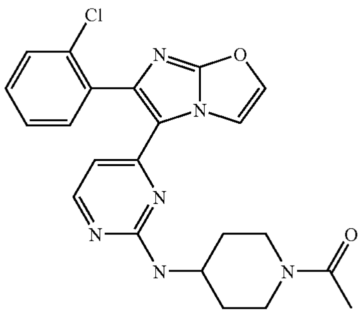 | CCCI | 2.3 | 38.5 |
| Chiral | CCCII | 13.8 | 5.5 |
| Chiral | CCCIII | 12.5 | 9 |
| Chiral | CCCIV | 3.8 | 1.7 |

TABLE 1-continued
| Structure | Compounds | p38α (ELISA) IC50 (nM) | TNFα (THP-1) IC50 (nM) |
|---|---|---|---|
| 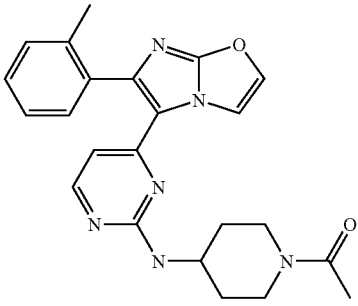 | CCCV | 4.8 | 41 |
| 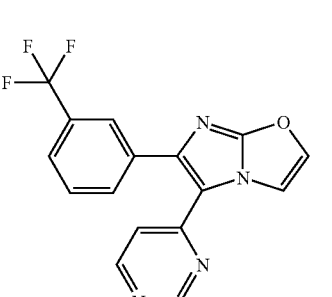 | CCCVI | 4.9 | 82.6 |
| 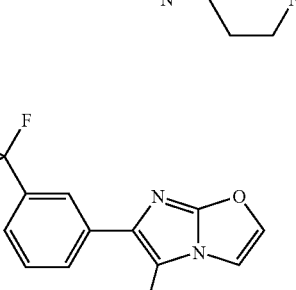 | CCCVII | 43.3 | 136 |
| 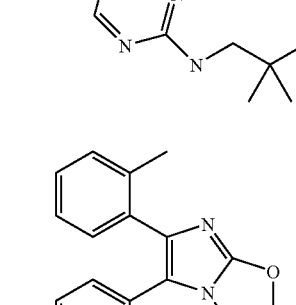 | CCCVIII | 10 | 24 |

TABLE 1-continued

| Structure | Compounds | p38α (ELISA) IC50 (nM) | TNFα (THP-1) IC50 (nM) |
|---|---|---|---|
| 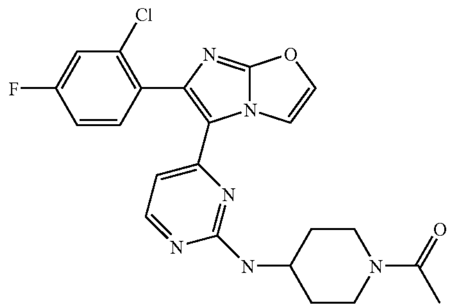 | CCCIX | 1.3 | 6.5 |
| 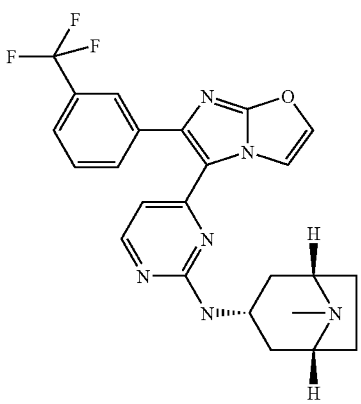 | CCCX | 9.3 | 47.9 |
| 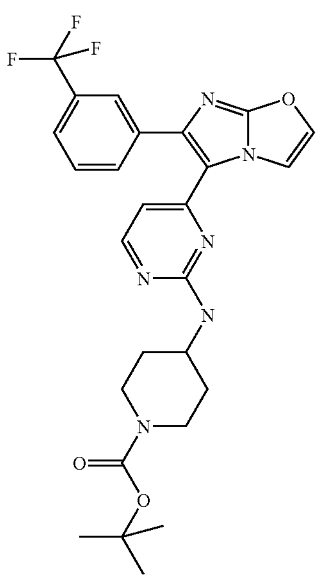 | CCCXI | 18 | 611 |

TABLE 1-continued
| Structure | Compounds | p38α (ELISA) IC50 (nM) | TNFα (THP-1) IC50 (nM) |
|---|---|---|---|
| 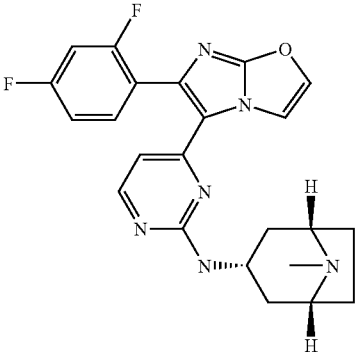 | CCCXII | 2.6 | 1.2 |
| 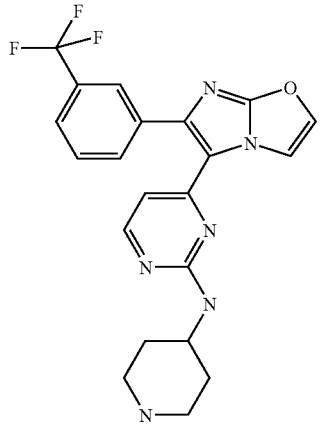 | CCCXIII | 21.2 | 111 |
| 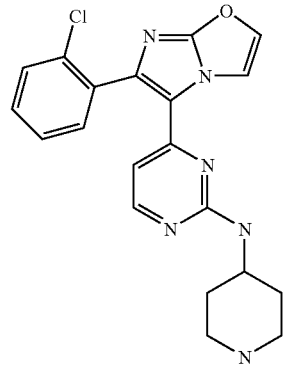 | CCCXIV | 14.5 | 24.6 |
| 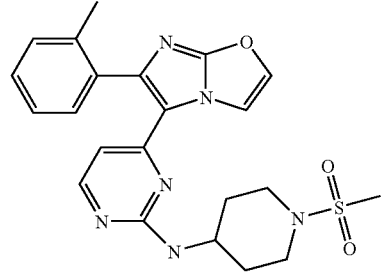 | CCCXV | | |

TABLE 1-continued

| Structure | Compounds | p38α (ELISA) IC50 (nM) | TNFα (THP-1) IC50 (nM) |
| --- | --- | --- | --- |
| 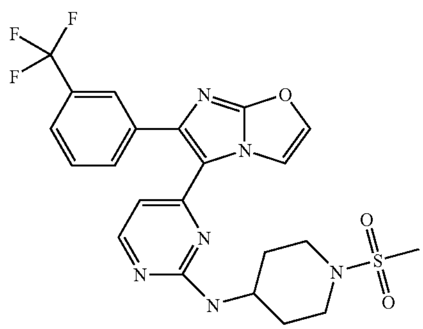 | CCCXVI | 0.9 | 33.7 |
| 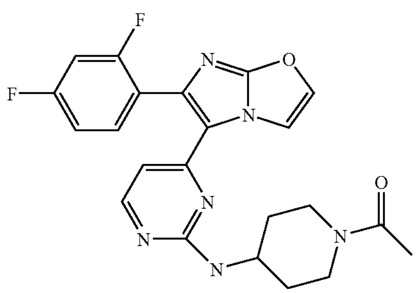 | CCCXVII | 3 | 13.7 |
| 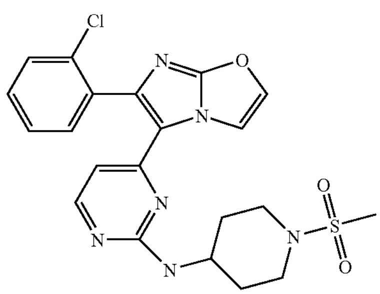 | CCCXVIII | 1 | 18.2 |
| 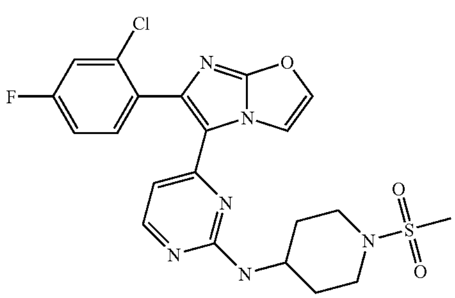 | CCCXIX | 0.3 | 17.7 |
| 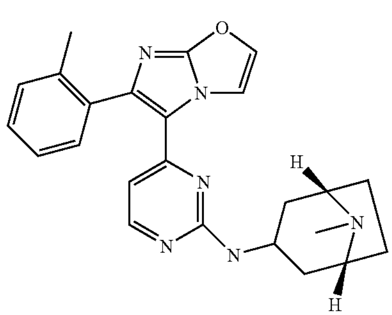 | CCCXX | 13.9 | 23.7 |

TABLE 1-continued

| Structure | Compounds | p38α (ELISA) IC50 (nM) | TNFα (THP-1) IC50 (nM) |
|---|---|---|---|
| 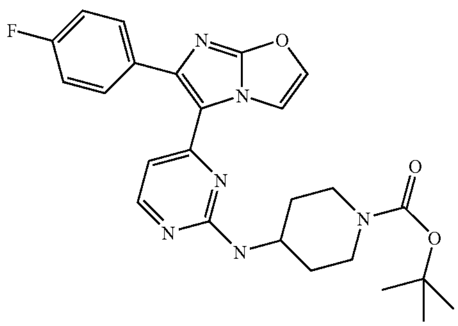 | CCCXXI | | |

TABLE 2

| Structure | Compounds | p38α (ELISA) IC50 (nM) | TNFα (THP-1) IC50 (nM) |
|---|---|---|---|
| 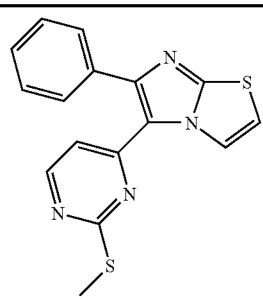 | CXXX | 228.00 | |
| 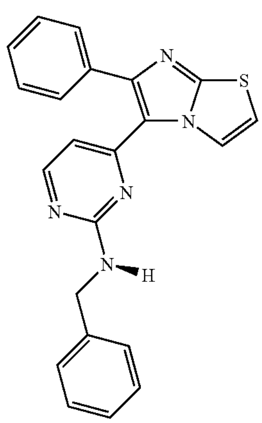 | CXXXI | 28.5 | |
| 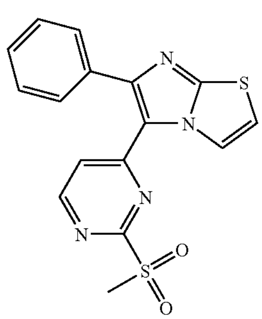 | CXXXII | 373 | >10,000 |

TABLE 2-continued
| Structure | Compounds | p38α (ELISA) IC50 (nM) | TNFα (THP-1) IC50 (nM) |
|---|---|---|---|
| 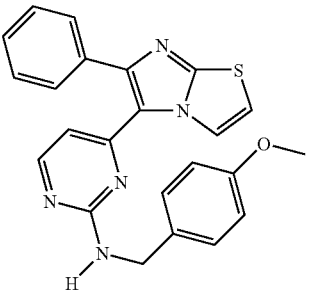 | CXXXIII | 81.4 | |
| 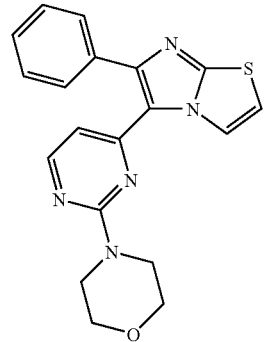 | CXXXIV | 113 | |
| 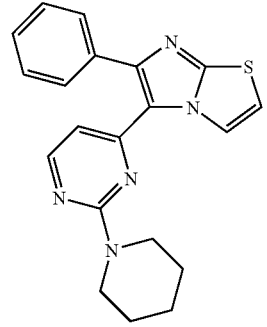 | CXXXV | 396 | |
| 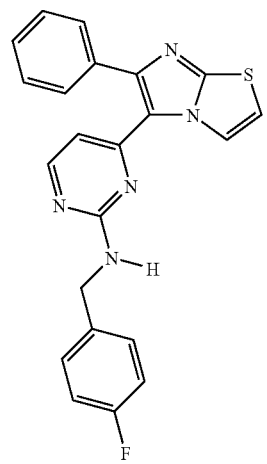 | CXXXVI | 150 | |

TABLE 2-continued
| Structure | Compounds | p38α (ELISA) IC50 (nM) | TNFα (THP-1) IC50 (nM) |
|---|---|---|---|
| 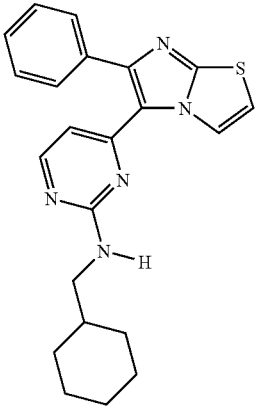 | CXXXVII | 65.7 | |
| 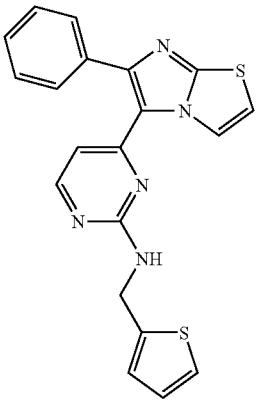 | CXXXVIII | 10.2 | |
| 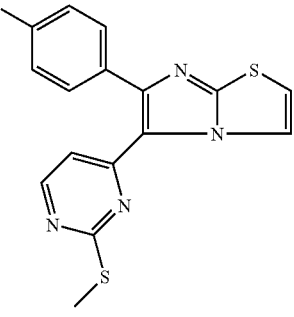 | CXXXIX | 635 | |
| 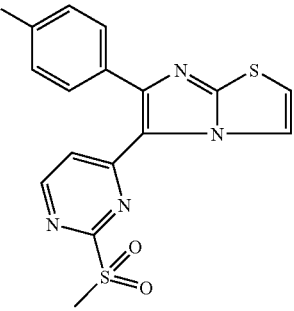 | CXL | 966 | 4860 |

TABLE 2-continued
| Structure | Compounds | p38α (ELISA) IC50 (nM) | TNFα (THP-1) IC50 (nM) |
|---|---|---|---|
| 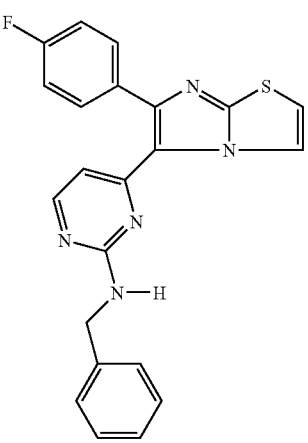 | CXLI | 4.92 | |
| 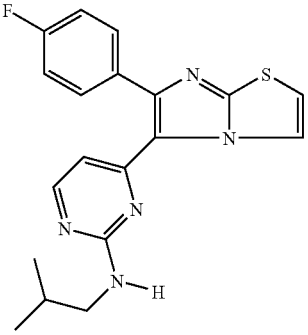 | CXLII | 1.97 | |
| 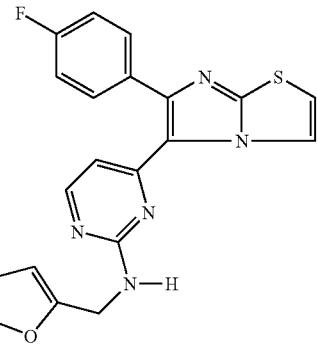 | CXLIII | 8.22 | |
| 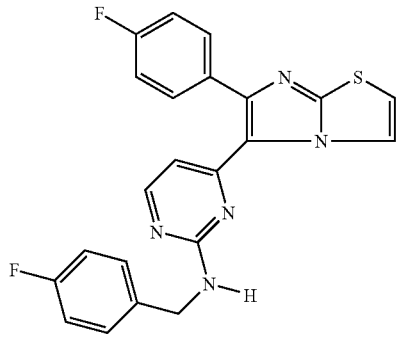 | CXLIV | 54.1 | 182 |

TABLE 2-continued

| Structure | Compounds | p38α (ELISA) IC50 (nM) | TNFα (THP-1) IC50 (nM) |
|---|---|---|---|
| 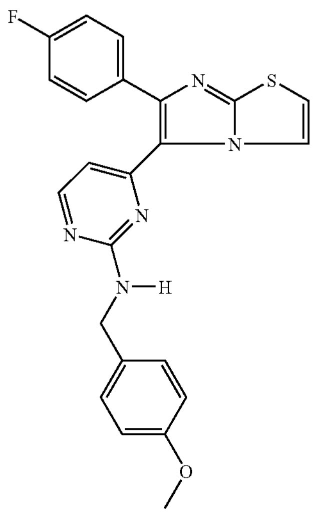 | CXLV | 65.5 | |
| 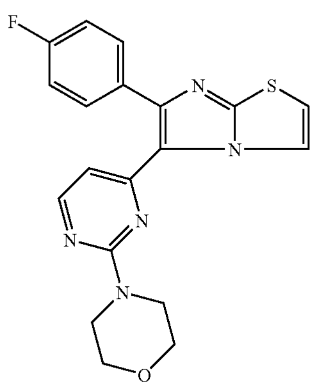 | CXLVI | 129 | |
| 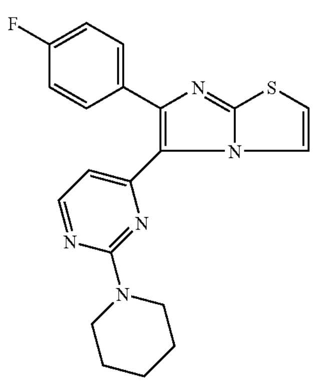 | CXLVII | 527 | |

TABLE 2-continued

| Structure | Compounds | p38α (ELISA) IC50 (nM) | TNFα (THP-1) IC50 (nM) |
|---|---|---|---|
| 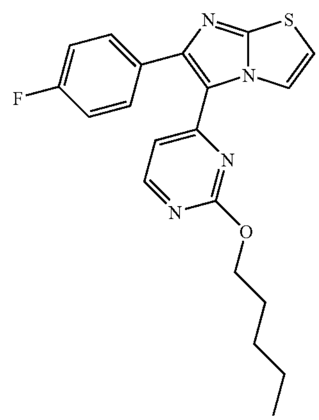 | CXLVII | 890 | |
| 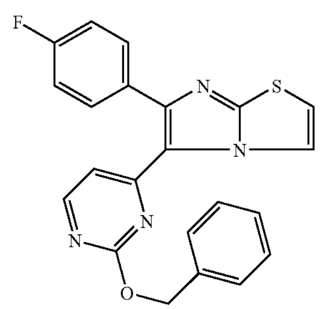 | CXLIX | 152 | 391 |
| 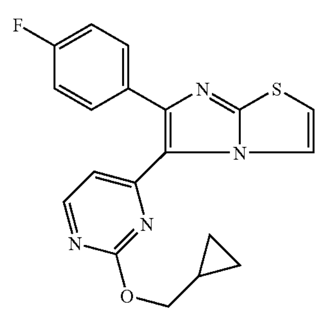 | CL | 256 | 218 |
| 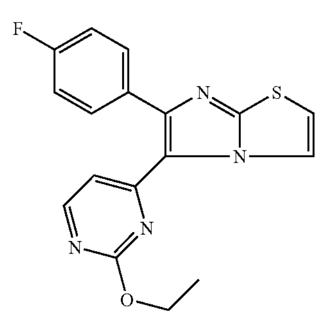 | CLI | 122 | 284 |

TABLE 2-continued

| Structure | Compounds | p38α (ELISA) IC50 (nM) | TNFα (THP-1) IC50 (nM) |
|---|---|---|---|
| 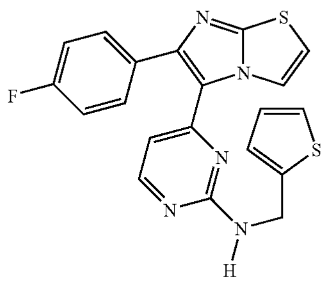 | CLII | 6.14 | |
| 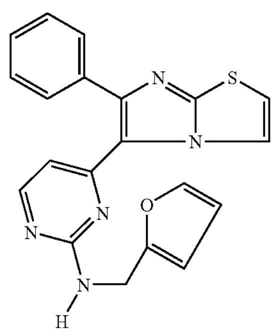 | CLIII | 15.6 | |
| 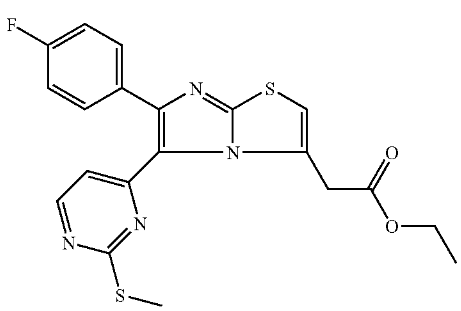 | CLIV | 1000 | |
| 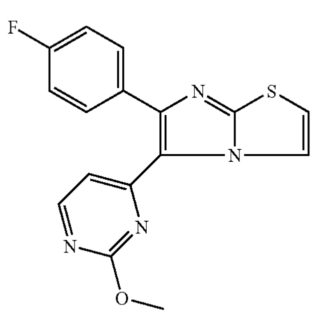 | CLV | 286 | 402 |

TABLE 2-continued

| Structure | Compounds | p38α (ELISA) IC50 (nM) | TNFα (THP-1) IC50 (nM) |
|---|---|---|---|
| 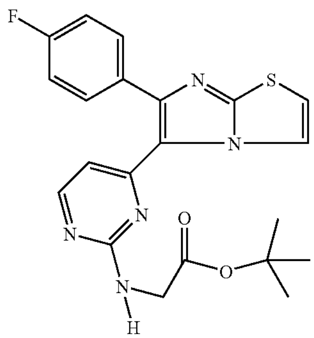 | CLVI | 58.6 | |
| 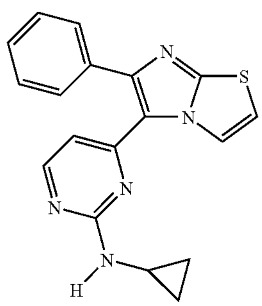 | CLVII | 5.29 | |
| 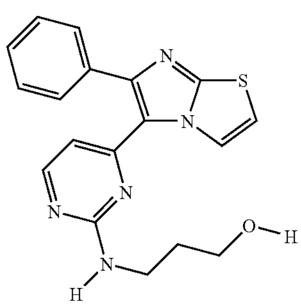 | CLVIII | 21.8 | |
| 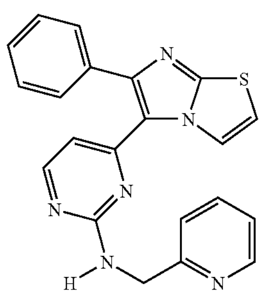 | CLIX | 91.1 | |

TABLE 2-continued
| Structure | Compounds | p38α (ELISA) IC50 (nM) | TNFα (THP-1) IC50 (nM) |
|---|---|---|---|
| 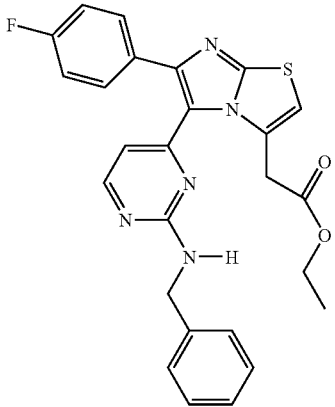 | CLX | 1000 | |
| 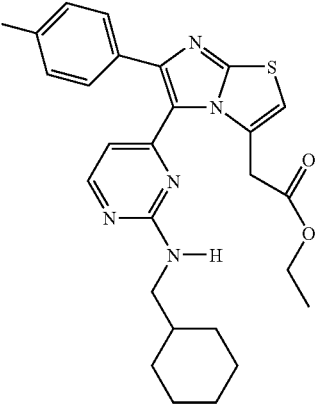 | CLXI | 1000 | |
| 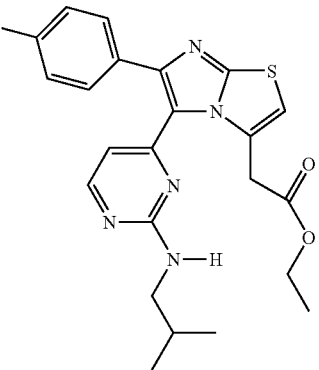 | CLXII | 1000 | |

TABLE 2-continued
| Structure | Compounds | p38α (ELISA) IC50 (nM) | TNFα (THP-1) IC50 (nM) |
|---|---|---|---|
| 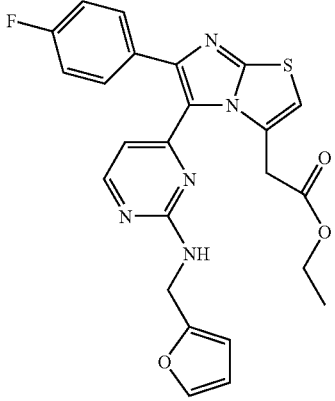 | CLXIII | 1000 | |
| 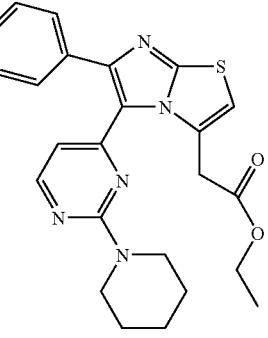 | CLXIV | 1000 | |
| 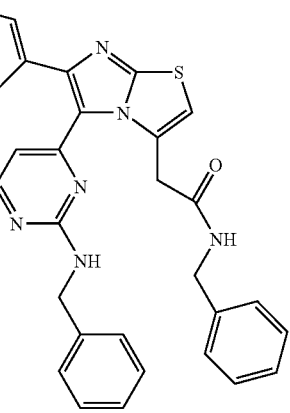 | CLXV | 1000 | |

TABLE 2-continued
| Structure | Compounds | p38α (ELISA) IC50 (nM) | TNFα (THP-1) IC50 (nM) |
|---|---|---|---|
| 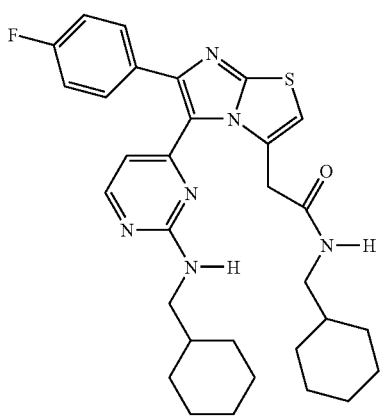 | CLXVI | 1000 | |
| 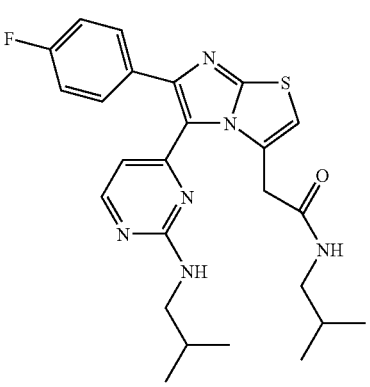 | CLXVII | 1000 | |
| 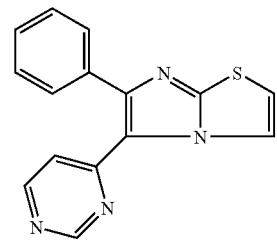 | CLXVIII | 1460 | |
| 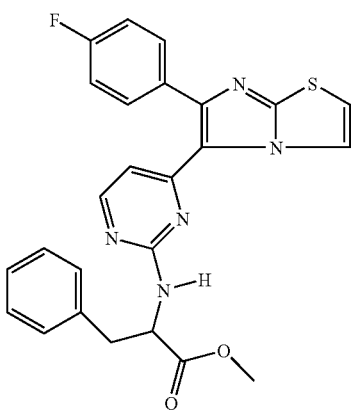 | CLXIX | 267 | |

TABLE 2-continued
| Structure | Compounds | p38α (ELISA) IC50 (nM) | TNFα (THP-1) IC50 (nM) |
|---|---|---|---|
| 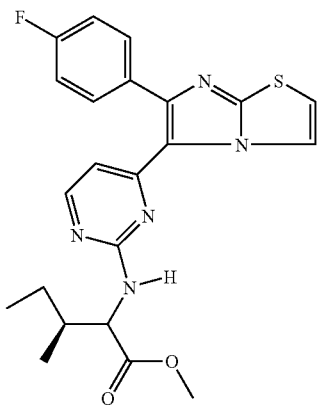 | CLXX | 13.4 | |
| 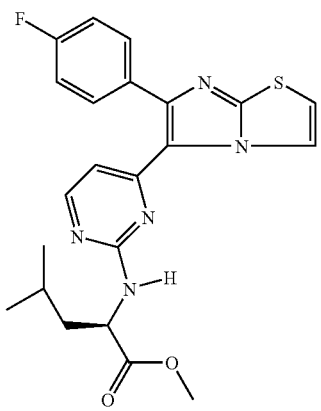 | CLXXI | 14.9 | 3970 |
| 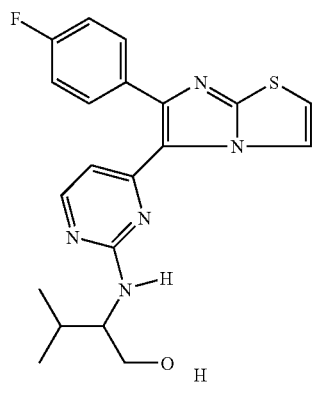 | CLXXII | 4.67 | 48.1 |

TABLE 2-continued

| Structure | Compounds | p38α (ELISA) IC50 (nM) | TNFα (THP-1) IC50 (nM) |
|---|---|---|---|
| 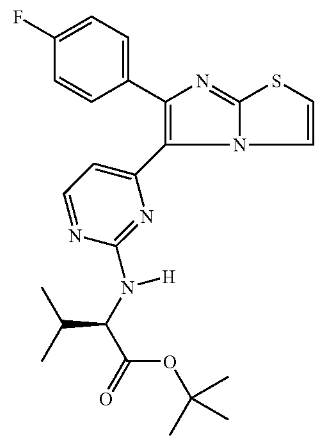 | CLXXIII | 81.4 | |
| 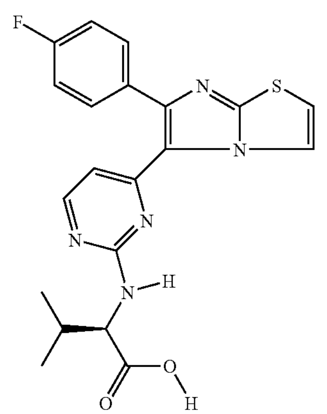 | CLXXIV | 671 | |
| 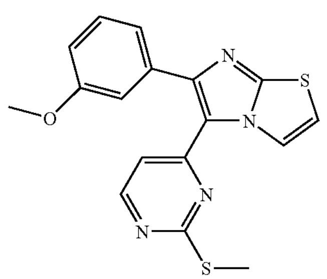 | CLXXV | 3390 | |
| 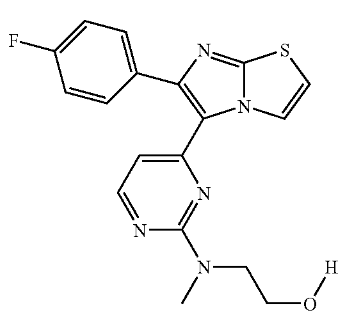 | CLXXVI | 1000 | |

TABLE 2-continued

| Structure | Compounds | p38α (ELISA) IC50 (nM) | TNFα (THP-1) IC50 (nM) |
|---|---|---|---|
| 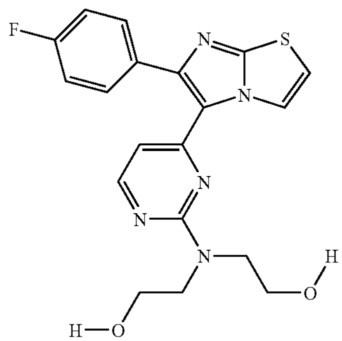 | CLXXVII | 793 | |
| 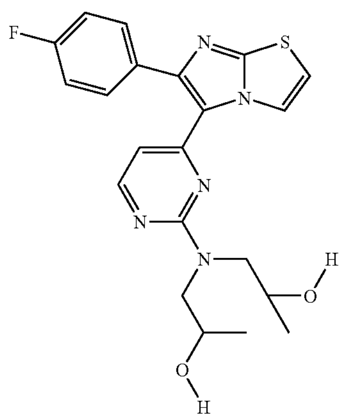 | CLXXVIII | 1000 | |
| 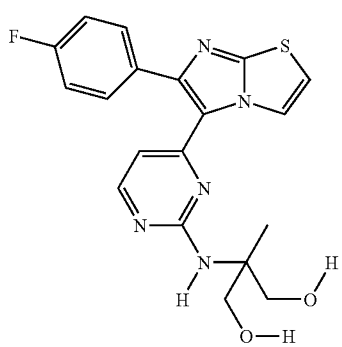 | CLXXIX | 192 | |
| 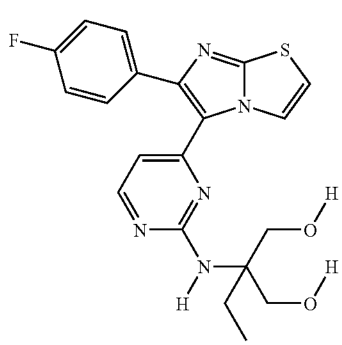 | CLXXX | 80.8 | 57.4 |

TABLE 2-continued
| Structure | | Compounds | p38α (ELISA) IC50 (nM) | TNFα (THP-1) IC50 (nM) |
|---|---|---|---|---|
| 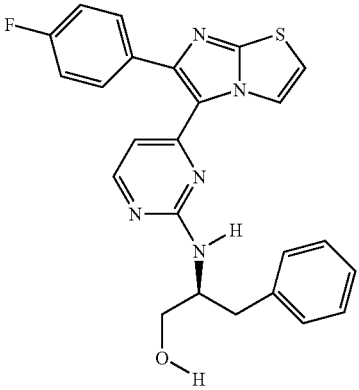 | Chiral | CLXXXI | 176 | 138 |
| 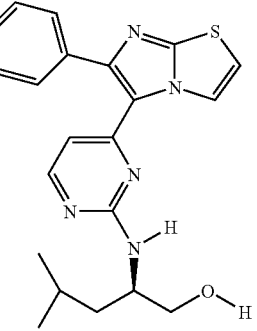 | Chiral | CLXXXII | 347 | |
| 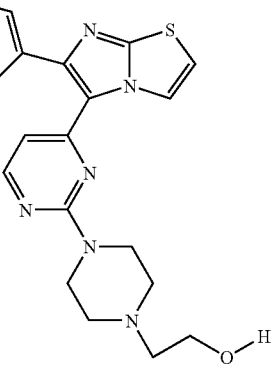 | | CLXXXIII | 1000 | |
| 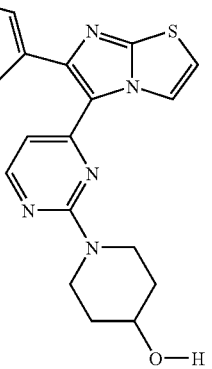 | | CLXXXIV | 594 | |

TABLE 2-continued

| Structure | Compounds | p38α (ELISA) IC50 (nM) | TNFα (THP-1) IC50 (nM) |
|---|---|---|---|
| 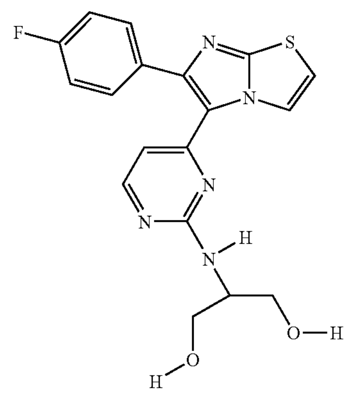 | CLXXXV | 87.1 | |
| 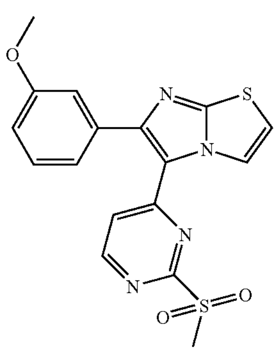 | CLXXXVI | 10000 | |
| 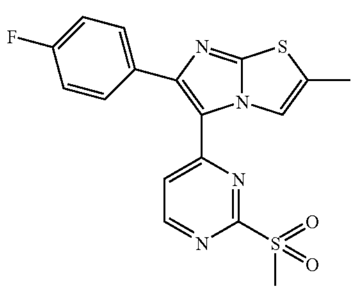 | CLXXXVII | 1850 | |
| 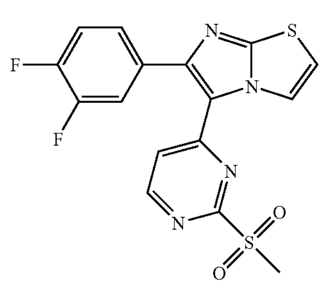 | CLXXXVIII | 10000 | |

TABLE 2-continued

| Structure | Compounds | p38α (ELISA) IC50 (nM) | TNFα (THP-1) IC50 (nM) |
|---|---|---|---|
| 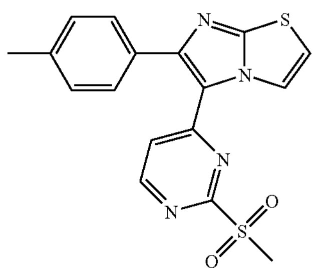 | CLXXXIX | 10000 | |
| 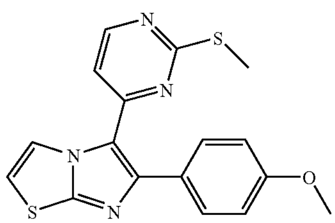 | CXC | 3040 | |
| 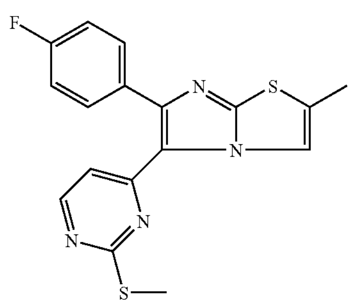 | CXCI | 741 | |
| 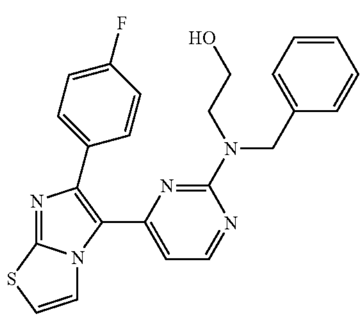 | CXCII | 213 | |
| 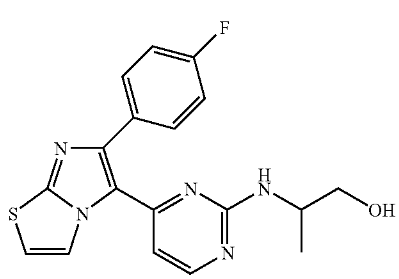 | CXCIII | 6.19 | 8.38 |

TABLE 2-continued

| Structure | Compounds | p38α (ELISA) IC50 (nM) | TNFα (THP-1) IC50 (nM) |
|---|---|---|---|
| Chiral | CXCIV | 565 | |
| 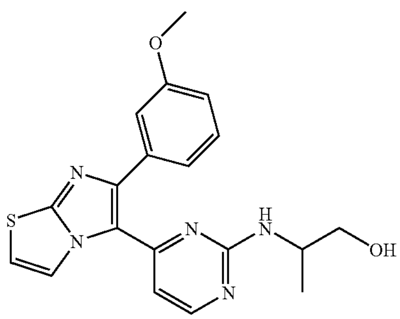 | CXCV | 44.7 | |
| Chiral | CXCVI | 819 | |
| 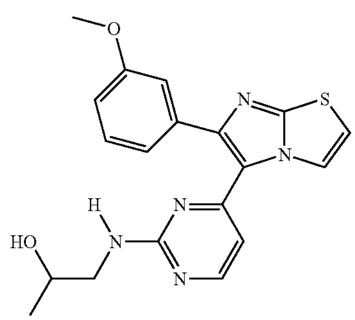 | CXCVII | 61.2 | |

TABLE 2-continued

| Structure | Compounds | p38α (ELISA) IC50 (nM) | TNFα (THP-1) IC50 (nM) |
|---|---|---|---|
| 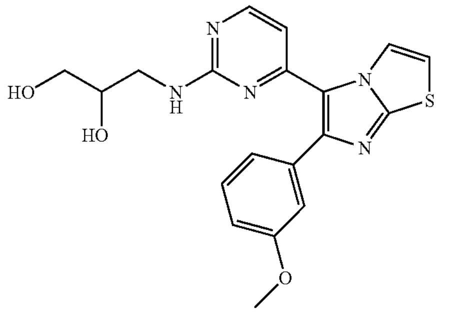 | CXCVIII | 649 | |
| 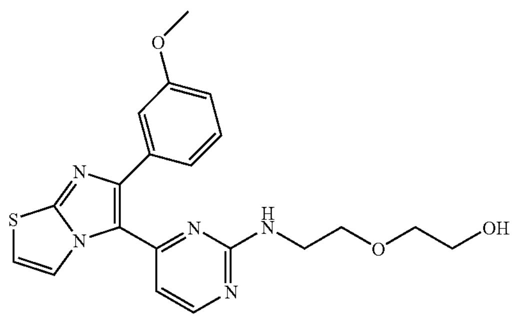 | CXCIX | 428 | |
| Chiral | CC | 112 | 93.8 |
| Chiral | CCI | 75.7 | 101 |

TABLE 2-continued
| Structure | Compounds | p38α (ELISA) IC50 (nM) | TNFα (THP-1) IC50 (nM) |
|---|---|---|---|
| Chiral 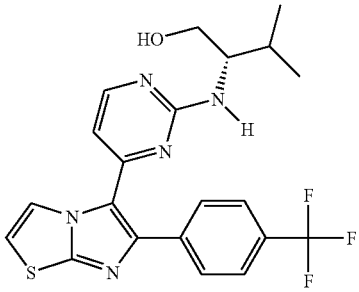 | CCII | 924 | |
| Chiral 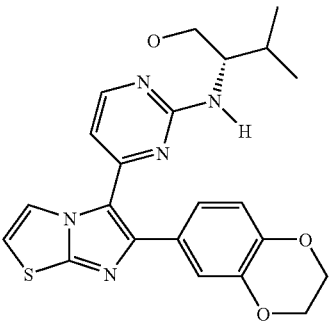 | CCIII | 1410 | |
| 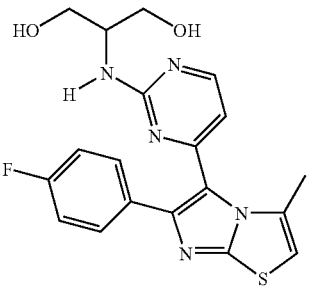 | CCIV | 10100 | |
| Chiral 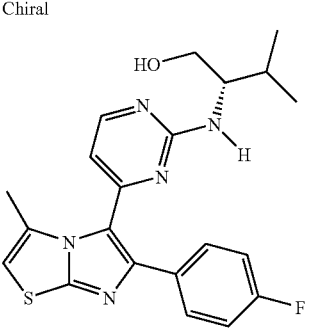 | CCV | 3190 | |

TABLE 2-continued

| Structure | Compounds | p38α (ELISA) IC50 (nM) | TNFα (THP-1) IC50 (nM) |
|---|---|---|---|
| 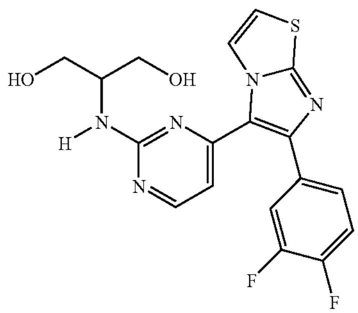 | CCVI | 609 | |
| Chiral | CCVII | 191 | 43.4 |
| 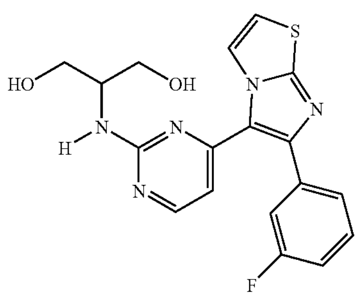 | CCVIII | 971 | |
| Chiral | CCIX | 26 | 55.9 |

TABLE 2-continued
| Structure | Compounds | p38α (ELISA) IC50 (nM) | TNFα (THP-1) IC50 (nM) |
|---|---|---|---|
| 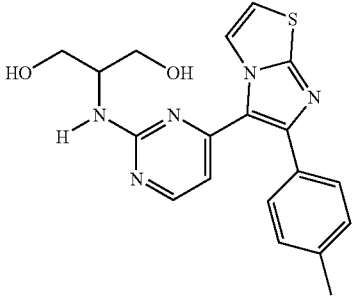 | CCX | 558 | |
| Chiral 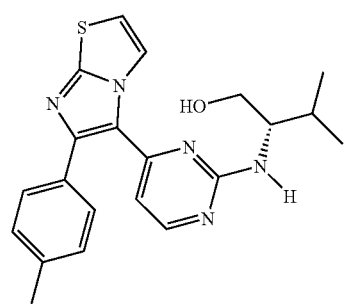 | CCXI | 147 | 58.9 |
| 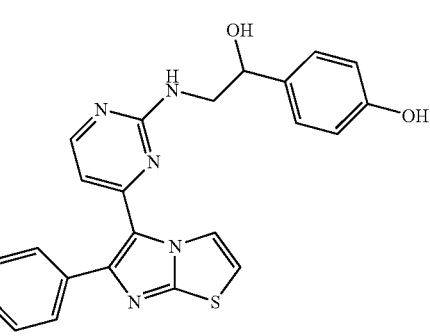 | CCXII | 8.81 | 24.07 |
| 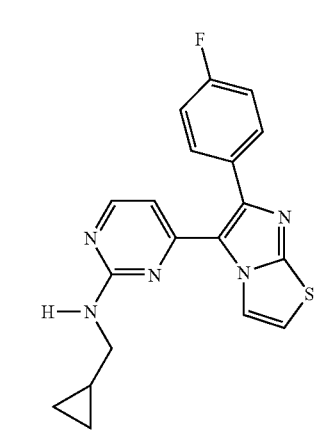 | CCXIII | 13.3 | 5.63 |

TABLE 2-continued
| Structure | Compounds | p38α (ELISA) IC50 (nM) | TNFα (THP-1) IC50 (nM) |
|---|---|---|---|
| 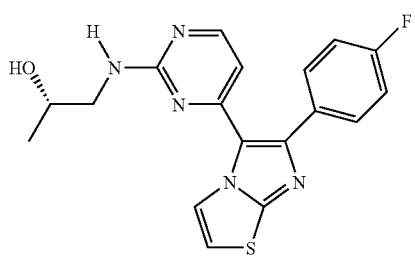 Chiral | CCXIV | 12.1 | 5.03 |
| 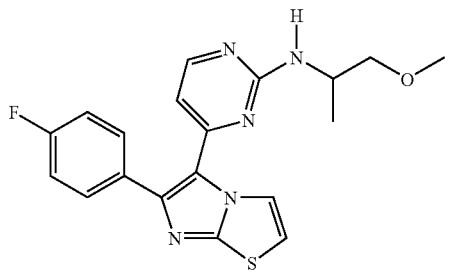 | CCXV | 2.32 | 8.58 |
| 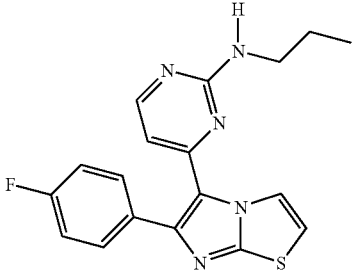 | CCXVI | 4.68 | 5.15 |
| 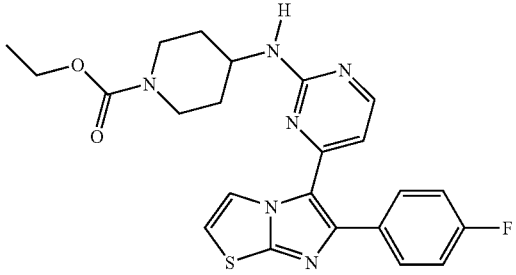 | CCXVII | 1.19 | 7.84 |
| 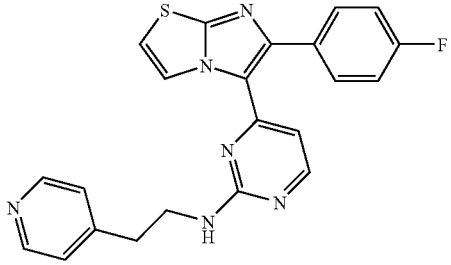 | CCXVIII | 5.87 | 4.46 |

TABLE 2-continued

| Structure | Compounds | p38α (ELISA) IC50 (nM) | TNFα (THP-1) IC50 (nM) |
|---|---|---|---|
| Chiral | CCXIX | 3.03 | 6.84 |
| 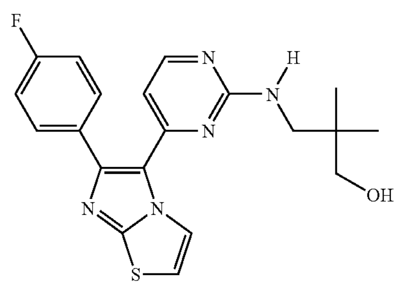 | CCXX | 1.56 | 2.41 |
| 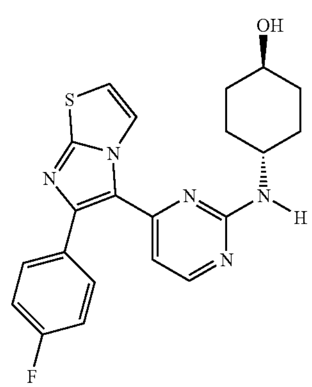 | CCXXI | 1.57 | 5.56 |
| 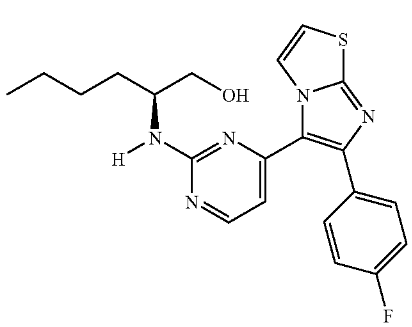 | CCXXII | 5.45 | 49.6 |

TABLE 2-continued

| Structure | Compounds | p38α (ELISA) IC50 (nM) | TNFα (THP-1) IC50 (nM) |
|---|---|---|---|
| 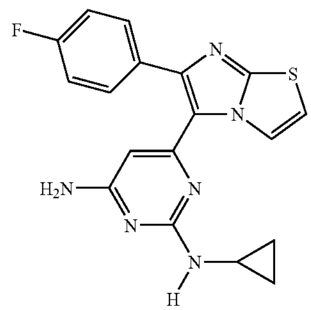 | CCXXIII | 2080 | |
| 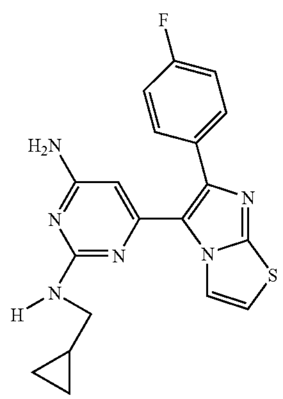 | CCXXIV | 1570 | |
| 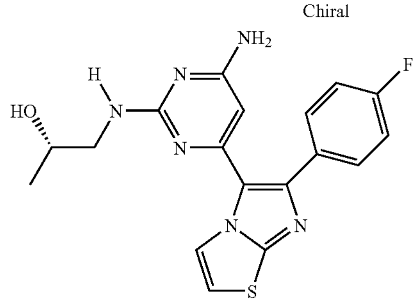 | CCXXV | 1050 | |
| 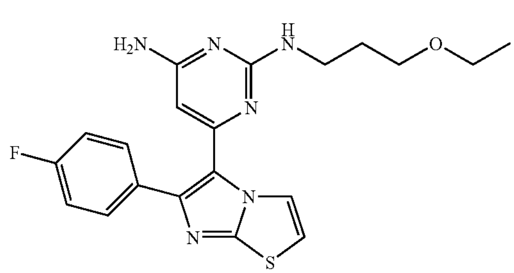 | CCXXVI | 766 | |

TABLE 2-continued

| Structure | Compounds | p38α (ELISA) IC50 (nM) | TNFα (THP-1) IC50 (nM) |
|---|---|---|---|
| 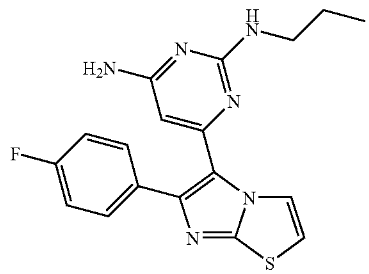 | CCXXVII | 1330 | |
| 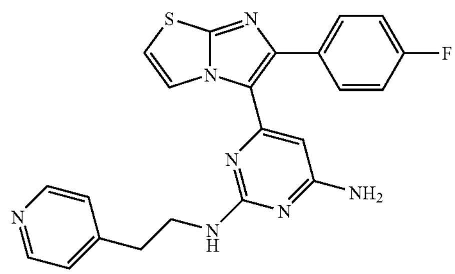 | CCXXVIII | 960 | |
| 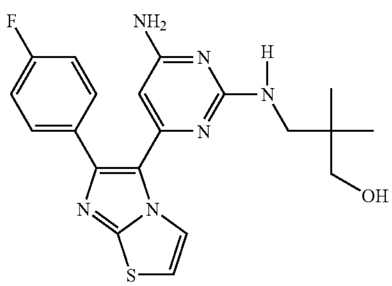 | CCXXIX | 1030 | |
| (Chiral) | CCXXX | 2570 | |

TABLE 2-continued

| Structure | Compounds | p38α (ELISA) IC50 (nM) | TNFα (THP-1) IC50 (nM) |
|---|---|---|---|
| Chiral | CCXXXI | 1.13 | 5.67 |
| Chiral | CCXXXII | 2.06 | 11.1 |
| 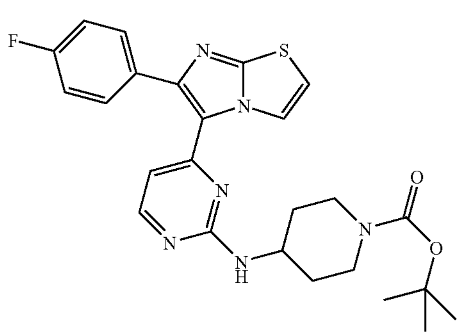 | CCXXXIII | 2.24 | 76.9 |
| 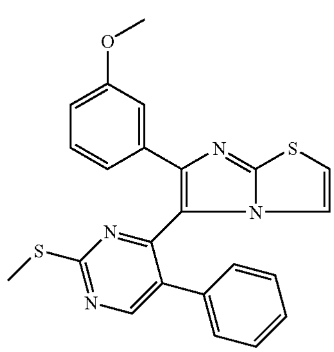 | CCXXXIV | >10000 | >10000 |

TABLE 2-continued

| Structure | Compounds | p38α (ELISA) IC50 (nM) | TNFα (THP-1) IC50 (nM) |
|---|---|---|---|
| Chiral | CCXXXV | 2.08 | 2.95 |
| 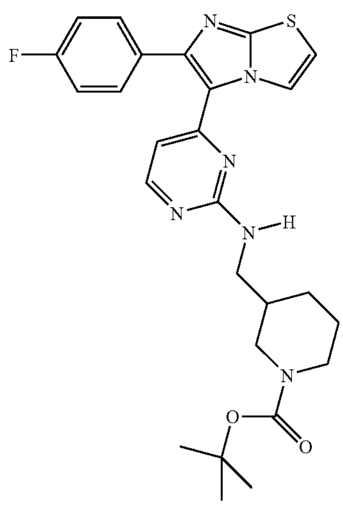 | CCXXXVI | 81.8 | 162 |
| 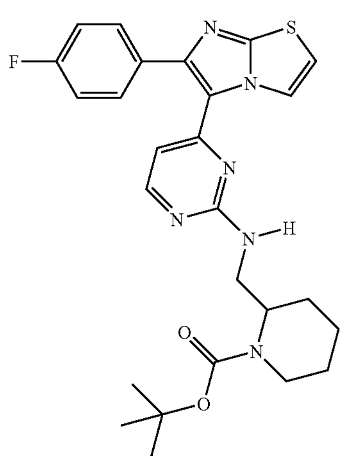 | CCXXXVII | 107 | 113 |

TABLE 2-continued

| Structure | Compounds | p38α (ELISA) IC50 (nM) | TNFα (THP-1) IC50 (nM) |
|---|---|---|---|
| 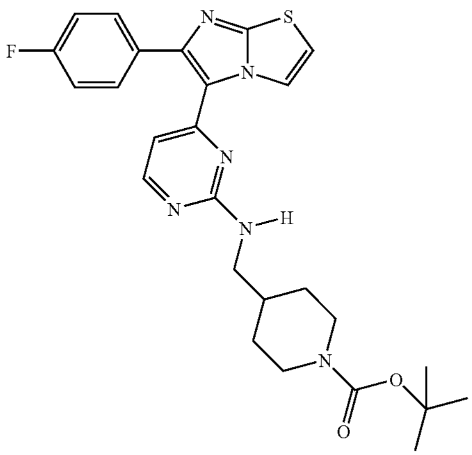 | CCXXXVIII | 87.6 | 162 |
| 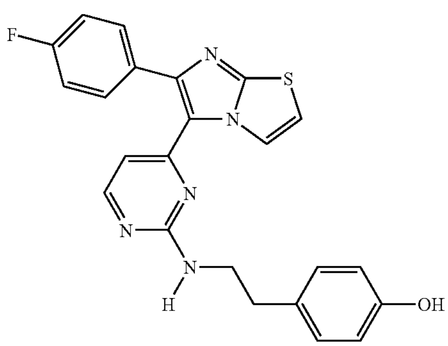 | CCXXXIX | 5.82 | 21 |
| 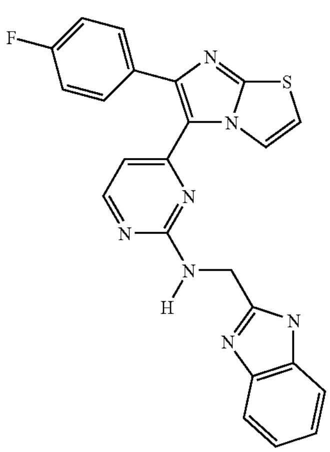 | CCXL | 135 | 3300 |

TABLE 2-continued
| Structure | Compounds | p38α (ELISA) IC50 (nM) | TNFα (THP-1) IC50 (nM) |
|---|---|---|---|
| 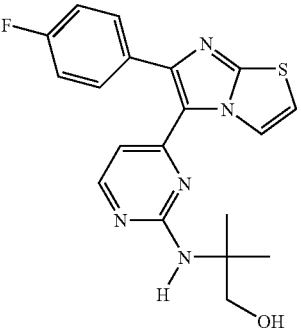 | CCXLI | 2.81 | 5.18 |
| 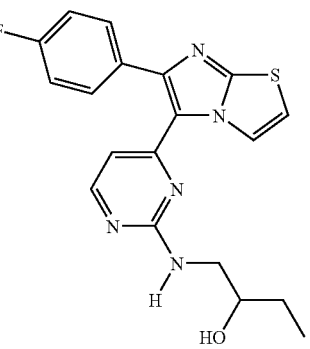 | CCXLII | 3.28 | 3.83 |
| 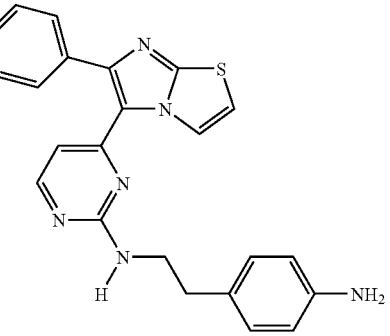 | CCXLIII | 2.19 | 19.5 |
| 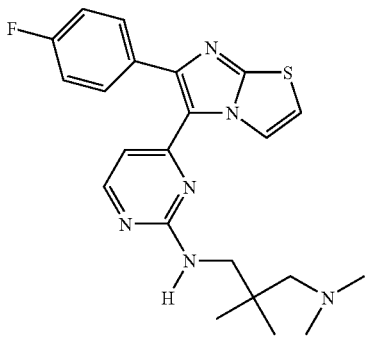 | CCXLIV | 11.4 | 5.98 |

TABLE 2-continued

| Structure | Compounds | p38α (ELISA) IC50 (nM) | TNFα (THP-1) IC50 (nM) |
|---|---|---|---|
| 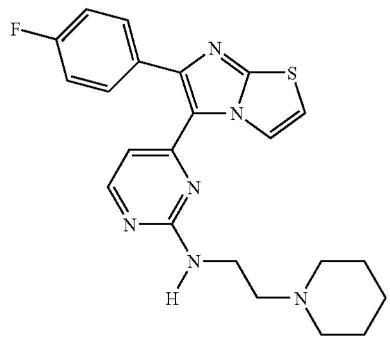 | CCXLV | 82.1 | 14.2 |
| 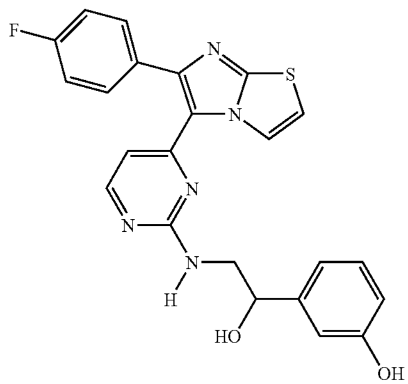 | CCXLVI | 3.06 | 23.9 |
| 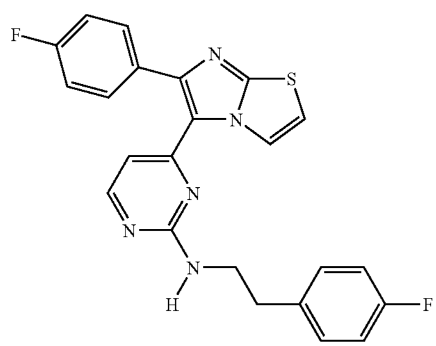 | CCXLVII | 4.84 | 33.2 |
| 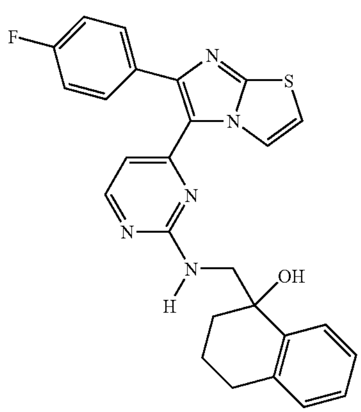 | CCXLVIII | 8.39 | 20.8 |

TABLE 2-continued
| Structure | Compounds | p38α (ELISA) IC50 (nM) | TNFα (THP-1) IC50 (nM) |
|---|---|---|---|
| 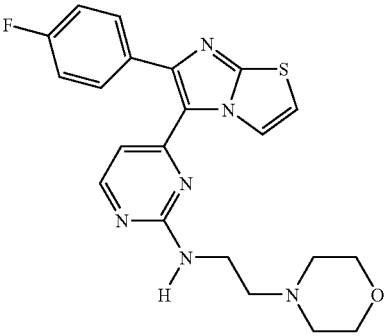 | CCXLIX | 31.6 | 20.3 |
| 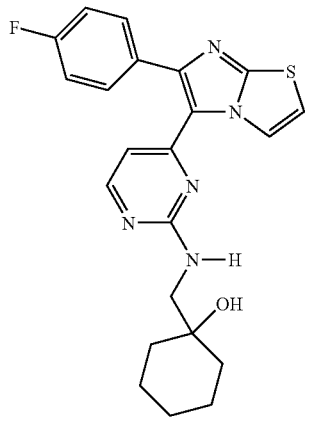 | CCL | 27.2 | 15.5 |
| 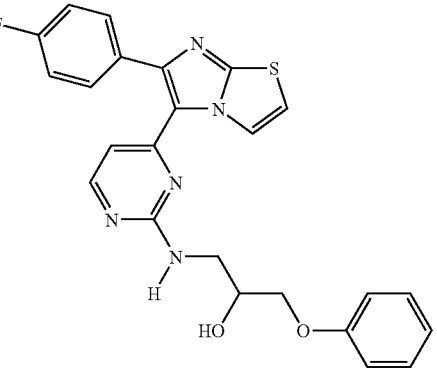 | CCLI | 14.3 | 84.9 |
| 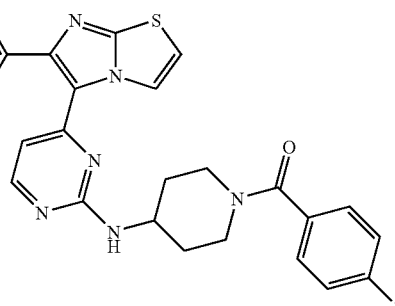 | CCLII | 2.02 | 21.9 |

TABLE 2-continued

| Structure | Compounds | p38α (ELISA) IC50 (nM) | TNFα (THP-1) IC50 (nM) |
|---|---|---|---|
| 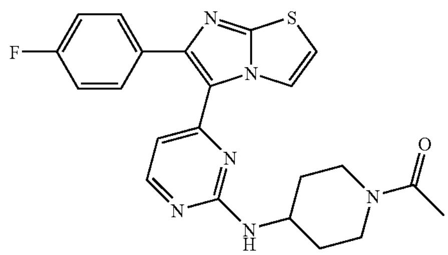 | CCLIII | 1.65 | 6.27 |
| 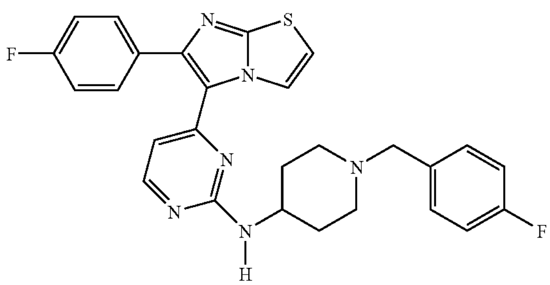 | CCLIV | 30.2 | 345 |
| 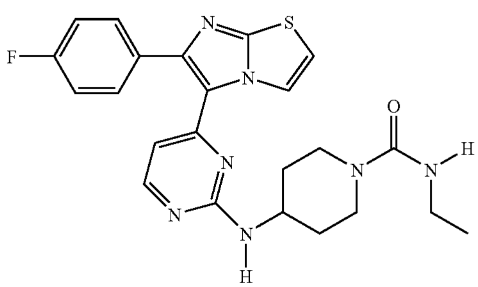 | CCLV | 2.12 | 10.8 |
| 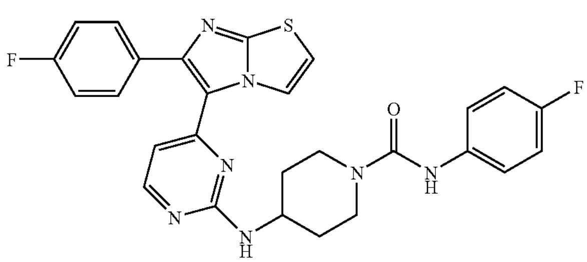 | CCLVI | 1.07 | 9.68 |
| 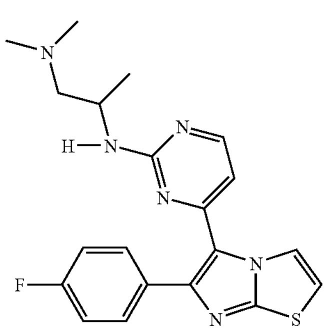 | CCLVII | 25.4 | 38.6 |

TABLE 2-continued

| Structure | Compounds | p38α (ELISA) IC50 (nM) | TNFα (THP-1) IC50 (nM) |
|---|---|---|---|
| 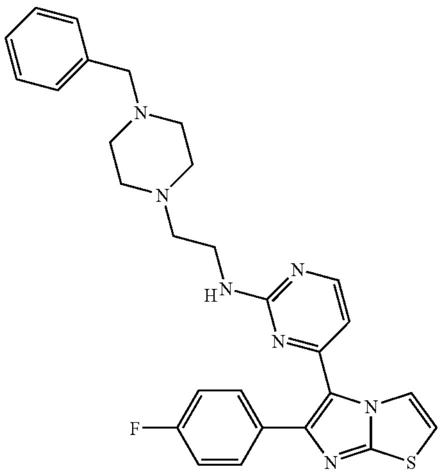 | CCLVIII | 57.7 | 643 |
| Chiral | CCLIX | 22.2 | 47.7 |
| 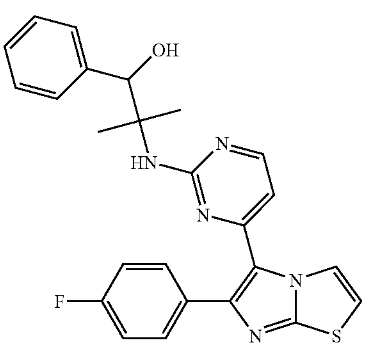 | CCLX | 30 | 213 |
| 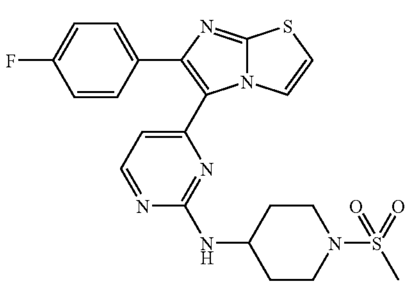 | CCLXI | 1.31 | 3.08 |

TABLE 2-continued
| Structure | Compounds | p38α (ELISA) IC50 (nM) | TNFα (THP-1) IC50 (nM) |
|---|---|---|---|
| 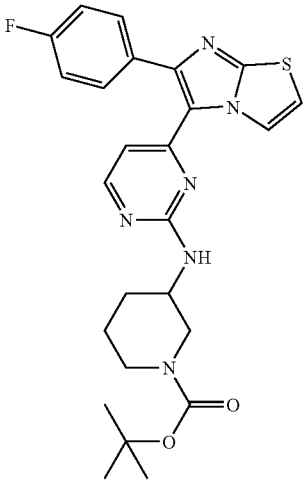 | CCLXII | 29.8 | 196 |
| 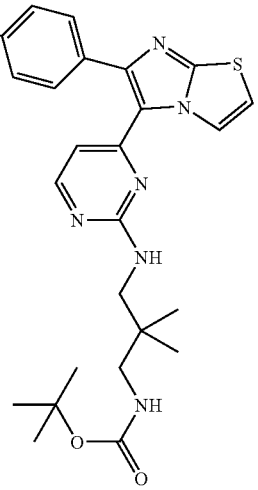 | CCLXIII | 5.85 | 23.3 |
| Chiral 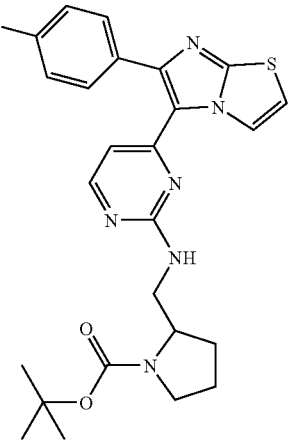 | CCLXIV | 7.26 | 27.5 |

TABLE 2-continued

| Structure | Compounds | p38α (ELISA) IC50 (nM) | TNFα (THP-1) IC50 (nM) |
|---|---|---|---|
| 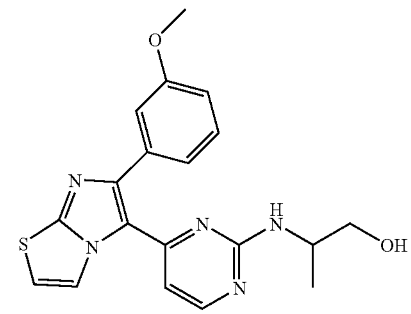 | CCLXV | 44.7 | |
| Chiral | CCLXVI | 819 | |
| 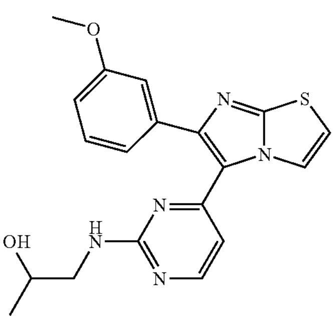 | CCLXVII | 61.2 | |
| 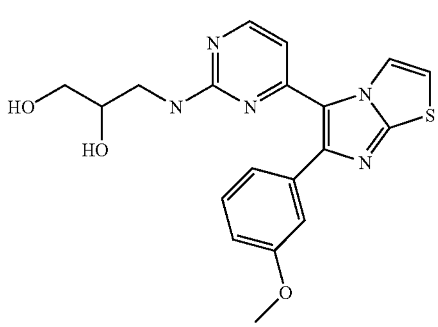 | CCLXVIII | 649 | |

TABLE 2-continued

| Structure | Compounds | p38α (ELISA) IC50 (nM) | TNFα (THP-1) IC50 (nM) |
|---|---|---|---|
| 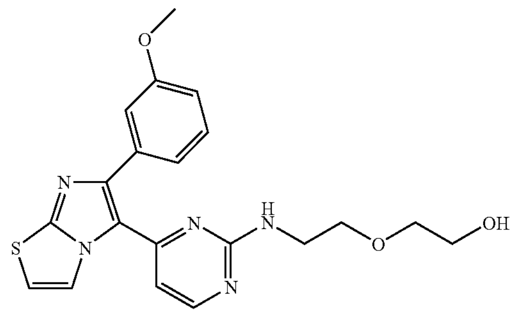 | CCLXIX | 428 | |
| Chiral | CCLXX | 112 | 93.5 |
| Chiral | CCLXXI | 75.7 | 100 |
| Chiral | CCLXXII | 924 | |

TABLE 2-continued

| Structure | Compounds | p38α (ELISA) IC50 (nM) | TNFα (THP-1) IC50 (nM) |
|---|---|---|---|
| Chiral | CCLXXIII | 1410 | |
| 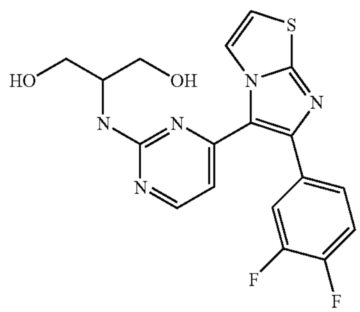 | CCLXXIV | 609 | |
| Chiral | CCLXXV | 191 | 43.3 |
| 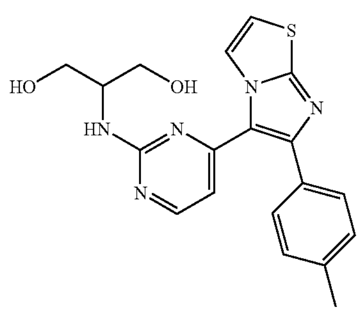 | CCLXXVI | 558 | |

TABLE 2-continued

| Structure | Compounds | p38α (ELISA) IC50 (nM) | TNFα (THP-1) IC50 (nM) |
|---|---|---|---|
| Chiral 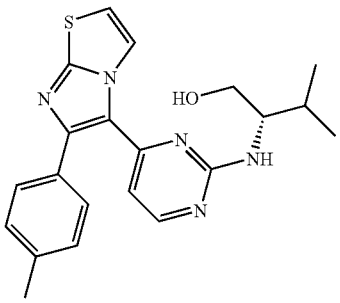 | CCLXXVII | 147 | 58.7 |

What is claimed is:

1. A compound of Formula I;

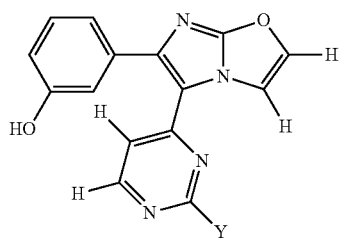

Formula I wherein
Y is $NR_4R_5$;
$R_4$ is hydrogen; and
$R_5$ is nitrogen-containing heterocyclyl, wherein the nitrogen in the heterocyclyl is optionally substituted with hydrogen, $C_1$-$C_6$-alkyl, $C_3$-$C_6$-cycloalkyl, $C_2$-$C_6$-alkenyl, $C_2$-$C_6$-alkynyl, aryl, aminocarbonyl, $C_1$-$C_6$-alkyl carbonyl, arylcarbonyl, aryloxycarbonyl, $C_1$-$C_6$-alkoxycarbonyl, $C_1$-$C_6$-alkylsulfonyl, arylsulfonyl, or heterocyclyl group,
or a pharmaceutically acceptable salt of a compound of Formula I.

2. The compound according to claim 1, wherein said compound is a pharmaceutically acceptable salt.

3. A pharmaceutical composition comprising one or more compounds represented by Formula I as defined by claim 1 and pharmaceutically acceptable carrier.

4. A method for treating a p38-associated cancer comprising identifying a subject in need of treatment and administering to the subject an amount of a compound of Formula I as defined by claim 1 effective to treat said p38-associated cancer, wherein said p38-associated cancer is selected from a group consisting of breast cancer, colorectal cancer, melanoma, gastric cancer and lung cancer.

5. The method according to claim 4, wherein the compound of Formula I is combined with another pharmaceutically-active agent.

6. The method according to claim 4, wherein said subject is a mammal selected from the group consisting of cattle, pigs, sheep, goats, horses, camels, buffalo, cats, dogs, rats, mice, and humans.

7. The method according to claim 4, wherein said subject is a human.

8. The method according to claim 4, wherein said p38-associated cancer is associated with a specific isoform of p38.

9. The method according to claim 8, wherein said specific isoform of p38 is selected from the group consisting of p38α, p38β, p38δ, and p38γ.

10. The method according to claim 9, wherein said specific isoform of p38 is p38α.

11. A method for treating arthritis comprising identifying a subject in need of treatment and administering to the subject an amount of the compound of claim 1 effective to treat the arthritis.

* * * * *

UNITED STATES PATENT AND TRADEMARK OFFICE
CERTIFICATE OF CORRECTION

Page 1 of 1

PATENT NO. : 7,902,192 B2
APPLICATION NO. : 10/556161
DATED : March 8, 2011
INVENTOR(S) : Ashwell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this
Eighteenth Day of October, 2011

David J. Kappos
*Director of the United States Patent and Trademark Office*